US009340826B2

(12) United States Patent
Bang et al.

(10) Patent No.: US 9,340,826 B2
(45) Date of Patent: May 17, 2016

(54) METHOD OF PREPARING NUCLEIC ACID MOLECULES

(75) Inventors: Duhee Bang, Seoul (KR); Hwangbeom Kim, Seoul (KR); Hyojun Han, Seoul (KR)

(73) Assignee: CELEMICS, INC., Seoul (KR)

( * ) Notice: Subject to any disclaimer, the term of this patent is extended or adjusted under 35 U.S.C. 154(b) by 155 days.

(21) Appl. No.: 14/235,799

(22) PCT Filed: Aug. 1, 2012

(86) PCT No.: PCT/KR2012/006147
§ 371 (c)(1),
(2), (4) Date: Jan. 29, 2014

(87) PCT Pub. No.: WO2013/019075
PCT Pub. Date: Feb. 7, 2013

(65) Prior Publication Data

US 2014/0309118 A1 Oct. 16, 2014

(30) Foreign Application Priority Data

Aug. 1, 2011 (KR) ........................ 10-2011-0076408

(51) Int. Cl.
*C12Q 1/68* (2006.01)
*C12N 15/10* (2006.01)

(52) U.S. Cl.
CPC .......... *C12Q 1/6806* (2013.01); *C12N 15/1027* (2013.01); *C12N 15/1031* (2013.01); *C12N 15/1065* (2013.01); *C12N 15/1093* (2013.01)

(58) Field of Classification Search
None
See application file for complete search history.

(56) References Cited

U.S. PATENT DOCUMENTS

2010/0016178 A1 1/2010 Sussman et al.
2010/0069263 A1 * 3/2010 Shendure et al. ............... 506/26

OTHER PUBLICATIONS

Yehezkel et al. (De novo DNA synthesis using single molecule PCR, Nucleic Acids Res. Oct. 2008; 36(17): e107. Published online Jul. 30, 2008).*

Kim et al. (Hierarchical gene synthesis using DNA microchip oligonucleotides, J Biotechnol. Feb. 20, 2011;151(4):319-24. Epub Jan. 13, 2011).*

Kosuri et al. (Scalable gene synthesis by selective amplification of DNA pools from high-fidelity microchips, Nature Biotechnology 28, 1295-1299 (2010), Published online Nov. 28, 2010).*

Matzas et al. (High-fidelity gene synthesis by retrieval of sequence-verified DNA identified using high-throughput pyrosequencing, Nature Biotechnology 28, 1291-1294 (2010), Published online Nov. 28, 2010).*

Kim, H. et al. "'Shotgun DNA synthesis' for the high-throughput construction of large DNA molecules", Nucleic Acids Res., Oct. 2012, vol. 40, No. 18, e140 (Epub. Jun. 16, 2012).

Maeda, N. et al., "Development of a DNA barcode tagging method for monitoring dynamic changes in gene expression by using an ultra high-throughput sequencer", Biotechniques, Jul. 2008, vol. 45, No. 1, pp. 95-97.

Carr, I. M. et al., "Illuminator, a desktop program for mutation detection using short-read clonal sequencing", Genomics, Oct. 2011, vol. 98, No. 4, pp. 302-309 (Epub. May 19, 2011).

Sakiyama, T. et al., "An automated system for genome analysis to support microbial whole-genome shotgun sequencing", Biosci. Biotechnol. Biochem., Mar. 2000, vol. 64, No. 3, pp. 670-673.

Jingdong Tian et al., "Accurate multiplex gene synthesis from programmable DNA microchips", Nature, vol. 432, Dec. 23/30, 2004, pp. 1050-1054.

Hutchison et al., "Cell-free cloning using Φ29 DNA polymerase", PNAS, Nov. 29, 2005, vol. 102, No. 48, pp. 17332-17336.

Kun Zhang et al., "Sequencing genomes from single cells by polymerase cloning", Nature Biotechnology, vol. 24, No. 6, Jun. 2006, pp. 680-686.

Pere Puigbo et al., "OPTIMIZER: a web server for optimizing the codon usage of DNA sequences", Nucleic Acids Research, 2007, vol. 35, Web Server issue.

Tuval Ben Yehezkel et al., "De novo DNA synthesis using single molecule PCR, Nucleic Acids Research", 2008, vol. 36, No. 17.

John Eid et al., "Real-Time DNA Sequencing from Single Polymerase Molecules", Science, vol. 323, Jan. 2, 2009, pp. 133-138.

Alex Y. Borovkov et al., "High-quality gene assembly directly from unpurified mixtures of microarray-synthesized oligonucleotides", Nucleic Acids Research, 2010, vol. 38, No. 19.

Kim et al., "A Fluorescence Selection Method for Accurate Large-Gene Synthesis", ChemBioChem 2010, 11, pp. 2448-2452.

Sriram Kosuri et al., "Scalable gene synthesis by selective amplification of DNA pools from high-fidelity microchips", Nature Biotechnology, vol. 28, No. 12, Dec. 2010, pp. 1295-1299.

Mark Matzas et al., "High-fidelity gene synthesis by retrieval of sequence-verified DNA identified using high-throughput pyrosequencing", Nature Biotechnology, vol. 28, No. 12, Dec. 2010, pp. 1291-1294.

Kim et al., "Hierarchical gene synthesis using DNA microchip oligonucleotides", Journal of Biotechnology, 151 (2011), pp. 319-324.

* cited by examiner

*Primary Examiner* — Gary Benzion
*Assistant Examiner* — Aaron Priest
(74) *Attorney, Agent, or Firm* — Revolution IP, PLLC

(57) ABSTRACT

Provided is a method of preparing nucleic acid molecules comprising: (a) a step of providing nucleic acid fragments constituting at least a portion of the complete sequence of a target nucleic acid; (b) tagging the nucleic acid fragments with barcode sequences; (c) identifying the sequence of the nucleic acid fragments tagged by the barcode sequences; and (d) recovering desired nucleic acid fragments among the sequence-identified nucleic acid fragments using the barcode sequences.

10 Claims, 9 Drawing Sheets

SEQUENCE LISTING

```
<160> NUMBER OF SEQ ID NOS: 284

<210> SEQ ID NO 1
<211> LENGTH: 24
<212> TYPE: DNA
<213> ORGANISM: Artificial Sequence
<220> FEATURE:
<223> OTHER INFORMATION: Synthetic nucelotide

<400> SEQUENCE: 1

gcagagtaaa gaccgtgcac ttat                                            24


<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2

ctatttgatg ttcgtagttc cag                                             23


<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3

agccttttca aagcgaaag                                                  19


<210> SEQ ID NO 4
<211> LENGTH: 23
<212> TYPE: DNA
<213> ORGANISM: Artificial Sequence
<220> FEATURE:
<223> OTHER INFORMATION: Synthetic primer

<400> SEQUENCE: 4

atctattagg tcatagtagg cag                                             23


<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5

catgcagagg aaaccataaa                                                 20


<210> SEQ ID NO 6
<211> LENGTH: 23
<212> TYPE: DNA
```

```
<213> ORGANISM: Artificial Sequence
<220> FEATURE:
<223> OTHER INFORMATION: Synthetic primer

<400> SEQUENCE: 6

tgctattctt tctgcctttt cag                                      23

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7

gaatgtttgt tgcgtttcca                                          20

<210> SEQ ID NO 8
<211> LENGTH: 22
<212> TYPE: DNA
<213> ORGANISM: Artificial Sequence
<220> FEATURE:
<223> OTHER INFORMATION: Synthetic primer

<400> SEQUENCE: 8

tcgagctcaa tagttttttc ag                                       22

<210> SEQ ID NO 9
<211> LENGTH: 23
<212> TYPE: DNA
<213> ORGANISM: Artificial Sequence
<220> FEATURE:
<223> OTHER INFORMATION: Synthetic primer

<400> SEQUENCE: 9

tttatgattg cattcagcag cag                                      23

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10

ttactccatt ttgcactctc ag                                       22

<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11

attctttggc ctttgttgac ag                                       22

<210> SEQ ID NO 12
<211> LENGTH: 27
<212> TYPE: DNA
<213> ORGANISM: Artificial Sequence
<220> FEATURE:
<223> OTHER INFORMATION: Synthetic primer

<400> SEQUENCE: 12

ttagtttcaa catgtatata cagcagc                                  27
```

-continued

<210> SEQ ID NO 13
<211> LENGTH: 24
<212> TYPE: DNA
<213> ORGANISM: Artificial Sequence
<220> FEATURE:
<223> OTHER INFORMATION: Synthetic primer

<400> SEQUENCE: 13
atgtgtatat tcgacacttt cagc 24

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
gtgaatatcc gtctagcaag c 21

<210> SEQ ID NO 15
<211> LENGTH: 24
<212> TYPE: DNA
<213> ORGANISM: Artificial Sequence
<220> FEATURE:
<223> OTHER INFORMATION: Synthetic primer

<400> SEQUENCE: 15
cagttcacgt tcgtcgcaca ccac 24

<210> SEQ ID NO 16
<211> LENGTH: 19
<212> TYPE: DNA
<213> ORGANISM: Artificial Sequence
<220> FEATURE:
<223> OTHER INFORMATION: Synthetic primer

<400> SEQUENCE: 16
ctattttcag tgtgccttt 19

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
tcctaagttg atgaaacttt 20

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
tatctggtag gaggggtt 18

<210> SEQ ID NO 19
<211> LENGTH: 20
<212> TYPE: DNA
<213> ORGANISM: Artificial Sequence
<220> FEATURE:

-continued

<223> OTHER INFORMATION: Synthetic primer

<400> SEQUENCE: 19
tagaactggc aatgacgctg 20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
ttctgtttgt cttaaatgcg 20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
taccgttttt aagattgcgt 20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
ctgaaattca tttatgtttg 20

<210> SEQ ID NO 23
<211> LENGTH: 18
<212> TYPE: DNA
<213> ORGANISM: Artificial Sequence
<220> FEATURE:
<223> OTHER INFORMATION: Synthetic primer

<400> SEQUENCE: 23
ctatggggta cctttttg 18

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
atattcgagc gtatgtatta 20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
aagtgattgt ttacagtctc 20

-continued

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
tcatttcgag aaaaggccga 20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
gggttctttc ccttattttg 20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
aacgaggata tacaaatata 20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
aagtgttgag agtggtatat 20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
atggagcttt tatgtggtta 20

<210> SEQ ID NO 31
<211> LENGTH: 20
<212> TYPE: DNA
<213> ORGANISM: Artificial Sequence
<220> FEATURE:
<223> OTHER INFORMATION: Synthetic primer

<400> SEQUENCE: 31
aattgtctag tttcgttgtt 20

<210> SEQ ID NO 32
<211> LENGTH: 20
<212> TYPE: DNA
<213> ORGANISM: Artificial Sequence
<220> FEATURE:
<223> OTHER INFORMATION: Synthetic primer

<400> SEQUENCE: 32
tgttggttgt tcaatggagt 20

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
atacttgttt caattttgtc cagc 24

<210> SEQ ID NO 34
<211> LENGTH: 24
<212> TYPE: DNA
<213> ORGANISM: Artificial Sequence
<220> FEATURE:
<223> OTHER INFORMATION: Synthetic primer

<400> SEQUENCE: 34
tatttttttc caatttttta cagc 24

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
atcctctgct attctgttgc 20

<210> SEQ ID NO 36
<211> LENGTH: 63
<212> TYPE: DNA
<213> ORGANISM: Artificial Sequence
<220> FEATURE:
<223> OTHER INFORMATION: Synthetic primer

<400> SEQUENCE: 36
acctgcatcc agctgattgc gcgtatccgt cagcgtcagc gtttgtctgt gtctatctct 60
gtg 63

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
gggaaagggt ggtgttgtaa 20

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
ctaatttgaa tgcagtccgt 20

<210> SEQ ID NO 39
<211> LENGTH: 21
<212> TYPE: DNA
<213> ORGANISM: Artificial Sequence
<220> FEATURE:
<223> OTHER INFORMATION: Synthetic primer

<400> SEQUENCE: 39
acattacctt tggaaaaaac c 21

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
catggaacaa agtgatgctt 20

<210> SEQ ID NO 41
<211> LENGTH: 19
<212> TYPE: DNA
<213> ORGANISM: Artificial Sequence
<220> FEATURE:
<223> OTHER INFORMATION: Synthetic primer

<400> SEQUENCE: 41
tccagcagct ggaagactt 19

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
ttaagtatga ttaatgctgt ca 22

<210> SEQ ID NO 43
<211> LENGTH: 23
<212> TYPE: DNA
<213> ORGANISM: Artificial Sequence
<220> FEATURE:
<223> OTHER INFORMATION: Synthetic primer

<400> SEQUENCE: 43
cgatattgtt cataatatgt cag 23

<210> SEQ ID NO 44
<211> LENGTH: 19
<212> TYPE: DNA
<213> ORGANISM: Artificial Sequence
<220> FEATURE:
<223> OTHER INFORMATION: Synthetic primer

<400> SEQUENCE: 44
tctgcgcttc tcttgggaa 19

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
ggcgtaaatc ttccagttta 20

<210> SEQ ID NO 46
<211> LENGTH: 18
<212> TYPE: DNA
<213> ORGANISM: Artificial Sequence
<220> FEATURE:
<223> OTHER INFORMATION: Synthetic primer

<400> SEQUENCE: 46
gtggtatgca cgttggtc 18

<210> SEQ ID NO 47
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(14)
<223> OTHER INFORMATION: n is a, c, g, or t

<400> SEQUENCE: 47
tatgtgagtg atcnccgttt cag 23

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48
tggtgcagta gaagaccgta 20

<210> SEQ ID NO 49
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
tttttcgaac agaagcggta 20

<210> SEQ ID NO 50
<211> LENGTH: 21
<212> TYPE: DNA
<213> ORGANISM: Artificial Sequence
<220> FEATURE:
<223> OTHER INFORMATION: Synthetic primer

<400> SEQUENCE: 50
attacttagg gtattgcgtt c 21

<210> SEQ ID NO 51
<211> LENGTH: 20
<212> TYPE: DNA
<213> ORGANISM: Artificial Sequence
<220> FEATURE:
<223> OTHER INFORMATION: Synthetic primer

<400> SEQUENCE: 51
agaccttcag tctttgcgat 20

<210> SEQ ID NO 52
<211> LENGTH: 22
<212> TYPE: DNA
<213> ORGANISM: Artificial Sequence
<220> FEATURE:
<223> OTHER INFORMATION: Synthetic primer

<400> SEQUENCE: 52
cgtttacctg atcaaacaca gc 22

<210> SEQ ID NO 53
<211> LENGTH: 18
<212> TYPE: DNA
<213> ORGANISM: Artificial Sequence
<220> FEATURE:
<223> OTHER INFORMATION: Synthetic primer

<400> SEQUENCE: 53
agctgcactt tatagcgg 18

<210> SEQ ID NO 54
<211> LENGTH: 23
<212> TYPE: DNA
<213> ORGANISM: Artificial Sequence
<220> FEATURE:
<223> OTHER INFORMATION: Synthetic primer

<400> SEQUENCE: 54
atagcgttat taatttctgt cag 23

<210> SEQ ID NO 55
<211> LENGTH: 20
<212> TYPE: DNA
<213> ORGANISM: Artificial Sequence
<220> FEATURE:
<223> OTHER INFORMATION: Synthetic primer

<400> SEQUENCE: 55
atagttattc ggctagtcct 20

<210> SEQ ID NO 56
<211> LENGTH: 20
<212> TYPE: DNA
<213> ORGANISM: Artificial Sequence
<220> FEATURE:
<223> OTHER INFORMATION: Synthetic primer

<400> SEQUENCE: 56
tgctctgtta aacgaacgca 20

<210> SEQ ID NO 57
<211> LENGTH: 21
<212> TYPE: DNA
<213> ORGANISM: Artificial Sequence
<220> FEATURE:
<223> OTHER INFORMATION: Synthetic primer

<400> SEQUENCE: 57
ttgcgaccag aaatagtggt g 21

<210> SEQ ID NO 58
<211> LENGTH: 20
<212> TYPE: DNA
<213> ORGANISM: Artificial Sequence
<220> FEATURE:

<223> OTHER INFORMATION: Synthetic primer

<400> SEQUENCE: 58
tcatagagga ggtgctatgg 20

<210> SEQ ID NO 59
<211> LENGTH: 20
<212> TYPE: DNA
<213> ORGANISM: Artificial Sequence
<220> FEATURE:
<223> OTHER INFORMATION: Synthetic primer

<400> SEQUENCE: 59
cggatcgttt attgactgtt 20

<210> SEQ ID NO 60
<211> LENGTH: 20
<212> TYPE: DNA
<213> ORGANISM: Artificial Sequence
<220> FEATURE:
<223> OTHER INFORMATION: Synthetic primer

<400> SEQUENCE: 60
gatatttcgc ggttctgttg 20

<210> SEQ ID NO 61
<211> LENGTH: 23
<212> TYPE: DNA
<213> ORGANISM: Artificial Sequence
<220> FEATURE:
<223> OTHER INFORMATION: Synthetic primer

<400> SEQUENCE: 61
aggtaaaggt tacttaaact cag 23

<210> SEQ ID NO 62
<211> LENGTH: 20
<212> TYPE: DNA
<213> ORGANISM: Artificial Sequence
<220> FEATURE:
<223> OTHER INFORMATION: Synthetic primer

<400> SEQUENCE: 62
tagtctttgc cggtttatta 20

<210> SEQ ID NO 63
<211> LENGTH: 18
<212> TYPE: DNA
<213> ORGANISM: Artificial Sequence
<220> FEATURE:
<223> OTHER INFORMATION: Synthetic primer

<400> SEQUENCE: 63
ttgcaaagat tctacaga 18

<210> SEQ ID NO 64
<211> LENGTH: 20
<212> TYPE: DNA
<213> ORGANISM: Artificial Sequence
<220> FEATURE:
<223> OTHER INFORMATION: Synthetic primer

<400> SEQUENCE: 64
ctaaactctt tacttcctat 20

-continued

<210> SEQ ID NO 65
<211> LENGTH: 20
<212> TYPE: DNA
<213> ORGANISM: Artificial Sequence
<220> FEATURE:
<223> OTHER INFORMATION: Synthetic primer

<400> SEQUENCE: 65
agctcgttat tatgtggctt 20

<210> SEQ ID NO 66
<211> LENGTH: 20
<212> TYPE: DNA
<213> ORGANISM: Artificial Sequence
<220> FEATURE:
<223> OTHER INFORMATION: Synthetic primer

<400> SEQUENCE: 66
ttatgagaaa tgtttcactg 20

<210> SEQ ID NO 67
<211> LENGTH: 20
<212> TYPE: DNA
<213> ORGANISM: Artificial Sequence
<220> FEATURE:
<223> OTHER INFORMATION: Synthetic primer

<400> SEQUENCE: 67
tagaacacta tcaaatctag 20

<210> SEQ ID NO 68
<211> LENGTH: 23
<212> TYPE: DNA
<213> ORGANISM: Artificial Sequence
<220> FEATURE:
<223> OTHER INFORMATION: Synthetic primer

<400> SEQUENCE: 68
tttgtaattt gactctgatg cag 23

<210> SEQ ID NO 69
<211> LENGTH: 24
<212> TYPE: DNA
<213> ORGANISM: Artificial Sequence
<220> FEATURE:
<223> OTHER INFORMATION: Synthetic primer

<400> SEQUENCE: 69
taggaatctt ttgacttttc acag 24

<210> SEQ ID NO 70
<211> LENGTH: 23
<212> TYPE: DNA
<213> ORGANISM: Artificial Sequence
<220> FEATURE:
<223> OTHER INFORMATION: Synthetic primer

<400> SEQUENCE: 70
tactgggagc aaacaattct cag 23

<210> SEQ ID NO 71
<211> LENGTH: 22
<212> TYPE: DNA
<213> ORGANISM: Artificial Sequence
<220> FEATURE:
<223> OTHER INFORMATION: Synthetic primer

<400> SEQUENCE: 71
ttcgtctgct gttttcactc ag 22

<210> SEQ ID NO 72
<211> LENGTH: 24
<212> TYPE: DNA
<213> ORGANISM: Artificial Sequence
<220> FEATURE:
<223> OTHER INFORMATION: Synthetic primer

<400> SEQUENCE: 72
ctaactacgt tttcgatcac ttcg 24

<210> SEQ ID NO 73
<211> LENGTH: 21
<212> TYPE: DNA
<213> ORGANISM: Artificial Sequence
<220> FEATURE:
<223> OTHER INFORMATION: Synthetic primer

<400> SEQUENCE: 73
ttcacggatt ttgtcgaaga c 21

<210> SEQ ID NO 74
<211> LENGTH: 18
<212> TYPE: DNA
<213> ORGANISM: Artificial Sequence
<220> FEATURE:
<223> OTHER INFORMATION: Synthetic primer

<400> SEQUENCE: 74
gtgggatgga agctcctc 18

<210> SEQ ID NO 75
<211> LENGTH: 23
<212> TYPE: DNA
<213> ORGANISM: Artificial Sequence
<220> FEATURE:
<223> OTHER INFORMATION: Synthetic primer

<400> SEQUENCE: 75
tgtattatgt cctttttgcc agc 23

<210> SEQ ID NO 76
<211> LENGTH: 57
<212> TYPE: DNA
<213> ORGANISM: Artificial Sequence
<220> FEATURE:
<223> OTHER INFORMATION: Synthetic primer

<400> SEQUENCE: 76
gctttcagcg agccggtctt cgacaaaatc cgtgaaacct tccacggttt ggttatc 57

<210> SEQ ID NO 77
<211> LENGTH: 18
<212> TYPE: DNA
<213> ORGANISM: Artificial Sequence
<220> FEATURE:
<223> OTHER INFORMATION: Synthetic primer

<400> SEQUENCE: 77
caggtacagc tcacccac 18

<210> SEQ ID NO 78
<211> LENGTH: 20

<212> TYPE: DNA
<213> ORGANISM: Artificial Sequence
<220> FEATURE:
<223> OTHER INFORMATION: Synthetic primer

<400> SEQUENCE: 78
tgttggatat atagggttac 20

<210> SEQ ID NO 79
<211> LENGTH: 20
<212> TYPE: DNA
<213> ORGANISM: Artificial Sequence
<220> FEATURE:
<223> OTHER INFORMATION: Synthetic primer

<400> SEQUENCE: 79
catggggatg atgtgtactt 20

<210> SEQ ID NO 80
<211> LENGTH: 20
<212> TYPE: DNA
<213> ORGANISM: Artificial Sequence
<220> FEATURE:
<223> OTHER INFORMATION: Synthetic primer

<400> SEQUENCE: 80
aattcactca gaataatttt 20

<210> SEQ ID NO 81
<211> LENGTH: 20
<212> TYPE: DNA
<213> ORGANISM: Artificial Sequence
<220> FEATURE:
<223> OTHER INFORMATION: Synthetic primer

<400> SEQUENCE: 81
atttagttgg aattaatctc 20

<210> SEQ ID NO 82
<211> LENGTH: 20
<212> TYPE: DNA
<213> ORGANISM: Artificial Sequence
<220> FEATURE:
<223> OTHER INFORMATION: Synthetic primer

<400> SEQUENCE: 82
ctactgttcg ttcccaatta 20

<210> SEQ ID NO 83
<211> LENGTH: 20
<212> TYPE: DNA
<213> ORGANISM: Artificial Sequence
<220> FEATURE:
<223> OTHER INFORMATION: Synthetic primer

<400> SEQUENCE: 83
ttggtgtaaa actgggggaa 20

<210> SEQ ID NO 84
<211> LENGTH: 20
<212> TYPE: DNA
<213> ORGANISM: Artificial Sequence
<220> FEATURE:
<223> OTHER INFORMATION: Synthetic primer

<400> SEQUENCE: 84
atgtgttata gaagttgttg 20

<210> SEQ ID NO 85
<211> LENGTH: 20
<212> TYPE: DNA
<213> ORGANISM: Artificial Sequence
<220> FEATURE:
<223> OTHER INFORMATION: Synthetic primer

<400> SEQUENCE: 85
tgacatgtgt tatccctgct 20

<210> SEQ ID NO 86
<211> LENGTH: 20
<212> TYPE: DNA
<213> ORGANISM: Artificial Sequence
<220> FEATURE:
<223> OTHER INFORMATION: Synthetic primer

<400> SEQUENCE: 86
tttcagaaac ttaaacttac 20

<210> SEQ ID NO 87
<211> LENGTH: 20
<212> TYPE: DNA
<213> ORGANISM: Artificial Sequence
<220> FEATURE:
<223> OTHER INFORMATION: Synthetic primer

<400> SEQUENCE: 87
ttataagaag taataggaat 20

<210> SEQ ID NO 88
<211> LENGTH: 20
<212> TYPE: DNA
<213> ORGANISM: Artificial Sequence
<220> FEATURE:
<223> OTHER INFORMATION: Synthetic primer

<400> SEQUENCE: 88
tatacaatct attggtaatc 20

<210> SEQ ID NO 89
<211> LENGTH: 20
<212> TYPE: DNA
<213> ORGANISM: Artificial Sequence
<220> FEATURE:
<223> OTHER INFORMATION: Synthetic primer

<400> SEQUENCE: 89
tggaatactt taatcctttc 20

<210> SEQ ID NO 90
<211> LENGTH: 20
<212> TYPE: DNA
<213> ORGANISM: Artificial Sequence
<220> FEATURE:
<223> OTHER INFORMATION: Synthetic primer

<400> SEQUENCE: 90
ttacatgctt tcgacacata 20

<210> SEQ ID NO 91
<211> LENGTH: 20
<212> TYPE: DNA
<213> ORGANISM: Artificial Sequence
<220> FEATURE:
<223> OTHER INFORMATION: Synthetic primer

<400> SEQUENCE: 91
tgtatagtgt gaggatcttt 20

<210> SEQ ID NO 92
<211> LENGTH: 20
<212> TYPE: DNA
<213> ORGANISM: Artificial Sequence
<220> FEATURE:
<223> OTHER INFORMATION: Synthetic primer

<400> SEQUENCE: 92
gttaatttct ggggatacgt 20

<210> SEQ ID NO 93
<211> LENGTH: 20
<212> TYPE: DNA
<213> ORGANISM: Artificial Sequence
<220> FEATURE:
<223> OTHER INFORMATION: Synthetic primer

<400> SEQUENCE: 93
taactcacgc tttttataag 20

<210> SEQ ID NO 94
<211> LENGTH: 22
<212> TYPE: DNA
<213> ORGANISM: Artificial Sequence
<220> FEATURE:
<223> OTHER INFORMATION: Synthetic primer

<400> SEQUENCE: 94
ttcttgtcac tctctttatc ca 22

<210> SEQ ID NO 95
<211> LENGTH: 19
<212> TYPE: DNA
<213> ORGANISM: Artificial Sequence
<220> FEATURE:
<223> OTHER INFORMATION: Synthetic primer

<400> SEQUENCE: 95
tctatcggtt ttcgggttt 19

<210> SEQ ID NO 96
<211> LENGTH: 23
<212> TYPE: DNA
<213> ORGANISM: Artificial Sequence
<220> FEATURE:
<223> OTHER INFORMATION: Synthetic primer

<400> SEQUENCE: 96
gaagcacctg tcttatttaa cag 23

<210> SEQ ID NO 97
<211> LENGTH: 18
<212> TYPE: DNA
<213> ORGANISM: Artificial Sequence
<220> FEATURE:
<223> OTHER INFORMATION: Synthetic primer

<400> SEQUENCE: 97
tgatcttccc gggtaggc 18

<210> SEQ ID NO 98
<211> LENGTH: 21
<212> TYPE: DNA
<213> ORGANISM: Artificial Sequence
<220> FEATURE:
<223> OTHER INFORMATION: Synthetic primer

<400> SEQUENCE: 98
ggtcgttctg cgtgtagata t 21

<210> SEQ ID NO 99
<211> LENGTH: 21
<212> TYPE: DNA
<213> ORGANISM: Artificial Sequence
<220> FEATURE:
<223> OTHER INFORMATION: Synthetic primer

<400> SEQUENCE: 99
ctgcagcagt ttcgtaactt c 21

<210> SEQ ID NO 100
<211> LENGTH: 20
<212> TYPE: DNA
<213> ORGANISM: Artificial Sequence
<220> FEATURE:
<223> OTHER INFORMATION: Synthetic primer

<400> SEQUENCE: 100
tcatcctatt acgatgcccg 20

<210> SEQ ID NO 101
<211> LENGTH: 20
<212> TYPE: DNA
<213> ORGANISM: Artificial Sequence
<220> FEATURE:
<223> OTHER INFORMATION: Synthetic primer

<400> SEQUENCE: 101
gcgttggaag ctttttattg 20

<210> SEQ ID NO 102
<211> LENGTH: 20
<212> TYPE: DNA
<213> ORGANISM: Artificial Sequence
<220> FEATURE:
<223> OTHER INFORMATION: Synthetic primer

<400> SEQUENCE: 102
atttataagg acgggccagc 20

<210> SEQ ID NO 103
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or t

<400> SEQUENCE: 103
aaacgntccc cgtattggta 20

<210> SEQ ID NO 104
<211> LENGTH: 20

<212> TYPE: DNA
<213> ORGANISM: Artificial Sequence
<220> FEATURE:
<223> OTHER INFORMATION: Synthetic primer

<400> SEQUENCE: 104
taatctgatc gatgctagga 20

<210> SEQ ID NO 105
<211> LENGTH: 20
<212> TYPE: DNA
<213> ORGANISM: Artificial Sequence
<220> FEATURE:
<223> OTHER INFORMATION: Synthetic primer

<400> SEQUENCE: 105
ttttgattca atcctcctaa 20

<210> SEQ ID NO 106
<211> LENGTH: 22
<212> TYPE: DNA
<213> ORGANISM: Artificial Sequence
<220> FEATURE:
<223> OTHER INFORMATION: Synthetic primer

<400> SEQUENCE: 106
tttcctattt cttcattggc ag 22

<210> SEQ ID NO 107
<211> LENGTH: 20
<212> TYPE: DNA
<213> ORGANISM: Artificial Sequence
<220> FEATURE:
<223> OTHER INFORMATION: Synthetic primer

<400> SEQUENCE: 107
ttgcgatggt ttactttgat 20

<210> SEQ ID NO 108
<211> LENGTH: 20
<212> TYPE: DNA
<213> ORGANISM: Artificial Sequence
<220> FEATURE:
<223> OTHER INFORMATION: Synthetic primer

<400> SEQUENCE: 108
atcattgcac ttgttgttcg 20

<210> SEQ ID NO 109
<211> LENGTH: 20
<212> TYPE: DNA
<213> ORGANISM: Artificial Sequence
<220> FEATURE:
<223> OTHER INFORMATION: Synthetic primer

<400> SEQUENCE: 109
ggaaggtttt ttactgattt 20

<210> SEQ ID NO 110
<211> LENGTH: 20
<212> TYPE: DNA
<213> ORGANISM: Artificial Sequence
<220> FEATURE:
<223> OTHER INFORMATION: Synthetic primer

<400> SEQUENCE: 110

```
ttattcgtgg attggtgttc                                                   20


<210> SEQ ID NO 111
<211> LENGTH: 20
<212> TYPE: DNA
<213> ORGANISM: Artificial Sequence
<220> FEATURE:
<223> OTHER INFORMATION: Synthetic primer

<400> SEQUENCE: 111

atttttctag gttctgatta                                                   20


<210> SEQ ID NO 112
<211> LENGTH: 19
<212> TYPE: DNA
<213> ORGANISM: Artificial Sequence
<220> FEATURE:
<223> OTHER INFORMATION: Synthetic primer

<400> SEQUENCE: 112

tgatttcacc actaagtct                                                    19


<210> SEQ ID NO 113
<211> LENGTH: 19
<212> TYPE: DNA
<213> ORGANISM: Artificial Sequence
<220> FEATURE:
<223> OTHER INFORMATION: Synthetic primer

<400> SEQUENCE: 113

cctcctttat ttctcgtgc                                                    19


<210> SEQ ID NO 114
<211> LENGTH: 20
<212> TYPE: DNA
<213> ORGANISM: Artificial Sequence
<220> FEATURE:
<223> OTHER INFORMATION: Synthetic primer

<400> SEQUENCE: 114

taaagttatc atgtgctacc                                                   20


<210> SEQ ID NO 115
<211> LENGTH: 20
<212> TYPE: DNA
<213> ORGANISM: Artificial Sequence
<220> FEATURE:
<223> OTHER INFORMATION: Synthetic primer

<400> SEQUENCE: 115

tgtaaaccta tattcatctc                                                   20


<210> SEQ ID NO 116
<211> LENGTH: 23
<212> TYPE: DNA
<213> ORGANISM: Artificial Sequence
<220> FEATURE:
<223> OTHER INFORMATION: Synthetic primer

<400> SEQUENCE: 116

gttcattgca taatgcttct cag                                               23


<210> SEQ ID NO 117
<211> LENGTH: 24
<212> TYPE: DNA
<213> ORGANISM: Artificial Sequence
```

<220> FEATURE:
<223> OTHER INFORMATION: Synthetic primer

<400> SEQUENCE: 117
ttaaagccct ttacatccag cagc 24

<210> SEQ ID NO 118
<211> LENGTH: 21
<212> TYPE: DNA
<213> ORGANISM: Artificial Sequence
<220> FEATURE:
<223> OTHER INFORMATION: Synthetic primer

<400> SEQUENCE: 118
ctaacccgtt ctgcaaggaa g 21

<210> SEQ ID NO 119
<211> LENGTH: 16
<212> TYPE: DNA
<213> ORGANISM: Artificial Sequence
<220> FEATURE:
<223> OTHER INFORMATION: Synthetic primer

<400> SEQUENCE: 119
cggctgctgc tggcgg 16

<210> SEQ ID NO 120
<211> LENGTH: 20
<212> TYPE: DNA
<213> ORGANISM: Artificial Sequence
<220> FEATURE:
<223> OTHER INFORMATION: Synthetic primer

<400> SEQUENCE: 120
attgatatgt aagagatttc 20

<210> SEQ ID NO 121
<211> LENGTH: 19
<212> TYPE: DNA
<213> ORGANISM: Artificial Sequence
<220> FEATURE:
<223> OTHER INFORMATION: Synthetic primer

<400> SEQUENCE: 121
aataggtacc attttcgtt 19

<210> SEQ ID NO 122
<211> LENGTH: 23
<212> TYPE: DNA
<213> ORGANISM: Artificial Sequence
<220> FEATURE:
<223> OTHER INFORMATION: Synthetic primer

<400> SEQUENCE: 122
gattactaca tttttctcaa cag 23

<210> SEQ ID NO 123
<211> LENGTH: 20
<212> TYPE: DNA
<213> ORGANISM: Artificial Sequence
<220> FEATURE:
<223> OTHER INFORMATION: Synthetic primer

<400> SEQUENCE: 123
cttttggggg gggttgggcc 20

<210> SEQ ID NO 124
<211> LENGTH: 17
<212> TYPE: DNA
<213> ORGANISM: Artificial Sequence
<220> FEATURE:
<223> OTHER INFORMATION: Synthetic primer

<400> SEQUENCE: 124
cgtttatggg aaagcgc 17

<210> SEQ ID NO 125
<211> LENGTH: 21
<212> TYPE: DNA
<213> ORGANISM: Artificial Sequence
<220> FEATURE:
<223> OTHER INFORMATION: Synthetic primer

<400> SEQUENCE: 125
gctatccttc atgaaaacgt g 21

<210> SEQ ID NO 126
<211> LENGTH: 20
<212> TYPE: DNA
<213> ORGANISM: Artificial Sequence
<220> FEATURE:
<223> OTHER INFORMATION: Synthetic primer

<400> SEQUENCE: 126
aattggttac ctctatcccc 20

<210> SEQ ID NO 127
<211> LENGTH: 20
<212> TYPE: DNA
<213> ORGANISM: Artificial Sequence
<220> FEATURE:
<223> OTHER INFORMATION: Synthetic primer

<400> SEQUENCE: 127
ctcatactgg gatccgattt 20

<210> SEQ ID NO 128
<211> LENGTH: 20
<212> TYPE: DNA
<213> ORGANISM: Artificial Sequence
<220> FEATURE:
<223> OTHER INFORMATION: Synthetic primer

<400> SEQUENCE: 128
gcataaagcg ggaggcttct 20

<210> SEQ ID NO 129
<211> LENGTH: 19
<212> TYPE: DNA
<213> ORGANISM: Artificial Sequence
<220> FEATURE:
<223> OTHER INFORMATION: Synthetic primer

<400> SEQUENCE: 129
ctgtgtcata gaatagtgc 19

<210> SEQ ID NO 130
<211> LENGTH: 20
<212> TYPE: DNA
<213> ORGANISM: Artificial Sequence
<220> FEATURE:
<223> OTHER INFORMATION: Synthetic primer

<400> SEQUENCE: 130
tttcgaccga tttcagtctg 20

<210> SEQ ID NO 131
<211> LENGTH: 17
<212> TYPE: DNA
<213> ORGANISM: Artificial Sequence
<220> FEATURE:
<223> OTHER INFORMATION: Synthetic primer

<400> SEQUENCE: 131 tttttgacg gtaatta 17

<210> SEQ ID NO 132
<211> LENGTH: 18
<212> TYPE: DNA
<213> ORGANISM: Artificial Sequence
<220> FEATURE:
<223> OTHER INFORMATION: Synthetic primer

<400> SEQUENCE: 132
cttcctgtgg gttttcta 18

<210> SEQ ID NO 133
<211> LENGTH: 20
<212> TYPE: DNA
<213> ORGANISM: Artificial Sequence
<220> FEATURE:
<223> OTHER INFORMATION: Synthetic primer

<400> SEQUENCE: 133
ttttacatca ttcgcgtatt 20

<210> SEQ ID NO 134
<211> LENGTH: 20
<212> TYPE: DNA
<213> ORGANISM: Artificial Sequence
<220> FEATURE:
<223> OTHER INFORMATION: Synthetic primer

<400> SEQUENCE: 134
tttttgagct acgctttcgg 20

<210> SEQ ID NO 135
<211> LENGTH: 17
<212> TYPE: DNA
<213> ORGANISM: Artificial Sequence
<220> FEATURE:
<223> OTHER INFORMATION: Synthetic primer

<400> SEQUENCE: 135
tcaatacatt ctacttt 17

<210> SEQ ID NO 136
<211> LENGTH: 20
<212> TYPE: DNA
<213> ORGANISM: Artificial Sequence
<220> FEATURE:
<223> OTHER INFORMATION: Synthetic primer

<400> SEQUENCE: 136
gtcagtagta taccgttcgt 20

<210> SEQ ID NO 137

<211> LENGTH: 20
<212> TYPE: DNA
<213> ORGANISM: Artificial Sequence
<220> FEATURE:
<223> OTHER INFORMATION: Synthetic primer

<400> SEQUENCE: 137
cgatctaaga ttgccttcct 20

<210> SEQ ID NO 138
<211> LENGTH: 23
<212> TYPE: DNA
<213> ORGANISM: Artificial Sequence
<220> FEATURE:
<223> OTHER INFORMATION: Synthetic primer

<400> SEQUENCE: 138
tctcataatt gggaattgta cag 23

<210> SEQ ID NO 139
<211> LENGTH: 23
<212> TYPE: DNA
<213> ORGANISM: Artificial Sequence
<220> FEATURE:
<223> OTHER INFORMATION: Synthetic primer

<400> SEQUENCE: 139
tttatgtttt tgaattagca gca 23

<210> SEQ ID NO 140
<211> LENGTH: 20
<212> TYPE: DNA
<213> ORGANISM: Artificial Sequence
<220> FEATURE:
<223> OTHER INFORMATION: Synthetic primer

<400> SEQUENCE: 140
atcttttatg tactttgtga 20

<210> SEQ ID NO 141
<211> LENGTH: 20
<212> TYPE: DNA
<213> ORGANISM: Artificial Sequence
<220> FEATURE:
<223> OTHER INFORMATION: Synthetic primer

<400> SEQUENCE: 141
tttttcaaca cttttagtgt 20

<210> SEQ ID NO 142
<211> LENGTH: 17
<212> TYPE: DNA
<213> ORGANISM: Artificial Sequence
<220> FEATURE:
<223> OTHER INFORMATION: Synthetic primer

<400> SEQUENCE: 142
taatttcctg tgcaact 17

<210> SEQ ID NO 143
<211> LENGTH: 20
<212> TYPE: DNA
<213> ORGANISM: Artificial Sequence
<220> FEATURE:
<223> OTHER INFORMATION: Synthetic primer

<400> SEQUENCE: 143
tcttgtttat ttctttgggt 20

<210> SEQ ID NO 144
<211> LENGTH: 23
<212> TYPE: DNA
<213> ORGANISM: Artificial Sequence
<220> FEATURE:
<223> OTHER INFORMATION: Synthetic primer

<400> SEQUENCE: 144
atgtatcctc gctctttaac cag 23

<210> SEQ ID NO 145
<211> LENGTH: 22
<212> TYPE: DNA
<213> ORGANISM: Artificial Sequence
<220> FEATURE:
<223> OTHER INFORMATION: Synthetic primer

<400> SEQUENCE: 145
cacccggttt gattattact ca 22

<210> SEQ ID NO 146
<211> LENGTH: 20
<212> TYPE: DNA
<213> ORGANISM: Artificial Sequence
<220> FEATURE:
<223> OTHER INFORMATION: Synthetic primer

<400> SEQUENCE: 146
ggcattctgg cgatggagat 20

<210> SEQ ID NO 147
<211> LENGTH: 21
<212> TYPE: DNA
<213> ORGANISM: Artificial Sequence
<220> FEATURE:
<223> OTHER INFORMATION: Synthetic primer

<400> SEQUENCE: 147
gtcgtagtac tcatacaggc g 21

<210> SEQ ID NO 148
<211> LENGTH: 21
<212> TYPE: DNA
<213> ORGANISM: Artificial Sequence
<220> FEATURE:
<223> OTHER INFORMATION: Synthetic primer

<400> SEQUENCE: 148
ctaacgcatt gtcaggtttc c 21

<210> SEQ ID NO 149
<211> LENGTH: 22
<212> TYPE: DNA
<213> ORGANISM: Artificial Sequence
<220> FEATURE:
<223> OTHER INFORMATION: Synthetic primer

<400> SEQUENCE: 149
actccggata ccagtgtaga ac 22

<210> SEQ ID NO 150
<211> LENGTH: 53
<212> TYPE: DNA

<213> ORGANISM: Artificial Sequence
<220> FEATURE:
<223> OTHER INFORMATION: Synthetic primer

<400> SEQUENCE: 150
gaatcagaaa accagcgtcg cctgtatgag tactacgacg cgttagattc cac 53

<210> SEQ ID NO 151
<211> LENGTH: 31
<212> TYPE: DNA
<213> ORGANISM: Artificial Sequence
<220> FEATURE:
<223> OTHER INFORMATION: Synthetic primer

<400> SEQUENCE: 151
ttacttccaa cgaccgatgt actgagccgc c 31

<210> SEQ ID NO 152
<211> LENGTH: 392
<212> TYPE: DNA
<213> ORGANISM: Artificial Sequence
<220> FEATURE:
<223> OTHER INFORMATION: Synthetic nucleotide

<400> SEQUENCE: 152
ctatttgatg ttcgtagttc cagcagcacc gactaatgca ggctggcagt aatgacccaa 60
ttgaagccgc ctaacgggac cactccgatc ggcttcagcg ccactactag cctgaacgct 120
agcggctctt cctcggttaa gaatggtacc atcaagcctt cgaatggtat cttcaaacct 180
tctactcgtg acaccatgga cccgtgctcg ggcaacgccg ctgacggctc cattcgcgta 240
cgttttcgcg gtggcatcga acgttggaaa gagtgtgtaa accaagtgcc ggagcgttgc 300
gacctgtctg gtctgaccac ggacagcacc cgctaccagc tggcttccga acacatgacc 360
ctgcgacctg ctgagccttt tcaaagcgaa ag 392

<210> SEQ ID NO 153
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 153
atctattagg tcatagtagg cagcagaggg catcttagcg gtcgctcttc tggcttcggc 60
gacgcgagcg cggcttacca ggaacgtctg atgactgtgc cggtagatgt tcatgctgcg 120
ctccaggagc tgtgcctgga acgccgcgtc tctgtgggtt ctgtgatcaa cttcagcgtt 180
caccagatgc tgaagggttt tggcaacggt actcacacta tcaccgcgag cctgcaccgc 240
gaacagaatc tgcagaactc ctctccgtct tgggtcgttt cccctactat cgtgacccat 300
gaaaaccgcg atggctggtc agtggcgcag gcagtggagt ctatcgaggc tagaagacca 360
cacatggcac ctttgctgct gcatgcagag gaaaccataa at 402

<210> SEQ ID NO 154
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 154
tgctattctt tctgcctttt cagcagcaaa ggtgccatgt gtggctcttc tggcaacggt 60
actcacacta tcaccgcgag cctgcaccgc gaacagaatc tgcagaactc ctctccgtct 120
tgggtcgttt cccctactat cgtgacccat gaaaaccgcg atggctggtc agtggcgcag 180
gcagtggagt ctatcgaggc tggtcgtggc tccgaaaagg aatctgtgac cgcgattgat 240
tccggctcct ccctggtcaa aatgggtctg ttcgatctgc tggtttcctt cgtcgatgcg 300
gatgacgcgc gtatcccttg cttcgacttt ccgctggctg ttattgtgcg cagaagagcg 360
accgctaaga tgccctctgc tgtggaaacg caacaaacat tc 402

<210> SEQ ID NO 155
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 155
tcgagctcaa tagtttttc agcagcaccg actaatgcag gctggcgtga tgacgcgcgt 60
atcccttgct tcgactttcc gctggctgtt attgtgcgcg agtgcgatgc aaacctgtct 120
ctcacccttc gcttctcgga ctgcctgttc aacgaggaaa ccatttgtaa tttcacggat 180
gccctcaata tcctgttggc tgaggcagtt atcggtcgtg taactccggt agccgatatc 240
gagctgctgt ctgcagagca gaaacaacag ctggaggaat ggaacaacac cgatggtgaa 300
tatccgtcta gcaagcgtct gcaccacctg attgaagagg tggtggaacc actgcgaaca 360
catgaccctg cgacctgctg ctgctgaatg caatcataaa 400

<210> SEQ ID NO 156
<211> LENGTH: 389
<212> TYPE: DNA
<213> ORGANISM: Artificial Sequence
<220> FEATURE:
<223> OTHER INFORMATION: Synthetic nucleotide

<400> SEQUENCE: 156
ttactccatt ttgcactctc agcagcaccg actaatgcag gctggcatga tgacgcgcgt 60
atcccttgct tcgactttcc gctggctgtt attgtgcgcg agtgcgatgc aaacctgtct 120
ctcacccttc gcttctcttc aacgaggaaa ccatttgtaa tttcacggat gccctcaata 180
tcctgttggc tgaggcagtt atcggtcgtg taactccggt agccgatatc gagctgctgt 240
ctgcagagca gaaacaacag ctggaggaat ggaacaacac cgatggtgaa tatccgtcta 300
gcaagcgtct gcaccacctg attgaagagg tggtggaacc actacgaaca catgaccctg 360
cgacctgctg tcaacaaagg ccaaagaat 389

<210> SEQ ID NO 157
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 157
ttagtttcaa catgtatata cagcagcacc gactaatgca ggctggagtg caacgaggaa 60
accatttgta atttcacgga tgccctcaat atcctgttgg ctgaggcagt tatcggtcgt 120
gtaactccgg tagccgatat cgagctgctg tctgcagagc agaaacaaca gctggaggaa 180
tggaacaaca ccgatggtga atatccgtct agcaagcgtc tgcaccacct gattgaagag 240
gtggtggaac gtcacgaaga caaaatcgct gtggtgtgcg acgaacgtga actgacttac 300
ggtgaactca atgcccacgg caactccctg gcgcgttacc tgcacagcat cactgcgaac 360
acatgaccct gcgacctgct gaaagtgtcg aatatacaca t 401

<210> SEQ ID NO 158
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 158
ctattttcag tgtgcctttc agcagcaccg actaatgcag gctggagtgg tcacgaagac 60
aaaatcgctg tggtgtgcga cgaacgtgaa ctgacttacg gtgaactcaa tgcccagggc 120
aactccctgg cgcgttacct gcgcagcatt ggtattctgc ctgaacagct ggttgcgctg 180
tttctggaca aatccgaaaa attgatcgta accatcctgg gcgtctggaa atccggtgct 240
gcttacgtgc caattgaccc gacctaccct gacgaacgtg ttcgtttcgt tctggacgac 300
acgaaagccc gtgcgattat cgcttccaat cagcatgttg aacgcctccc actgcgaaca 360
catgaccctg cgacctgctg aaagtttcat caacttagga 400

<210> SEQ ID NO 159
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 159
tatctggtag gaggggttca gcagcaaagg tgccatgtgt ggctcttcta attgatcgta 60
accatcctgg gcgtctggaa atccggtgct gcttacgtgc caattgaccc gacctaccct 120
gacgaacgtg ttcgtttcgt tctggacgac acgaaagccc gtgcgattat cgcttccaat 180
cagcatgttg aacgcctcca gcgtgaagta atcggtgatc gcaacctgtg catcatccgt 240
ctcgaaccac tgctggcgag ccttgcgcag gattcttcta aattccctgc ccacaacctg 300
gatgatttgc cgctgaccag ccagcagctg gcgtacgtta cttataccaa gaagagtgac 360
cgctaagatg ccctctgctg cagcgtcatt gccagttcta 400

<210> SEQ ID NO 160
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 160
ttctgtttgt cttaaatgcg cagcagaggg catcttagcg gtcgctcttc tagcgtgaag 60
taatcggtga tcgcaacctg tgcatcatcc gtctcgaacc actgctggcg agccttgcgc 120
aggattcttc taaattccct gcccacaacc tggatgattt gccgctgacc agccagcagc 180
tggcgtacgt tacttatacc agcggtacca ccggctttcc gaaaggcatt ttcaaacagc 240
acactaacgt tgttaactcc atcacagacc tgtccgctcg ttacggtgtt gcaggtcaac 300
accatgaagc tatcctgctc ttcagtgctt gcgttttcga accgttcgtt cagaagagcc 360
acacatggca cctttgctgc tgacgcaatc ttaaaaacgg ta 402

<210> SEQ ID NO 161
<211> LENGTH: 383
<212> TYPE: DNA
<213> ORGANISM: Artificial Sequence
<220> FEATURE:
<223> OTHER INFORMATION: Synthetic nucleotide

<400> SEQUENCE: 161
ctgaaattca tttatgtttg cagcagcacc gactaatgca ggctggcagt ggttaactcc 60
atcacagacc tgtccgctcg ttacggtgtt gcaggtcaac accatgaagc tatcctgctc 120
ttcagtgctt gcgttttcga accgttcgtt cgtcagactc tgatggccct ggtgaacggt 180
cacctgctcg ccgtgattaa cgatgtagaa aaatatgacg ctgacaccct cctcccattt 240
atccgccgtc actctatcac ctatctgaac ggtactgcgt cggttctcca agagtatgac 300
ttctctgact gtccgagcct gaaccgtatc atcctctgcg aacacatcga ccctgcgacc 360
tgctgcaaaa aggtacccca tag 383

<210> SEQ ID NO 162
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 162
atattcgagc gtatgtatta cagcagcacc gactaatgca ggctggcgtc tctatcacct 60
atctgaacgg tactgcgtcg gttctccaag agtatgactt ctctgactgt ccgagcctga 120
accgtatcat cctggtgggc gagaacctga ccgaagcacg ttacctggca ctgcgtcagc 180
gtttcaaaaa tcgtattctg aacgagtacg gtttcaccga gtctgcgttc gtgactgcgc 240
tgaaaatttt cgatccggaa agcacccgca aagatacctc cctggggcgt ccggtgcgca 300
atgttaaatg ctatatcttg aaccctagcc tgaaacgcgt gccaattggc atgcgaacac 360
atgaccctgc gacctgctgg agactgtaaa caatcactt 399

<210> SEQ ID NO 163
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 163
tcatttcgag aaaaggccga cagcaggtcg cagggtcatg tgttcgcagt ggaacgagta 60
cggtttcacc gagtctgcgt tcgtgactgc gctgaaaatt ttcgatccgg aaagcacccg 120
caaagatacc tccctggggc gtccggtgcg caatgttaaa tgctatatct tgaaccctag 180
cctgaaacgc gtgccaattg gtgctacagg tgagctgcat attggcggcc tgggtatctc 240
caagggttac ttgaatcgtc cggaactgac gccgcaccgc ttcatcccga acccgtttca 300
gaccgattgc gaaaaacagc tgggtatcaa ctctctgatg tacaaaaccg gcactgtcag 360
cctgcattag tcggtgctgc tgcaaaataa gggaaagaac cc 402

<210> SEQ ID NO 164
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 164
aacgaggata tacaaatata cagcagcaaa ggtgccatgt gtggctcttc ttgaatcgtc 60
cggaactgac gccgcaccgc ttcatcccga acccgtttca gaccgattgc gaaaaacagc 120
tgggtatcaa ctctctgatg tacaaaaccg gtgatctggc tcgctggctc ccgaacggtg 180
aagttgaata cctgggccgt gcggatttcc agatcaaact gcgcggtatt cgtattgagc 240
cgggcgaaat cgagactatg ctggcgatgt atccgcgcgt tcgtacctcc ctggtggttt 300
ccaagaaatt acgtaacggt cctgaagaaa caacgaacga acacctggta gagaagagcg 360
accgctaaga tgccctctgc tgatatacca ctctcaacac tt 402

<210> SEQ ID NO 165
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 165
atggagcttt tatgtggtta cagcagagga catcttagcg gtcgctcttc tcggatttcc 60
agatcaaact gcgcggtatt cgtattgagc cgggcgaaat cgagactatg ctggcgatgt 120
atccgcgcgt tcgtacctcc ctggtggttt ccaagaaatt acgtaacggt cctgaagaaa 180
caacgaacga acacctggta ggctactacg tatgcgactc cgcatctgtt tccgaagcgg 240
atctgctgtc cttcctggag aagaagctgc cgcgttatat gattccgact cgtctggtac 300
agctgagcca gatcccggtt aacgtcaacg gtaaagccga tctgcgtgct cagaagagcc 360
acacatggca cctttgctgc tgaacaacga aactagacaa tt 402

<210> SEQ ID NO 166
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 166
tgattatggt ggttgcggtg cagcagcacc gactaatgca ggctggcagt gttcctggag 60
aagaagctgc cgcgttatat gattccgact cgtctggtac agctgagcca gatcccggtt 120
aacgtcaacg gtaaagccga tctgcgtgct ctgccggcgg ttgatatctc caacagcacc 180
gaagttcgtt ctgatctgcg tggtgatacc gaaattgccc tcggcgaaat ctgggcggac 240
gtgctgggcg cgcgtcagcg ttcggttagc cgtaacgata actttttccg cctcggtggc 300
cactctatca cctgcatcca gctgattgcg cgtatccgtc agcgtcagcg tcactgcgaa 360
cacatgaccc tgcgacctgc tgcagaataa ctaaattagt at 402

<210> SEQ ID NO 167
<211> LENGTH: 439
<212> TYPE: DNA
<213> ORGANISM: Artificial Sequence
<220> FEATURE:
<223> OTHER INFORMATION: Synthetic nucleotide

<400> SEQUENCE: 167
tatttttttc caatttttta cagcagcacc gactaatgca ggctggcaac ctgcatccag 60
ctgattgcgc gtatccgtca gcgtcagcgt ttgtctgtgt ctatctctgt ggaagacgtg 120
tttgctacac gcactcttga gcgtatggcc gacctgttgc aaaacaaaca gcaagagaaa 180

```
tgcgacaaac cacacgaagc accgactgaa ctgcttgaag aaaacgctgc gactgataac    240

atctacctgg cgaacagcct gcagcaaggt ttcgtctacc attacctgaa aagcatggaa    300

caaagtgatg cttatgtaat gcagagcgtt ctgcgttaca acaccaccct ttcccggatc    360

tgttccagcg tgcctggaaa cacgcgcagc ctgcgaacac atgaccctgc gacctgctgg    420

caacagaata gcagaggat                                                 439


<210> SEQ ID NO 168
<211> LENGTH: 413
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<222> LOCATION: (282)..(282)
<223> OTHER INFORMATION: n is a, c, g, or t

<400> SEQUENCE: 168

ctaatttgaa tgcagtccgt cagcagcacc gactaatgca ggctggcagt aagcatggaa     60

caaagtgatg cttatgtaat gcagagcgtt ctgcgttaca acaccaccct ttccccggat    120

ctgttccagc gtgcctggaa acacgcgcag caaagcttcc cggctctgcg tctgcgcttc    180

tcttgggaaa aagaagtctt ccagctgctg ggatcaggac ccgcctctgg actggcgttt    240

cctctacttc actgatgtgg tggcaggtgc agatccccgt tntcagtcgg gcgaaccagt    300

gacagctggg tatcttcgtt gatgcctcag cgctcagttc ggacagctga cgcagaaggt    360

acactgcgaa cacatgaccc ttcgacctgc ttggtttttt ccaaaggtaa tgt           413


<210> SEQ ID NO 169
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 169

ttaagtatga ttaatgctgt cagcagcacc gactaatgca ggctggcgtg caaagcttcc     60

cggctctgcg tctgcgcttc tcttgggaaa aagaagtctt ccagctgctg gatcaggacc    120

cgcctctgga ctggcgtttc ctctacttca ctgatgtggc ggctggtgca gtagaagacc    180

gtaaactgga agatttacgc caccaggacc tcaccgagcg ttttaaactg gatgtgggcc    240

gtctgtttcg cgtttacctg atcaaacaca gcgaaaaccg tttcacttgt ctgttctctt    300

gtcacccgct atcctggacg gctggtcctt accgcttctg ttcgaaaacc ctgcgaacac    360

atgaccctgc gacctgctga catattatga acaatatcg                           399


<210> SEQ ID NO 170
<211> LENGTH: 401
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
```

<400> SEQUENCE: 170
gtggtatgca cgttggtcct cagcagcacc gactaatgca ggctggcagt ccaaagcttc 60
ccggctctgc gtctgcgctt ctcttgggaa aaagaagtct tccagctgct ggatcaggac 120
ccgcctctgg actggcgttt cctctacttc actgatgtgg cgctggtgca gtagaagacc 180
gtaaactgga agatttacgc cgccaggacc tcaccgagcg ttttaaactg gatgtgggcc 240
gtctgtttcg cgtttacctg atcaaacaca gcgaaaaccg tttcacttgt ctgttctctt 300
gtcaccacgc tatcctggac ggctggtcct taccgcttct gttcgaaaaa cnctgcgaac 360
acatgaccct gcgacctgct gaaacggnga tcactcacat a 401

<210> SEQ ID NO 171
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 171
attacttagg gtattgcgtt cagcagcacc gactaatgca ggctggcagg cgtttacctg 60
atcaaacaca gcgaaaaccg tttcacttgt ctgttctctt gtcaccacgc tatcctggac 120
ggctggtcct taccgcttct gttcgaaaaa gtacacgaaa catacctgca actgctgcac 180
ggcgataacc tgacctcctc tatggatgat ccatacaccc gtacccaacg ctacctgcat 240
gcgcaccgcg aagatcacct cgacttttgg gctggcgtgg tgcagaaaat caacgaacgt 300
tgcgatatga atgctctgtt aaacgaacgc agccgctata aagtgcagct cactgcgaac 360
acatgaccct gcgacctgct gatcgcaaag actgaaggtc t 401

<210> SEQ ID NO 172
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 172
atagcgttat taatttctgt cagcagaggg catcttaggg gtcgctcttc taagatcacc 60
tcgacttttg ggctggcgtg gtgcagaaaa tcaacgaacg ttgcgatatg atgctctgtt 120
aaacgaacgc agccgctata aagtgcagct ggccgactac gatcaggtac aggaacagcg 180
tcagctgacg atcgctctga gcggtgacgc gtggctggcg gatctgcgcc agacatgcag 240
tgcgcagggc atcacgctgc actctatcct gcaatttgta tggcatgcag ttctgcatgc 300
ctacggtggc ggtactcaca ctatcactgg caccactatt tctggtcgca agaagcgcca 360
cacatggcac ctttgctgct gaggactagc cgaataacta t 401

<210> SEQ ID NO 173
<211> LENGTH: 390
<212> TYPE: DNA
<213> ORGANISM: Artificial Sequence
<220> FEATURE:
<223> OTHER INFORMATION: Synthetic nucleotide

<400> SEQUENCE: 173
tcatagagga ggtgctatgg cagcaggtcg cagggtcatg tgttcgcagt gctacggtgg 60
cggtactcac actatcactg gcaccactat ttctggtcgc aacctcccga tcctgggtat 120
cgagcgtgcg gtaggcccgt acattaacac cctgccgtta gtgttggacc attctacttt 180

-continued

```
taaagacaag acgatcatgg aagctattga agacgtccaa gcgaaggtga atgttatgaa    240

ctcccgtggt aatgtagaac tgggtcgcct gcacaaaacc gacctgaaac atggcctgtt    300

cgattctctg tttgtgctgg aaaactatcc aaacctggat aaatccagcc tgcattagtc    360

ggtgctgctg aacagtcaat aaacgatccg                                     390
```

<210> SEQ ID NO 174
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 174

```
gatatttcgc ggttctgttg cagcagcacc gactaatgca ggctggcagt agctattgaa     60

gacgtccaag cgaaggtgaa tgttatgaac tcccgtggta atgtagaact gggtcgcctg    120

cacaaaaccg acctgaaaca tggcctgttc gattctctgt ttgtgctgga aaactatcca    180

aacctggata aatcccgtac tctggagcac caaactgaac tgggttactc catcgagggt    240

ggtaccgaaa aactgaacta tccgctggcg gtgattgctc gtgaggttga gaccactggc    300

ggctttactg ttagcatctg ctatgcgagc gaactgtttg aagaggtgat cactgcgaac    360

acatgaccct gcgacctgct gagtttaagt aacctttacc t                        401
```

<210> SEQ ID NO 175
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 175

```
tagtctttgc cggtttatta cagcagcacc gactaatgca ggctggcagt gaactgaact     60

atccgctggc ggtgattgct cgtgaggttg agaccactgg cggctttact gttagcatct    120

gctatgcgag cgaactgttt gaagaggtga tgatcagcga gcttctccat atggtacagg    180

ataccctgat gcaggttgca cgcgggctca acgaacctgt gggctccctg gaatacctgt    240

cttccatcca gttagagcag ctggcagcgt ggaacgccac cgaagcggag ttcccggaca    300

cgaccctgca tgaaatgttc gagaacgaag catctcaaaa gccggataaa acactgcgaa    360

cacatgaccc tgcgacctgc tgtctgtaga atctttgcaa                         400
```

<210> SEQ ID NO 176
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 176

```
ctaaactctt tacttcctat cagcagaggg aatcttagcg gtcgctcttc tttagagcag     60

ctggcagcgt ggaacgccac cgaagcggag ttcccggaca cgaccctgca tgaaatgttc    120

gagaacgaag catctcaaaa gccggataaa attgcagtcg tgtacgaaga aacctctctg    180

acctatcgcg agctgaacga acgtgccaat cgcatggcgc accagctgcg ttccgacgtt    240

tctccgaacc cgaacgaagt gatcgcgctg gttatggaca agagtgaaca catgatcgta    300

aatatcttgg ctgtgtggaa atctggtggc gcatacgtgc cgatcgatcc gagaagatcc    360
```

-continued acacatggca cctttgctgc tgaagccaca taataacgag ct 402

<210> SEQ ID NO 177
<211> LENGTH: 372
<212> TYPE: DNA
<213> ORGANISM: Artificial Sequence
<220> FEATURE:
<223> OTHER INFORMATION: Synthetic nucleotide

<400> SEQUENCE: 177
ttatgagaaa tgtttcactg cagcagaggg catcttagcg gtcgcggaca agagtgaaca 60
catgatcgta aatatcttgg ctgtgtggaa atctggtggc gcatacgtgc cgatcgatcc 120
gggctacccg aatgaccgta ttcagtatat cctcgaggac actcaggcgt tggctgttat 180
cgcagattct tgttacctgc ctcgtatcaa aggtatggcc gcgtctggta cgctgctcta 240
cccgtctgtc ctgccggcaa acccagacag caaatggtct gtgtcaaacc cgtcgccgct 300
gtctcgtagc accgacctgg cagaagagcc acacatggca cctttgctgc tgctagattt 360
gatagtgttc ta 372

<210> SEQ ID NO 178
<211> LENGTH: 403
<212> TYPE: DNA
<213> ORGANISM: Artificial Sequence
<220> FEATURE:
<223> OTHER INFORMATION: Synthetic nucleotide

<400> SEQUENCE: 178
tttgtaattt gactctgatg cagcagaggg catcttagcg gtcgctcttc tcgtctggta 60
cgctgctcta cccgtctgtc ctgccggcaa acccagacag caaatggtct gtgtcaaacc 120
cgtcgccgct gtctcgtagc accgacctgg catacatcat ctacacctct ggcaccaccg 180
gccgcccgaa aggcgtgact gtggagcatc acggtgtggt gaacctgcag gtatccctga 240
gcaaagtttt tggtctgcgt gacaccgacg acgaagtcat cctgtctttt tctaactacg 300
ttttcgatca cttcgtagaa cagatgactg atgctatcct gaacgggcag aagaagagcc 360
acacaaggca cctttgctgc tgtgaaaagt caaaagattc cta 403

<210> SEQ ID NO 179
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 179
tactgggagc aaacaattct cagcagcacc gactaatgca ggctggcagt aggtctgcgt 60
gacaccgacg acgaagtcat cctgtctttt ctaactacgt tttcgatcac ttcgtagaac 120
agatgactga tgctatcctg aacgggcaga cgctgctggt tctgaacgat ggtatgcgtg 180
gtgacaaaga acgcctgtac cgctacatcg aaaagaaccg tgtaacttat ctgtctggta 240
ctccatctgt ggtgtctatg tatgagttca gccgtttcaa agaccacctg cgccgcgtcg 300
attgcgtcgg tgaagctttc agcgagccgg tcttcgacaa aatccgtgaa cactacgaac 360
acatgaccca gcgacctgct gagtgaaaac agcagacgaa 400

<210> SEQ ID NO 180
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 180
gtgggatgga agctcctcga cagcagaggg catcttagcg gtcgctctct accttccacg 60
gtttggttat caatggttat ggcccaactg aagttagcat cactacccat aagcgtttat 120
accctttccc agagcgccgc atggataagt cgatcggcca gcaggtccac aactctacta 180
gctacgtact gaatgaagat atgaagcgta ccccgatcgg tgctgtgggt gagctgtacc 240
tgggcggtga aggtgttgtc cgcggttatc ataatcgtgc ggtgttaccg ccgagcgctt 300
catcccgaac ccgttccagt ctgaggaaga taaacgtgaa ggccgtaaca gaagaaccac 360
acatggcacc tttgctgctg gcaaaaagga cataataca 399

<210> SEQ ID NO 181
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 181
ttgttggata tatagggtta caaaagaggg catcttagcg gtcgctcttc tcgatcggcc 60
agcaggtcca caactctact agctacgtac tgaatgaaga tatgaagcgt accccgatcg 120
gtgctgtggg tgagctgtac ctgggcggtg aaggtgttgt ccgcggttat cataatcgtg 180
cggatgttac cgccgagcgc ttcatcccga acccgttcca gtctgaggaa gataaacgtg 240
aaggccgtaa cagtcgcctg tacaagacgg gtgatctggt tcgctggatc ccgggtagct 300
ccggcgaagt cgaatacctg ggtcgcaatg acttccaggt taagattcgc gagaagaacc 360
acacatggca cctttgctgc tgaagtacac atcatcccca tg 402

<210> SEQ ID NO 182
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 182
aattcactca gaataatttt cagcagcaaa ggtgccttgt gtggctctct cggcgaagtc 60
gaatacctgg gtcgcaatga cttccaggtt aagattcgcg gcctccgtat cgagctgggt 120
gaaatcgaag cgatcctgag cagctaccac ggcattaaac agagcgtagt gatcgcaaaa 180
gactgccgtg agggggcaca gaaattcctg gtcggctatt acgttgcaga cgctgccctg 240
ccgtccgcag cgatccgtcg tttcatgcag tcgcgcctcc cgggttacat ggttccgtcc 300
cgtctgatcc tggtttctaa attccctgtt actccgtccg ggaagctgga agaagagcga 360
ccgctaagat gccctctgct ggagattaat tccaactaaa t 401

<210> SEQ ID NO 183
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 183
ctactgttcg ttcccaatta cagcagaggg catcttagcg gtcgctcttc tcgtctgatc 60

-continued ctggtttcta aattccctgt tactccgtcc gggaagctgg acaccaaagc actgccgccg 120
gcggaggaag aaagcgaaat cgacgttgtt ccaccgcgct ccgaaattga gcgttctctc 180
tgcgacatct gggctgaact gctggaaatg cacccggaag aaatcggcat ttactctgac 240
ttcttctcct tgggcggcga cagcctgaaa tctactaagt tatccttcat gatccatgag 300
tcctttaacc gtgctgtgag cgttagcgcg ttattctgcc atcgcacagt tagaagagcc 360
acacatggca cctttgctgc tgttccccca gttttacacc aa 402

<210> SEQ ID NO 184
<211> LENGTH: 371
<212> TYPE: DNA
<213> ORGANISM: Artificial Sequence
<220> FEATURE:
<223> OTHER INFORMATION: Synthetic nucleotide

<400> SEQUENCE: 184
atgtgttata gaagttgttg cagcagaggg catcttagcg gtcctaagtt atccttcatg 60
atccatgagt cctttaaccg tgctgtgagc gttagcgcgt tattctgcca tcgcacagtt 120
gaagctcaaa ctcacctgat cttgaacgac gcagcagatg tacacgaaat taccccgatc 180
gattgcaacg acacccagat gatcccggtt tcccgtgcac aggaacgtct gctgttcatt 240
catgaattcg aaaacggttc taacgcttac aacattgacg cggctttcga actgccaggt 300
tctgtggacg cgagcctgct agaagagcca cacatggcac ctgtgctgct gagcagggat 360
aacacatgtc a 371

<210> SEQ ID NO 185
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 185
tttcagaaac ttaaacttac cagcagaggg catcttagcg gtcgctcttc tgaagctcaa 60
actcacctga tcttgaacga cgcagcagat gtacacgaaa ttaccccgat cgattgcaac 120
gacacccaga tgatcccggt ttcccgtgca caggaacgtc tgctgttcat tcatgaattc 180
gaaaacggtt ctaacgctta caacattgac gcggctttcg aactgccagg ttctgtggac 240
gcgagcctgc tggaacaggc ccttcgtggc aacctggcac gtcacgaagc actgcgcacc 300
ctgctggtta aagatcacgc cactggtatt tacctgcaga aagtactgaa tagaagagcc 360
acacatggca cctttgctgc tgattcctat tacttcttat aa 402

<210> SEQ ID NO 186
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 186
tatacaatct attggtaatc cagcagaggg catcttagcg gtcgctcttc taggaacgtc 60
tgctgttcat tcatgaattc gaaaacggtt ctaacgctta caacattgac gcggctttcg 120
aactgccagg ttctgtggac gcgagcctgc tggaacaggc ccttcgtggc aacctggcac 180
gtcacgaagc actgcgcacc ctgctggtta aagatcacgc cactggtatt tacctgcaga 240
aagtactgag tccggacgaa gcgcaaggta tgttttctgt taatgtagat actgctaaac 300
aggttgaacg tctggatcag gaaattgctt ctctgtctca gcacgtcttc cagaagagcc 360
acacatggca cctttgctgc tggaaaggat taaagtattc ca 402

<210> SEQ ID NO 187
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 187
ttacatgctt tcgacacata cagcaggtcg cagggtcatg tgttcgcagt gggttgaacg 60
tctggatcag gaaattgctt ctctgtctca gcacgtcttc cgcctggacg acgaactgcc 120
gtgggaggcg cgcatcctga aactggaatc tggcggtctg tacctgatct tggccttcca 180
ccacacctgc ttcgatgcat ggagcctgaa agttttcgaa caggagctgc gcgcgctgta 240
cgcagcgctt cagaaaacga aatctgcagc gaacttaccg gcattaaaag cacagtataa 300
ggaatacgct ctgtaccacc gccgccagct tagcggcgac cgcatgcgta acacagccag 360
cctgcattag tcggtgctgc tgaaagatcc tcacactata ca 402

<210> SEQ ID NO 188
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 188
gttaatttct ggggatacgt cagcagaggg catcttagcg gtcgttcttc tgaatacgct 60
ctgtaccacc gccgccagct tagcggcgac cgcatgcgta acctgtccga tttctggtta 120
cgtaaactga tcggtctgga accactgcag ctgatcaccg atcgtccgcg tccggttcag 180
ttcaaatacg acggtgacga tctgagcatc gaactgtcca agaaagagac cgaaaacctg 240
cgcggcgttg caaaacgttg taagtcttcc ttatatgttg tactggtatc tgtttactgt 300
gtcatgctgg caagctacgc caaccagagc gatgttagcg tgggcatccc aagaagacca 360
cacatgtcac ctttgctgct gcttataaaa agcgtgagtt a 401

<210> SEQ ID NO 189
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 189
tacctgtgat ctgcgtcgta cagcagaggg catcttagcg gtcgctcttc ttgatcaccg 60
atcgtccgcg tccggttcag ttcaaatacg acggtgacga tctgagcatc gaactgtcca 120
agaaagagac cgaaaacctg cgcggcgttg caaaacgttg taagtcttcc ttatatgttg 180
tactggtatc tgtttactgt gtcatgctgg caagctacgc caaccagagc gatgttagcg 240
tgggcatccc agtatcacac cgtacgcacc cgcagttcca gtctgttatc ggctttttcg 300
ttaacctggt cgttctgcgt gtagatatca gccagtccgc tatttgcggt tagaagagcc 360
acacatggca cctttgctgc tgtcttcatc gataaataca aa 402

<210> SEQ ID NO 190

<211> LENGTH: 397
<212> TYPE: DNA
<213> ORGANISM: Artificial Sequence
<220> FEATURE:
<223> OTHER INFORMATION: Synthetic nucleotide

<400> SEQUENCE: 190
gaagcacctg tcttatttaa cagcagcacc gactaatgca ggctggcatg aaaacgttgt 60
aagtcttcct tatatgttct ggtatctgtt tactgtgtca tgctggcaag ctacgccacc 120
agagcgatgt tagcgtgggc atcccagtat cacaccgtac gcacccgcag ttccagtctg 180
ttatcggctt tttcgttaac ctggtcgttc tgcgtgtaga tatcagccag tccgctattt 240
gcggtttaat ccgtcgcgtc atgaaagaac tggttgacgc gcagctgcac caggatatgc 300
cgttccagga agttacgaaa ctgctgcagg tggataacga tcctagcact gcgaacacat 360
gaccctgcga cctgctgaag cctacccggg aagatca 397

<210> SEQ ID NO 191
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 191
tcatcctatt acgatgcccg cagcagcaaa ggtgccatgt gtggctcttt atgccgttcc 60
aggaagttac gaaactgctg caggtggata acgatcctag ccgtcacccg ttggttcaga 120
acgtatttaa ctttgagtct cgcgcgaacg gtgaacacga tgcccgctct gaagacgagg 180
gctctcttgc attcaatcag taccgtccgg ttcagccggt tgacagcgtg gccaaattcg 240
atctgaacgc caccgtcacc gaactggaat ccggtctgcg tgttaatttc aactacgcga 300
ccagcttatt caataaatcc accatccagg gcttcctgca cacatatgaa agaagaggac 360
cgctaagatg ccctctgctg caataaaaag cttccaacgc 400

<210> SEQ ID NO 192
<211> LENGTH: 400
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<222> LOCATION: (395)..(395)
<223> OTHER INFORMATION: n is a, c, g, or t

<400> SEQUENCE: 192
atttataagg acgggccagc cagcagaggg catcttagcg gtcgctcttc tccagcttat 60
tcaataaatc caccatccag ggcttcctgc acacatatga ataccttctg cgtcagctgt 120
ccgaactgag cgctgaaggc atcaacgaag atacccagct gtcactggtt cgcccgactg 180
agaacgggga tctgcacctg ccactggccc agtctccgct cgcgaccact gcagaagaac 240
agaaagttgc ttccctgaac caggctttcg aacgtgaagc cttcctggcg gcggaaaaaa 300
tcgccgttgt tcaaggggac cgcgctctgt cgtatgccga cctgaacggt cagaaaccac 360
acatggcacc tttgctgctg taccaatacg gggancgttt 400

<210> SEQ ID NO 193
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 193

```
taatctgatc gatgctagga cagcaggtcg cagggtcatg tgttcgtagt gcgccgttgt     60

tcaaggggac cgcgctctgt cgtatgccga cctgaacggt caggctaatc aactggcgcg    120

ttatatccag tccgtctcct gcatcggtgc cgacgacggc atcgccctga tgctggaaaa    180

gagcatcgat actatcatct gcattctggc aatctggaaa gcaggcgccg cgtatgtgcc    240

gctggatccg acctacccac caggccgtgt acaactgatc ctggaggaaa tcaaagcgaa    300

agctgtgctg gtacactctt cccacgcctc taaatgtgaa cgtcacggtg ccactgccag    360

cctgcattag tcggtgctgc tgttaggagg attgaatcaa aa                       402
```

<210> SEQ ID NO 194
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 194

```
tagccctttt cgtatttgca tcagcagcaa aggtgccatg tgtggctctt tcctacccac     60

caggccgtgt acaactgatc ctggatgaaa tcaaagcgaa actgtgctgg tacactcttc    120

cacgcctcta aatgtgaacg tcacggtgcc aaagtcattg cagtagactc tccggctatt    180

gaaacggcag tgagccagca gtctgcagct gatctgccga ccattgctag cctgggtaat    240

ctggcatata tcatctttac tagcggcact tctggcaaac cgaaaggcgt tctggtagag    300

caaaaagccg ttctgctgct gcgcgacgcc ctgcgtgagc gttacttcga gaagagcgac    360

cgctaagatg ccctctgctg tagactgagt tgaacaacta                           400
```

<210> SEQ ID NO 195
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 195

```
atcattgcac ttgttgttcg cagcagcaaa ggtgccatgt gtggctcttc tatcatcttt     60

actagcggca cttctggcaa accgaaaggc gttctggtag agcaaaaagc cgttctgctg    120

ctgcgcgacg ccctgcgtga gcgttacttc ggtcgtgatt gtaccaaaca tcacggtgtt    180

ctgttcctga gcaactacgt tttcgacttc tccgtagaac agctggttct gtctgtactc    240

tcaggccaca aactgattgt cccgccggcg gagtttgtgg cggatgacga attctatcgt    300

atggcctcta cccacggtct ttcttacctg tctggcaccc cgagcctgct tagaagagcg    360

accgctaaga tgccctctgc tgaaatcagt aaaaaacctt cc                       402
```

<210> SEQ ID NO 196
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 196

```
ttattcgtgg attggtgttc cagcagaggg catcttagcg gtcgctcttc tttcgacttc     60
```

-continued

```
tccgtagaac agctggttct gtctgtactc tcaggccaca aactgattgt cccgccggcg    120

gagtttgtgg cggatgacga attctatcgt atggcctcta cccacggtct ttcttacctg    180

tctggcaccc cgagcctgct tcaaaaaatc gatctggcac gtctggatca cctgcaggtt    240

gtaaccgcgg cgggtgagga actccacgcg acccagtacg aaaaaatgcg tcgtcgtttt    300

aacggtccaa tctacaacgc ttatggtgtt accgagacaa cggtgtacaa cagaagaacc    360

acacatggca cctttgctgc tgtaatcaga acctagaaaa at                        402
```

<210> SEQ ID NO 197
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 197

```
tgatttcacc actaagtctc agcaggtcgc agggtcatgt gttcgcagtg acggtccaat     60

ctacaacgct tatggtgtta ccgagacaac ggtgtacaac atcatcgctg aattcaccac    120

caactccatc ttcgaaaacg cattacgcga agtcctgccg ggcacccgtg cgtacgttct    180

gaacgcggcg ctgcagccgg ttccattcga cgctgtgggt gaactgtatc tggccggcga    240

tagcgtaacc cgtggttacc tgaaccagcc gttgctgacc gatcagcgtt tcatccctaa    300

cccgttctgc aaggaagaag acatcgcgat gggtcgtttc gctcgtctgt cacgccagcc    360

tgcattagtc ggtgctgctg gcacgagaaa taaaggagg                           399
```

<210> SEQ ID NO 198
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 198

```
taaagttatc atgtgctacc cagcagcaaa ggtgccatgt gtggctcttc tacaaaaccg     60

gcgacctggt tcgctctcgc ttcaaccgcc agcagcagcc gcagctggaa tacctgggcc    120

gtggcgacct gcagattaaa atgcgtggtt accgcattga aattagcgaa gtacagaacg    180

tgctgacctc ctccccgggc gtacgcgaag gtgcggttgt ggctaaatat gaaaacaacg    240

acacgtatag ccgtactgca cattccttag tcggttatta taccactgat aacgaaacag    300

tttcagaagc tgatatcctc accttcatga aagcgcgtct gccgacctat aagaagagga    360

ccgctaagat gccctctgct ggagatgaat ataggtttac a                        401
```

<210> SEQ ID NO 199
<211> LENGTH: 399
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<222> LOCATION: (394)..(394)
<223> OTHER INFORMATION: n is a, c, g, or t

<400> SEQUENCE: 199

```
gttcattgca taatgcttct cagcagcacc gactaatgca ggctggagtg ttccattcga     60

cgctgtgggt gaactgtatc tggccggcga tagcgtaacc cgtggttacc tgaaccagcc    120

gttgctgacc gatcagcgtt tcataactaa cccgttctgc aaggaagaag acatcgcgat    180
```

```
gggtcgtttc gctcgtctgt acaaaaccgg cgacctggtt cgctctcgct tcaaccgcca    240

gcagcagccg cagctggaat acctgggccg tggcgacctg cagattaaaa tgcgtggtta    300

ccgcattgaa attagcgaag tacagaacgt gctgacctcc tcccgggcgc atgcgaacac    360

atgaccctgc gacctgctgc tggatgtaaa gggntttaa                           399


<210> SEQ ID NO 200
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 200

attgatatgt aagagatttc cagcagcaaa ggtgccatgt gtggctctta tcgtactgca     60

cattccttag tcggttatta taccactgat aacgaaacag tttcagaagc tgatatcctc    120

accttcatga aagcgcgtct gccgacctat atggtgcctt ctcacctgtg ctgcctggaa    180

ggtgctctgc cagtcactat taacggtaaa ctggacgttc gtcgtctgcc tgaaattatc    240

aacgacagtg cgcaatcctc atattccccg ccgcgcaaca ttatcgaagc gaaaatgtgc    300

cgtttatggg aaagcgcgct gggtatggaa cgctgcggta ttgacgatga cagaagagcg    360

accgctaaga tgccctctgc tgaacgaaaa tggtacctat t                        401


<210> SEQ ID NO 201
<211> LENGTH: 398
<212> TYPE: DNA
<213> ORGANISM: Artificial Sequence
<220> FEATURE:
<223> OTHER INFORMATION: Synthetic nucleotide

<400> SEQUENCE: 201

gattactaca tttttctcaa cagcagcacc gactaatgca ggctggcagt gaacggtaaa     60

ctggacgttc gtcgtctgcc tgaaattatc aacgacagtg cgaatcctca tattccccgc    120

cgcgcaacat tatcgaagcg aaaatgtgcg tttatgggaa agcgcgctgg gtatggaacg    180

ctgcggtatt gacgatgacc tcttcaagct ggggggggat tctatcacca gtctgcacct    240

cgtcgcacag attcacaatc aggtgggctg taagattacc gtgcgcgata ttttcgaaca    300

ccgtaccgcg cgtgctctcc acgatcacgt tttcatgaag gatagcgatc atgcgaacac    360

atgaccctgc gacctgctgg cccaaccccc cccaaaag                            398


<210> SEQ ID NO 202
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 202

aattggttac ctctatcccc cagcagcaaa ggtgccatgt gtggctcttc taccgtaccg     60

cgcgtgctct ccacgatcac gttttcatga aggatagcga tcgctctaac gtcacccagt    120

tccgtaccga gcaggggccg gtcattggcg aagctccgct gctgccgatc caggattggt    180

tcttgagcaa agctctgcag caccctatgt actggaacca cacgttctac gtacgtaccc    240

cggaactgga cgttgattcc ctgagtgcgg ccgttcgtga cctgcagcag taccacgacg    300

ttttccgcat gcgcctgaaa cgcgaagaag ttggctttgt acagtccttt gagaagagcg    360
```

-continued accgctaaga tgccctctgc tgaaatcgga tcccagtatg ag 402

<210> SEQ ID NO 203
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 203
gcataaagcg ggaggcttct cagcagaggg catcttagcg gtcgctcttc ttttccgcat 60
gcgcctgaaa cgcgaagaag ttggctttgt acagtccttt gccgaagact tttccccggc 120
gcagctgcgt gtactgaacg tgaaggacgt ggatggtagc gcggcggtta acgaaatcct 180
ggacggttgg caaagcggct tcaacctgga aaacggtccg atcggctcga tcggttatct 240
gcatggctat gaagaccgct ccgcacgtgt gtggttttct gtacaccaca tggccattga 300
cactgtttcc tggcagatcc tggttcgtga tctgcagact ctgtaccgta aagaagaacc 360
acacatggca cctttgctgc tggcactatt ctatgacaca g 401

<210> SEQ ID NO 204
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 204
tttcgaccga tttcagtctg cagcaggtcg cagggttatg tgttcgcagt gcaacctgga 60
aaacggtccg atcggctcga tcggttatct gcatggctat gaagaccgct ccgcacgtgt 120
gtggttttct gtacaccaca tggccattga cactgtttcc tggcagatcc tggttcgtga 180
tctgcagact ctgtaccgta acggttccct gggttccaaa ggttcttcat ttcgccaatg 240
ggccgaggca atccaaaact acaaagcgag cgactcggaa cgtaaccatt ggaacaagct 300
ggttatggaa actgcatcgt cgatcagcgc gctgccgacc tccactggtt ccactaccag 360
cctgcattag tcggtgctgc tgtaattacc gtcaaaaaa 399

<210> SEQ ID NO 205
<211> LENGTH: 400
<212> TYPE: DNA
<213> ORGANISM: Artificial Sequence
<220> FEATURE:
<223> OTHER INFORMATION: Synthetic nucleotide

<400> SEQUENCE: 205
cttcctgtgg gttttctaca gcagcaaagg tgccatgtgt ggctcttctt ccaaaactac 60
aaagcgagcg actcggaacg taaccattgg aacaagctgg ttatggaaac tgcatcgtcg 120
atcagcgcgc tgccgacctc cactggttct cgcgtacgtc tctcccgttc tctgtctcct 180
gaaaaaactg cttctctgat ccagggtggc atcgatcgtc aggatgtaag cgtatacgat 240
tctctgctga cttctgttgg cctggctttg caacacatcg cgccgactgg cccgtctatg 300
gttacaatcg agggtcacgg ccgcgaagaa gttgaccaga ccctggatga gaagagcgac 360
cgctaagatg ccctctgctg aatacgcgaa tgatgtaaaa 400

<210> SEQ ID NO 206
<211> LENGTH: 399
<212> TYPE: DNA
<213> ORGANISM: Artificial Sequence
<220> FEATURE:
<223> OTHER INFORMATION: Synthetic nucleotide

<400> SEQUENCE: 206
tttttgagct acgctttcgg cagcagcaaa ggtgccatgt gtggctcttc tacttctgtt 60
ggcctggctt tgcaacacat cgcgccgact ggcccgtcta tggttacaat cgagggtcac 120
ggccgcgaag aagttgacca gaccctggat gtttctcgta cgatgggctg gttcactacc 180
atgtatccgt tcgaaatccc gcgtctgtcg acggaaaaca tcgtgcaggg tgttgttgct 240
gtaagtgaac gcttccgcca agttccggct cgcggtgttg gttatggtac tctgtacggt 300
tacacccagc accctctgcc gcaggttact gttaactacc tgggccagct gagaaggacc 360
gctaagatgc cctctgctgc tgaaagtaga atgtattga 399

<210> SEQ ID NO 207
<211> LENGTH: 401
<212> TYPE: DNA
<213> ORGANISM: Artificial Sequence
<220> FEATURE:
<223> OTHER INFORMATION: Synthetic nucleotide

<400> SEQUENCE: 207
gtcagtagta taccgttcgt cagcagaggg catcttagcg gtcgctcttc tacacccagc 60
accctctgcc gcaggttact gttaactacc tgggccagct ggctcgtaaa cagagcaagc 120
cgaaagaatg ggttctggca gttggtgata acgagttcga gtacggtctg atgacctccc 180
cggaggataa ggaccgttcg agctccgcag tggatgttac ggccgtctgc atcgacggga 240
cgatgatcat cgatgtggac tcggcttggt ctttggaaga atctgaacag ttcatctcgt 300
caattgaaga aggtctgaac aaaatcctgg acggtcgtgc atcccagcag aagaaagcca 360
cacatggcac ctttgctgct gaggaaggca atcttagatc g 401

<210> SEQ ID NO 208
<211> LENGTH: 403
<212> TYPE: DNA
<213> ORGANISM: Artificial Sequence
<220> FEATURE:
<223> OTHER INFORMATION: Synthetic nucleotide

<400> SEQUENCE: 208
ttctgcagaa cgtttttgta acagcagcaa aggtgccatg tgtggctctt ctgctcgtaa 60
acagagcaag ccgaaagaat gggttctggc agttggtgat aacgagttcg agtacggtct 120
gatgacctcc ccggaggata aggaccgttc gagctccgca gtggatgtta cggccgtctg 180
catcgacggg acgatgatca tcgatgtgga ctcggcttgg tctttggaag aatctgaaca 240
gttcatctcg tcaattgaag aaggtctgaa caaaatcctg gacggtcgtg catcccagca 300
gactagccgc tttccggatg tgccgcagcc agcagagacc tacaccccat acagaagagt 360
gaccgctaag atgccctctg ctggatgggc cataataccg tcg 403

<210> SEQ ID NO 209
<211> LENGTH: 402
<212> TYPE: DNA
<213> ORGANISM: Artificial Sequence
<220> FEATURE:
<223> OTHER INFORMATION: Synthetic nucleotide

<400> SEQUENCE: 209
atcttttatg tactttgtga cagcagaggg catcttagcg gtcgctcttc tgatgtggac 60
tcggcttggt ctttggaaga atctgaacag ttcatctcgt caattgaaga aggtctgaac 120
aaaatcctgg acggtcgtgc atcccagcag actagccgct ttccggatgt gccgcagcca 180
gcagagacct acaccccata cttcgaatat ctggaaccgc cgcgccaggg cccgaccctg 240
tttctgctgc caccgggtga aggtggtgcg gaatcttact tcaacaacat cgtcaaacgc 300
ttgcgtcaaa ctaacatggt tgtctttaac aactactacc tgcactccaa aagaagagcc 360
acacatggca cctttgctgc tgacactaaa agtgttgaaa aa 402

<210> SEQ ID NO 210
<211> LENGTH: 398
<212> TYPE: DNA
<213> ORGANISM: Artificial Sequence
<220> FEATURE:
<223> OTHER INFORMATION: Synthetic nucleotide

<400> SEQUENCE: 210
taatttcctg tgcaactcag cagcaaaggt gccatgtgtg gctcttcttt cgaatatctg 60
gaaccgccgc gccagggccc gaccctgttt ctgctgccac cgggtgaagg tggtgcggaa 120
tcttacttca acaacatcgt caaacgcttg cgtcaaacta acatggttgt ctttaacaac 180
tactacctgc actccaaacg tctgcgcacc ttcgaggaac tggctgaaat gtatctggac 240
caggtacgcg gcatccaacc gcacggtcca taccacttca tcggctggag cttcgggggc 300
attctggcga tggagatgtc ccgtcgtctg gttgcgagcg acgaaaaaga agagcgaccg 360
ctaagatgcc ctctgctgac ccaaagaaat aaacaaga 398

<210> SEQ ID NO 211
<211> LENGTH: 379
<212> TYPE: DNA
<213> ORGANISM: Artificial Sequence
<220> FEATURE:
<223> OTHER INFORMATION: Synthetic nucleotide

<400> SEQUENCE: 211
atgtatcctc gctctttaac cagcatcacc gactaatgca ggctggcagt ggcattctgg 60
cgatggagat gtcccgtcgt ctggttgcga gcgacgaaaa attggtttct gggtattatc 120
gacacctatt tcaacgtacg tggtgccact cgcaccattg gccttggtga tactgaaatc 180
ctggatccga tccaccacat ctataacccg gacccggcaa actttcagcg tctgccgtct 240
gccaccgacc gtatcgtcct gtttaaggcc atgcgtccga ataataaata tgaatcagaa 300
accagcgtcg cctgtatgag tactacgaca ctgcgaacac atgaccctgc gacctgctga 360
gtaataatca aaccgggtg 379

<210> SEQ ID NO 212
<211> LENGTH: 392
<212> TYPE: DNA
<213> ORGANISM: Artificial Sequence
<220> FEATURE:
<223> OTHER INFORMATION: Synthetic nucleotide

<400> SEQUENCE: 212
ctaacgcatt gtcaggtttc cagcagcacc gactaatgca ggctggcagt gcgtatcgtc 60
ctgtttaagg ccatgcgtcc gaataataaa tatgaatcag aaaaccagcg tcgccctacg 120
acgcgttaga ttccacggac tggaccgcat gttaccaggc gatccctacc tcctcatggt 180
cgcgcctgcg cacgatccac accttcccgg gttcggaaat ccacaaccgc tggtcccgtt 240
gcgttcgtct gagccgtaac accagccttg ccatcgaccc gtctctggca gctcagtaca 300
tcggtcgttg gaagtaagca gagtaaagac cgtgcactta tcactggaac acatgaccct 360
gcgacctgct gttctacact ggtatccgga gt 392

<210> SEQ ID NO 213
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 213
atgacccaat tgaagccgcc taacgggacc actccgatcg gcttcagcgc cactactagc 60
ctgaacgcta gcggctcttc ctcggttaag aatggtacca tcaagccttc gaatggtatc 120
ttcaaacctt ctactcgtga caccatggac ccgtgctcgg gcaacgccgc tgacggctcc 180
attcgcgtac gttttcgcgg tggcatcgaa cgttggaaag agtgtgtaaa ccaagtgccg 240
gagcgttgcg acctgtctgg tctgaccacg gacagcaccc gctaccagct ggcttcga 298

<210> SEQ ID NO 214
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 214
ctgtctggtc tgaccacgga cagcacccgc taccagctgg cttcgaccgg cttcggcgac 60
gcgagcgcgg cttaccagga acgtctgatg actgtgccgg tagatgttca tgctgcgctc 120
caggagctgt gcctggaacg ccgcgtctct gtgggttctg tgatcaactt cagcgttcac 180
cagatgctga agggttttgg caacggtact cacactatca ccgcgagcct gcaccgcgaa 240
cagaatctgc agaactcctc tccgtcttgg gtcgtttccc ctactatcgt gacccatg 298

<210> SEQ ID NO 215
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 215
aacggtactc acactatcac cgcgagcctg caccgcgaac agaatctgca gaactcctct 60
ccgtcttggg tcgtttcccc tactatcgtg acccatgaaa accgcgatgg ctggtcagtg 120
gcgcaggcag tggagtctat cgaggctggt cgtggctccg aaaaggaatc tgtgaccgcg 180
attgattccg gctcctccct ggtcaaaatg ggtctgttcg atctgctggt ttccttcgtc 240
gatgcggatg acgcgcgtat cccttgcttc gactttccgc tggctgttat tgtgcgc 297

<210> SEQ ID NO 216
<211> LENGTH: 166
<212> TYPE: DNA
<213> ORGANISM: Artificial Sequence
<220> FEATURE:
<223> OTHER INFORMATION: Synthetic nucleotide

<400> SEQUENCE: 216
tgacgcgcgt atcccttgct tcgactttcc gctggctgtt attgtgcgcg agtgcgatgc 60
aaacctgtct ctcacccttc gcttctcgga ctgcctgttc aacgaggaaa ccatttgtaa 120
tttcacggat gccctcaata tcctgttggc tgaggcagtt atcggt 166

<210> SEQ ID NO 217
<211> LENGTH: 178
<212> TYPE: DNA
<213> ORGANISM: Artificial Sequence
<220> FEATURE:
<223> OTHER INFORMATION: Synthetic nucleotide

<400> SEQUENCE: 217
acgaggaaac catttgtaat ttcacggatg ccctcaatat cctgttggct gaggcagtta 60
tcggtcgtgt aactccggta gccgatatcg agctgctgtc tgcagagcag aaacaacagc 120
tggaggaatg gaacaacacc gatggtgaat atccgtctag caagcgtctg caccacct 178

<210> SEQ ID NO 218
<211> LENGTH: 98
<212> TYPE: DNA
<213> ORGANISM: Artificial Sequence
<220> FEATURE:
<223> OTHER INFORMATION: Synthetic nucleotide

<400> SEQUENCE: 218
gtgaatatcc gtctagcaag cgtctgcacc acctgattga agaggtggtg gaacgtcacg 60
aagacaaaat cgctgtggtg tgcgacgaac gtgaactg 98

<210> SEQ ID NO 219
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 219
tcacgaagac aaaatcgctg tggtgtgcga cgaacgtgaa ctgacttacg gtgaactcaa 60
tgcccagggc aactccctgg cgcgttacct gcgcagcatt ggtattctgc ctgaacagct 120
ggttgcgctg tttctggaca aatccgaaaa attgatcgta accatcctgg gcgtctggaa 180
atccggtgct gcttacgtgc caattgaccc gacctaccct gacgaacgtg ttcgtttcgt 240
tctggacgac acgaaagccc gtgcgattat cgcttccaat cagcatgttg aacgcct 297

<210> SEQ ID NO 220
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 220
tgatcgtaac catcctgggc gtctggaaat ccggtgctgc ttacgtgcca attgacccga 60
cctaccctga cgaacgtgtt cgtttcgttc tggacgacac gaaagcccgt gcgattatcg 120
cttccaatca gcatgttgaa cgcctccagc gtgaagtaat cggtgatcgc aacctgtgca 180
tcatccgtct cgaaccactg ctggcgagcc ttgcgcagga ttcttctaaa ttccctgccc 240
acaacctgga tgatttgccg ctgaccagcc agcagctggc gtacgttact tatacca 297

<210> SEQ ID NO 221
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 221
agcgtgaagt aatcggtgat cgcaacctgt gcatcatccg tctcgaacca ctgctggcga 60
gccttgcgca ggattcttct aaattccctg cccacaacct ggatgatttg ccgctgacca 120
gccagcagct ggcgtacgtt acttatacca gcggtaccac cggctttccg aaaggcattt 180
tcaaacagca cactaacgtt gttaactcca tcacagacct gtccgctcgt tacggtgttg 240
caggtcaaca ccatgaagct atcctgctct tcagtgcttg cgttttcgaa ccgttcg 297

<210> SEQ ID NO 222
<211> LENGTH: 281
<212> TYPE: DNA
<213> ORGANISM: Artificial Sequence
<220> FEATURE:
<223> OTHER INFORMATION: Synthetic nucleotide

<400> SEQUENCE: 222
gttaactcca tcacagacct gtccgctcgt tacggtgttg caggtcaaca ccatgaagct 60
atcctgctct tcagtgcttg cgttttcgaa ccgttcgttc gtcagactct gatggccctg 120
gtgaacggtc acctgctcgc cgtgattaac gatgtagaaa aatatgacgc tgacaccctc 180
ctcccattta tccgccgtca ctctatcacc tatctgaacg gtactgcgtc ggttctccaa 240
gagtatgact tctctgactg tccgagcctg aaccgtatca t 281

<210> SEQ ID NO 223
<211> LENGTH: 295
<212> TYPE: DNA
<213> ORGANISM: Artificial Sequence
<220> FEATURE:
<223> OTHER INFORMATION: Synthetic nucleotide

<400> SEQUENCE: 223
ctatcaccta tctgaacggt actgcgtcgg ttctccaaga gtatgacttc tctgactgtc 60
cgagcctgaa ccgtatcatc ctggtgggcg agaacctgac cgaagcacgt tacctggcac 120
tgcgtcagcg tttcaaaaat cgtattctga acgagtacgg tttcaccgag tctgcgttcg 180
tgactgcgct gaaaattttc gatccggaaa gcacccgcaa agatacctcc ctggggcgtc 240
cggtgcgcaa tgttaaatgc tatatcttga accctagcct gaaacgcgtg ccaat 295

<210> SEQ ID NO 224
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 224
acgagtacgg tttcaccgag tctgcgttcg tgactgcgct gaaaattttc gatccggaaa 60
gcacccgcaa agatacctcc ctggggcgtc cggtgcgcaa tgttaaatgc tatatcttga 120
accctagcct gaaacgcgtg ccaattggtg ctacaggtga gctgcatatt ggcggcctgg 180
gtatctccaa gggttacttg aatcgtccgg aactgacgcc gcaccgcttc atcccgaacc 240
cgtttcagac cgattgcgaa aaacagctgg gtatcaactc tctgatgtac aaaaccg 297

<210> SEQ ID NO 225
<211> LENGTH: 297
<212> TYPE: DNA
<213> ORGANISM: Artificial Sequence
<220> FEATURE:

<223> OTHER INFORMATION: Synthetic nucleotide

<400> SEQUENCE: 225
atcgtccgga actgacgccg caccgcttca tcccgaaccc gtttcagacc gattgcgaaa 60
aacagctggg tatcaactct ctgatgtaca aaaccggtga tctggctcgc tggctcccga 120
acggtgaagt tgaatacctg ggccgtgcgg atttccagat caaactgcgc ggtattcgta 180
ttgagccggg cgaaatcgag actatgctgg cgatgtatcc gcgcgttcgt acctccctgg 240
tggtttccaa gaaattacgt aacggtcctg aagaaacaac gaacgaacac ctggtag 297

<210> SEQ ID NO 226
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 226
cggatttcca gatcaaactg cgcggtattc gtattgagcc gggcgaaatc gagactatgc 60
tggcgatgta tccgcgcgtt cgtacctccc tggtggtttc caagaaatta cgtaacggtc 120
ctgaagaaac aacgaacgaa cacctggtag gctactacgt atgcgactcc gcatctgttt 180
ccgaagcgga tctgctgtcc ttcctggaga agaagctgcc gcgttatatg attccgactc 240
gtctggtaca gctgagccag atcccggtta acgtcaacgg taaagccgat ctgcgtg 297

<210> SEQ ID NO 227
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 227
ttcctggaga agaagctgcc gcgttatatg attccgactc gtctggtaca gctgagccag 60
atcccggtta acgtcaacgg taaagccgat ctgcgtgctc tgccggcggt tgatatctcc 120
aacagcaccg aagttcgttc tgatctgcgt ggtgataccg aaattgccct cggcgaaatc 180
tgggcggacg tgctgggcgc gcgtcagcgt tcggttagcc gtaacgataa ctttttccgc 240
ctcggtggcc actctatcac ctgcatccag ctgattgcgc gtatccgtca gcgtcagc 298

<210> SEQ ID NO 228
<211> LENGTH: 307
<212> TYPE: DNA
<213> ORGANISM: Artificial Sequence
<220> FEATURE:
<223> OTHER INFORMATION: Synthetic nucleotide

<400> SEQUENCE: 228
acctgcatcc agctgattgc gcgtatccgt cagcgtcagc gtttgtctgt gtctatctct 60
gtggaagacg tgtttgctac acgcactctt gagcgtatgg ccgacctgtt gcaaaacaaa 120
cagcaagaga aatgcgacaa accacacgaa gcaccgactg aactgcttga agaaaacgct 180
gcgactgata acatctacct ggcgaacagc ctgcagcaag gtttcgtcta ccattacctg 240
aaaagcatgg aacaaagtga tgcttatgta atgcagagcg ttctgcgtta caacaccacc 300
ctttccc 307

<210> SEQ ID NO 229
<211> LENGTH: 159

<212> TYPE: DNA
<213> ORGANISM: Artificial Sequence
<220> FEATURE:
<223> OTHER INFORMATION: Synthetic nucleotide

<400> SEQUENCE: 229
catggaacaa agtgatgctt atgtaatgca gagcgttctg cgttacaaca ccaccctttc 60
cccggatctg ttccagcgtg cctggaaaca cgcgcagcaa agcttcccgg ctctgcgtct 120
gcgcttctct tgggaaaaag aagtcttcca gctgctgga 159

<210> SEQ ID NO 230
<211> LENGTH: 150
<212> TYPE: DNA
<213> ORGANISM: Artificial Sequence
<220> FEATURE:
<223> OTHER INFORMATION: Synthetic nucleotide

<400> SEQUENCE: 230
aaagcttccc ggctctgcgt ctgcgcttct cttgggaaaa agaagtcttc cagctgctgg 60
atcaggaccc gcctctggac tggcgtttcc tctacttcac tgatgtggcg gctggtgcag 120
tagaagaccg taaactggaa gatttacgcc 150

<210> SEQ ID NO 231
<211> LENGTH: 188
<212> TYPE: DNA
<213> ORGANISM: Artificial Sequence
<220> FEATURE:
<223> OTHER INFORMATION: Synthetic nucleotide

<400> SEQUENCE: 231
ctggtgcagt agaagaccgt aaactggaag atttacgccg ccaggacctc accgagcgtt 60
ttaaactgga tgtgggccgt ctgtttcgcg tttacctgat caaacacagc gaaaaccgtt 120
tcacttgtct gttctcttgt caccacgcta tcctggacgg ctggtcctta ccgcttctgt 180
tcgaaaaa 188

<210> SEQ ID NO 232
<211> LENGTH: 300
<212> TYPE: DNA
<213> ORGANISM: Artificial Sequence
<220> FEATURE:
<223> OTHER INFORMATION: Synthetic nucleotide

<400> SEQUENCE: 232
cgtttacctg atcaaacaca gcgaaaaccg tttcacttgt ctgttctctt gtcaccacgc 60
tatcctggac ggctggtcct taccgcttct gttcgaaaaa gtacacgaaa catacctgca 120
actgctgcac ggcgataacc tgacctcctc tatggatgat ccatacaccc gtacccaacg 180
ctacctgcat gcgcaccgcg aagatcacct cgacttttgg gctggcgtgg tgcagaaaat 240
caacgaacgt tgcgatatga atgctctgtt aaacgaacgc agccgctata aagtgcagct 300

<210> SEQ ID NO 233
<211> LENGTH: 240
<212> TYPE: DNA
<213> ORGANISM: Artificial Sequence
<220> FEATURE:
<223> OTHER INFORMATION: Synthetic nucleotide

<400> SEQUENCE: 233
tgctctgtta aacgaacgca gccgctataa agtgcagctg gccgactacg atcaggtaca 60
ggaacagcgt cagctgacga tcgctctgag cggtgacgcg tggctggcgg atctgcgcca 120
gacatgcagt gcgcagggca tcacgctgca ctctatcctg caatttgtat ggcatgcagt 180
tctgcatgcc tacggtggcg gtactcacac tatcactggc accactattt ctggtcgcaa 240

<210> SEQ ID NO 234
<211> LENGTH: 282
<212> TYPE: DNA
<213> ORGANISM: Artificial Sequence
<220> FEATURE:
<223> OTHER INFORMATION: Synthetic nucleotide

<400> SEQUENCE: 234
acggtggcgg tactcacact atcactggca ccactatttc tggtcgcaac ctcccgatcc 60
tgggtatcga gcgtgcggta ggcccgtaca ttaacaccct gccgttagtg ttggaccatt 120
ctacttttaa agacaagacg atcatggaag ctattgaaga cgtccaagcg aaggtgaatg 180
ttatgaactc ccgtggtaat gtagaactgg gtcgcctgca caaaaccgac ctgaaacatg 240
gcctgttcga ttctctgttt gtgctggaaa actatccaaa cc 282

<210> SEQ ID NO 235
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 235
gctattgaag acgtccaagc gaaggtgaat gttatgaact cccgtggtaa tgtagaactg 60
ggtcgcctgc acaaaaccga cctgaaacat ggcctgttcg attctctgtt tgtgctggaa 120
aactatccaa acctggataa atcccgtact ctggagcacc aaactgaact gggttactcc 180
atcgagggtg gtaccgaaaa actgaactat ccgctggcgg tgattgctcg tgaggttgag 240
accactggcg gctttactgt tagcatctgc tatgcgagcg aactgtttga agaggtga 298

<210> SEQ ID NO 236
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 236
aactgaacta tccgctggcg gtgattgctc gtgaggttga gaccactggc ggctttactg 60
ttagcatctg ctatgcgagc gaactgtttg aagaggtgat gatcagcgag cttctccata 120
tggtacagga taccctgatg caggttgcac gcgggctcaa cgaacctgtg ggctccctgg 180
aatacctgtc ttccatccag ttagagcagc tggcagcgtg gaacgccacc gaagcggagt 240
tcccggacac gaccctgcat gaaatgttcg agaacgaagc atctcaaaag ccggataa 298

<210> SEQ ID NO 237
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 237
ttagagcagc tggcagcgtg gaacgccacc gaagcggagt tcccggacac gaccctgcat 60
gaaatgttcg agaacgaagc atctcaaaag ccggataaaa ttgcagtcgt gtacgaagaa 120
acctctctga cctatcgcga gctgaacgaa cgtgccaatc gcatggcgca ccagctgcgt 180
tccgacgttt ctccgaaccc gaacgaagtg atcgcgctgg ttatggacaa gagtgaacac 240
atgatcgtaa atatcttggc tgtgtggaaa tctggtggcg catacgtgcc gatcgatc 298

<210> SEQ ID NO 238
<211> LENGTH: 268
<212> TYPE: DNA
<213> ORGANISM: Artificial Sequence
<220> FEATURE:
<223> OTHER INFORMATION: Synthetic nucleotide

<400> SEQUENCE: 238
gagtgaacac atgatcgtaa atatcttggc tgtgtggaaa tctggtggcg catacgtgcc 60
gatcgatccg ggctacccga atgaccgtat tcagtatatc ctcgaggaca ctcaggcgtt 120
ggctgttatc gcagattctt gttacctgcc tcgtatcaaa ggtatggccg cgtctggtac 180
gctgctctac ccgtctgtcc tgccggcaaa cccagacagc aaatggtctg tgtcaaaccc 240
gtcgccgctg tctcgtagca ccgacctg 268

<210> SEQ ID NO 239
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 239
cgtctggtac gctgctctac ccgtctgtcc tgccggcaaa cccagacagc aaatggtctg 60
tgtcaaaccc gtcgccgctg tctcgtagca ccgacctggc atacatcatc tacacctctg 120
gcaccaccgg ccgcccgaaa ggcgtgactg tggagcatca cggtgtggtg aacctgcagg 180
tatccctgag caaagttttt ggtctgcgtg acaccgacga cgaagtcatc ctgtcttttt 240
ctaactacgt tttcgatcac ttcgtagaac agatgactga tgctatcctg aacgggc 297

<210> SEQ ID NO 240
<211> LENGTH: 260
<212> TYPE: DNA
<213> ORGANISM: Artificial Sequence
<220> FEATURE:
<223> OTHER INFORMATION: Synthetic nucleotide

<400> SEQUENCE: 240
ctaactacgt tttcgatcac ttcgtagaac agatgactga tgctatcctg aacgggcaga 60
cgctgctggt tctgaacgat ggtatgcgtg gtgacaaaga acgcctgtac cgctacatcg 120
aaaagaaccg tgtaacttat ctgtctggta ctccatctgt ggtgtctatg tatgagttca 180
gccgtttcaa agaccacctg cgccgcgtcg attgcgtcgg tgaagctttc agcgagccgg 240
tcttcgacaa aatccgtgaa 260

<210> SEQ ID NO 241
<211> LENGTH: 192
<212> TYPE: DNA
<213> ORGANISM: Artificial Sequence
<220> FEATURE:
<223> OTHER INFORMATION: Synthetic nucleotide

<400> SEQUENCE: 241
accttccacg gtttggttat caatggttat ggcccaactg aagttagcat cactacccat 60
aagcgtttat accctttccc agagcgccgc atggataagt cgatcggcca gcaggtccac 120
aactctacta gctacgtact gaatgaagat atgaagcgta ccccgatcgg tgctgtgggt 180
gagctgtacc tg 192

<210> SEQ ID NO 242
<211> LENGTH: 259
<212> TYPE: DNA
<213> ORGANISM: Artificial Sequence
<220> FEATURE:
<223> OTHER INFORMATION: Synthetic nucleotide

<400> SEQUENCE: 242
tgaatgaaga tatgaagcgt accccgatcg gtgctgtggg tgagctgtac ctgggcggtg 60
aaggtgttgt ccgcggttat cataatcgtg cggatgttac cgccgagcgc ttcatcccga 120
acccgttcca gtctgaggaa gataaacgtg aaggccgtaa cagtcgcctg tacaagacgg 180
gtgatctggt tcgctggatc ccgggtagct ccggcgaagt cgaatacctg ggtcgcaatg 240
acttccaggt taagattcg 259

<210> SEQ ID NO 243
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 243
cgaagtcgaa tacctgggtc gcaatgactt ccaggttaag attcgcggcc tccgtatcga 60
gctgggtgaa atcgaagcga tcctgagcag ctaccacggc attaaacaga gcgtagtgat 120
cgcaaaagac tgccgtgagg gggcacagaa attcctggtc ggctattacg ttgcagacgc 180
tgccctgccg tccgcagcga tccgtcgttt catgcagtcg cgcctcccgg gttacatggt 240
tccgtcccgt ctgatcctgg tttctaaatt ccctgttact ccgtccggga agctgga 297

<210> SEQ ID NO 244
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 244
cgtctgatcc tggtttctaa attccctgtt actccgtccg ggaagctgga caccaaagca 60
ctgccgccgg cggaggaaga aagcgaaatc gacgttgttc caccgcgctc cgaaattgag 120
cgttctctct gcgacatctg ggctgaactg ctggaaatgc acccggaaga aatcggcatt 180
tactctgact tcttctcctt gggcggcgac agcctgaaat ctactaagtt atccttcatg 240
atccatgagt cctttaaccg tgctgtgagc gttagcgcgt tattctgcca tcgcaca 297

<210> SEQ ID NO 245
<211> LENGTH: 150
<212> TYPE: DNA
<213> ORGANISM: Artificial Sequence
<220> FEATURE:
<223> OTHER INFORMATION: Synthetic nucleotide

<400> SEQUENCE: 245
tccttcatga tccatgagtc ctttaaccgt gctgtgagcg ttagcgcgtt attctgccat 60
cgcacagttg aagctcaaac tcacctgatc ttgaacgacg cagcagatgt acacgaaatt 120
accccgatcg attgcaacga cacccagatg 150

<210> SEQ ID NO 246
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 246
gaagctcaaa ctcacctgat cttgaacgac gcagcagatg tacacgaaat taccccgatc 60
gattgcaacg acacccagat gatcccggtt tcccgtgcac aggaacgtct gctgttcatt 120
catgaattcg aaaacggttc taacgcttac aacattgacg cggctttcga actgccaggt 180
tctgtggacg cgagcctgct ggaacaggcc cttcgtggca acctggcacg tcacgaagca 240
ctgcgcaccc tgctggttaa agatcacgcc actggtattt acctgcagaa agtactg 297

<210> SEQ ID NO 247
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 247
aggaacgtct gctgttcatt catgaattcg aaaacggttc taacgcttac aacattgacg 60
cggctttcga actgccaggt tctgtggacg cgagcctgct ggaacaggcc cttcgtggca 120
acctggcacg tcacgaagca ctgcgcaccc tgctggttaa agatcacgcc actggtattt 180
acctgcagaa agtactgagt ccggacgaag cgcaaggtat gttttctgtt aatgtagata 240
ctgctaaaca ggttgaacgt ctggatcagg aaattgcttc tctgtctcag cacgtct 297

<210> SEQ ID NO 248
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 248
ttgaacgtct ggatcaggaa attgcttctc tgtctcagca cgtcttccgc ctggacgacg 60
aactgccgtg ggaggcgcgc atcctgaaac tggaatctgg cggtctgtac ctgatcttgg 120
ccttccacca cacctgcttc gatgcatgga gcctgaaagt tttcgaacag gagctgcgcg 180
cgctgtacgc agcgcttcag aaaacgaaat ctgcagcgaa cttaccggca ttaaaagcac 240
agtataagga atacgctctg taccaccgcc gccagcttag cggcgaccgc atgcgtaa 298

<210> SEQ ID NO 249
<211> LENGTH: 295
<212> TYPE: DNA
<213> ORGANISM: Artificial Sequence
<220> FEATURE:
<223> OTHER INFORMATION: Synthetic nucleotide

<400> SEQUENCE: 249
aatacgctct gtaccaccgc cgccagctta gcggcgaccg catgcgtaac ctgtccgatt 60
tctggttacg taaactgatc ggtctggaac cactgcagct gatcaccgat cgtccgcgtc 120
cggttcagtt caaatacgac ggtgacgatc tgagcatcga actgtccaag aaagagaccg 180

-continued aaaacctgcg cggcgttgca aaacgttgta agtcttcctt atatgttgta ctggtatctg 240
tttactgtgt catgctggca agctacgcca accagagcga tgttagcgtg ggcat 295

<210> SEQ ID NO 250
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 250
tgatcaccga tcgtccgcgt ccggttcagt tcaaatacga cggtgacgat ctgagcatcg 60
aactgtccaa gaaagagacc gaaaacctgc gcggcgttgc aaaacgttgt aagtcttcct 120
tatatgttgt actggtatct gtttactgtg tcatgctggc aagctacgcc aaccagagcg 180
atgttagcgt gggcatccca gtatcacacc gtacgcaccc gcagttccag tctgttatcg 240
gctttttcgt taacctggtc gttctgcgtg tagatatcag ccagtccgct atttgcg 297

<210> SEQ ID NO 251
<211> LENGTH: 127
<212> TYPE: DNA
<213> ORGANISM: Artificial Sequence
<220> FEATURE:
<223> OTHER INFORMATION: Synthetic nucleotide

<400> SEQUENCE: 251
ggtcgttctg cgtgtagata tcagccagtc cgctatttgc ggtttaatcc gtcgcgtcat 60
gaaagaactg gttgacgcgc agctgcacca ggatatgccg ttccaggaag ttacgaaact 120
gctgcag 127

<210> SEQ ID NO 252
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 252
gccgttccag gaagttacga aactgctgca ggtggataac gatcctagcc gtcacccgtt 60
ggttcagaac gtatttaact ttgagtctcg cgcgaacggt gaacacgatg cccgctctga 120
agacgagggc tctcttgcat tcaatcagta ccgtccggtt cagccggttg acagcgtggc 180
caaattcgat ctgaacgcca ccgtcaccga actggaatcc ggtctgcgtg ttaatttcaa 240
ctacgcgacc agcttattca ataaatccac catccagggc ttcctgcaca catatgaa 298

<210> SEQ ID NO 253
<211> LENGTH: 296
<212> TYPE: DNA
<213> ORGANISM: Artificial Sequence
<220> FEATURE:
<223> OTHER INFORMATION: Synthetic nucleotide

<400> SEQUENCE: 253
ccagcttatt caataaatcc accatccagg gcttcctgca cacatatgaa taccttctgc 60
gtcagctgtc cgaactgagc gctgaaggca tcaacgaaga tacccagctg tcactggttc 120
gcccgactga gaacggggat ctgcacctgc cactggccca gtctccgctc gcgaccactg 180
cagaagaaca gaaagttgct tccctgaacc aggctttcga acgtgaagcc ttcctggcgg 240
cggaaaaaat cgccgttgtt caaggggacc gcgctctgtc gtatgccgac ctgaac 296

<210> SEQ ID NO 254
<211> LENGTH: 299
<212> TYPE: DNA
<213> ORGANISM: Artificial Sequence
<220> FEATURE:
<223> OTHER INFORMATION: Synthetic nucleotide

<400> SEQUENCE: 254
gccgttgttc aaggggaccg cgctctgtcg tatgccgacc tgaacggtca ggctaatcaa 60
ctggcgcgtt atatccagtc cgtctcctgc atcggtgccg acgacggcat cgccctgatg 120
ctggaaaaga gcatcgatac tatcatctgc attctggcaa tctggaaagc aggcgccgcg 180
tatgtgccgc tggatccgac ctacccacca ggccgtgtac aactgatcct ggaggaaatc 240
aaagcgaaag ctgtgctggt acactcttcc cacgcctcta aatgtgaacg tcacggtgc 299

<210> SEQ ID NO 255
<211> LENGTH: 225
<212> TYPE: DNA
<213> ORGANISM: Artificial Sequence
<220> FEATURE:
<223> OTHER INFORMATION: Synthetic nucleotide

<400> SEQUENCE: 255
cctctaaatg tgaacgtcac ggtgccaaag tcattgcagt agactctccg gctattgaaa 60
cggcagtgag ccagcagtct gcagctgatc tgccgaccat tgctagcctg ggtaatctgg 120
catatatcat ctttactagc ggcacttctg gcaaaccgaa aggcgttctg gtagagcaaa 180
aagccgttct gctgctgcgc gacgccctgc gtgagcgtta cttcg 225

<210> SEQ ID NO 256
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 256
atctttacta gcggcacttc tggcaaaccg aaaggcgttc tggtagagca aaaagccgtt 60
ctgctgctgc gcgacgccct gcgtgagcgt tacttcggtc gtgattgtac caaacatcac 120
ggtgttctgt tcctgagcaa ctacgttttc gacttctccg tagaacagct ggttctgtct 180
gtactctcag gccacaaact gattgtcccg ccggcggagt ttgtggcgga tgacgaattc 240
tatcgtatgg cctctaccca cggtctttct tacctgtctg gcaccccgag cctgctt 297

<210> SEQ ID NO 257
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 257
ttcgacttct ccgtagaaca gctggttctg tctgtactct caggccacaa actgattgtc 60
ccgccggcgg agtttgtggc ggatgacgaa ttctatcgta tggcctctac ccacggtctt 120
tcttacctgt ctggcacccc gagcctgctt caaaaaatcg atctggcacg tctggatcac 180
ctgcaggttg taaccgcggc gggtgaggaa ctccacgcga cccagtacga aaaaatgcgt 240
cgtcgtttta acggtccaat ctacaacgct tatggtgtta ccgagacaac ggtgtac 297

-continued

<210> SEQ ID NO 258
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 258
ggtccaatct acaacgctta tggtgttacc gagacaacgg tgtacaacat catcgctgaa 60
ttcaccacca actccatctt cgaaaacgca ttacgcgaag tcctgccggg cacccgtgcg 120
tacgttctga acgcggcgct gcagccggtt ccattcgacg ctgtgggtga actgtatctg 180
gccggcgata gcgtaacccg tggttacctg aaccagccgt tgctgaccga tcagcgtttc 240
atccctaacc cgttctgcaa ggaagaagac atcgcgatgg gtcgtttcgc tcgtctgt 298

<210> SEQ ID NO 259
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 259
aaaccggcga cctggttcgc tctcgcttca accgccagca gcagccgcag ctggaatacc 60
tgggccgtgg cgacctgcag attaaaatgc gtggttaccg cattgaaatt agcgaagtac 120
agaacgtgct gacctcctcc ccgggcgtac gcgaaggtgc ggttgtggct aaatatgaaa 180
acaacgacac gtatagccgt actgcacatt ccttagtcgg ttattatacc actgataacg 240
aaacagtttc agaagctgat atcctcacct tcatgaaagc gcgtctgccg acctata 297

<210> SEQ ID NO 260
<211> LENGTH: 104
<212> TYPE: DNA
<213> ORGANISM: Artificial Sequence
<220> FEATURE:
<223> OTHER INFORMATION: Synthetic nucleotide

<400> SEQUENCE: 260
ctaacccgtt ctgcaaggaa gaagacatcg cgatgggtcg tttcgctcgt ctgtacaaaa 60
ccggcgacct ggttcgctct cgcttcaacc gccagcagca gccg 104

<210> SEQ ID NO 261
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 261
tactgcacat tccttagtcg gttattatac cactgataac gaaacagttt cagaagctga 60
tatcctcacc ttcatgaaag cgcgtctgcc gacctatatg gtgccttctc acctgtgctg 120
cctggaaggt gctctgccag tcactattaa cggtaaactg gacgttcgtc gtctgcctga 180
aattatcaac gacagtgcgc aatcctcata ttccccgccg cgcaacatta tcgaagcgaa 240
aatgtgccgt ttatgggaaa gcgcgctggg tatggaacgc tgcggtattg acgatgac 298

<210> SEQ ID NO 262
<211> LENGTH: 198
<212> TYPE: DNA
<213> ORGANISM: Artificial Sequence
<220> FEATURE:
<223> OTHER INFORMATION: Synthetic nucleotide

<400> SEQUENCE: 262
cgtttatggg aaagcgcgct gggtatggaa cgctgcggta ttgacgatga cctcttcaag 60
ctgggggggg attctatcac cagtctgcac ctcgtcgcac agattcacaa tcaggtgggc 120
tgtaagatta ccgtgcgcga tattttcgaa caccgtaccg cgcgtgctct ccacgatcac 180
gttttcatga aggatagc 198

<210> SEQ ID NO 263
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 263
gtaccgcgcg tgctctccac gatcacgttt tcatgaagga tagcgatcgc tctaacgtca 60
cccagttccg taccgagcag gggccggtca ttggcgaagc tccgctgctg ccgatccagg 120
attggttctt gagcaaagct ctgcagcacc ctatgtactg gaaccacacg ttctacgtac 180
gtaccccgga actggacgtt gattccctga gtgcggccgt tcgtgacctg cagcagtacc 240
acgacgtttt ccgcatgcgc ctgaaacgcg aagaagttgg ctttgtacag tcctttg 297

<210> SEQ ID NO 264
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 264
tttccgcatg cgcctgaaac gcgaagaagt tggctttgta cagtcctttg ccgaagactt 60
ttccccggcg cagctgcgtg tactgaacgt gaaggacgtg gatggtagcg cggcggttaa 120
cgaaatcctg gacggttggc aaagcggctt caacctggaa aacggtccga tcggctcgat 180
cggttatctg catggctatg aagaccgctc cgcacgtgtg tggttttctg tacaccacat 240
ggccattgac actgtttcct ggcagatcct ggttcgtgat ctgcagactc tgtaccgt 298

<210> SEQ ID NO 265
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 265
acctggaaaa cggtccgatc ggctcgatcg gttatctgca tggctatgaa gaccgctccg 60
cacgtgtgtg gttttctgta caccacatgg ccattgacac tgtttcctgg cagatcctgg 120
ttcgtgatct gcagactctg taccgtaacg gttccctggg ttccaaaggt tcttcatttc 180
gccaatgggc cgaggcaatc caaaactaca aagcgagcga ctcggaacgt aaccattgga 240
acaagctggt tatggaaact gcatcgtcga tcagcgcgct gccgacctcc actggttc 298

<210> SEQ ID NO 266
<211> LENGTH: 297
<212> TYPE: DNA
<213> ORGANISM: Artificial Sequence
<220> FEATURE:

<223> OTHER INFORMATION: Synthetic nucleotide

<400> SEQUENCE: 266
aaaactacaa agcgagcgac tcggaacgta accattggaa caagctggtt atggaaactg 60
catcgtcgat cagcgcgctg ccgacctcca ctggttctcg cgtacgtctc tcccgttctc 120
tgtctcctga aaaaactgct tctctgatcc agggtggcat cgatcgtcag gatgtaagcg 180
tatacgattc tctgctgact tctgttggcc tggctttgca acacatcgcg ccgactggcc 240
cgtctatggt tacaatcgag ggtcacggcc gcgaagaagt tgaccagacc ctggatg 297

<210> SEQ ID NO 267
<211> LENGTH: 298
<212> TYPE: DNA
<213> ORGANISM: Artificial Sequence
<220> FEATURE:
<223> OTHER INFORMATION: Synthetic nucleotide

<400> SEQUENCE: 267
ttctgttggc ctggctttgc aacacatcgc gccgactggc ccgtctatgg ttacaatcga 60
gggtcacggc cgcgaagaag ttgaccagac cctggatgtt tctcgtacga tgggctggtt 120
cactaccatg tatccgttcg aaatcccgcg tctgtcgacg gaaaacatcg tgcagggtgt 180
tgttgctgta agtgaacgct tccgccaagt tccggctcgc ggtgttggtt atggtactct 240
gtacggttac acccagcacc ctctgccgca ggttactgtt aactacctgg gccagctg 298

<210> SEQ ID NO 268
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 268
acacccagca ccctctgccg caggttactg ttaactacct gggccagctg gctcgtaaac 60
agagcaagcc gaaagaatgg gttctggcag ttggtgataa cgagttcgag tacggtctga 120
tgacctcccc ggaggataag gaccgttcga gctccgcagt ggatgttacg gccgtctgca 180
tcgacgggac gatgatcatc gatgtggact cggcttggtc tttggaagaa tctgaacagt 240
tcatctcgtc aattgaagaa ggtctgaaca aaatcctgga cggtcgtgca tcccagc 297

<210> SEQ ID NO 269
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 269
cgtaaacaga gcaagccgaa agaatgggtt ctggcagttg gtgataacga gttcgagtac 60
ggtctgatga cctccccgga ggataaggac cgttcgagct ccgcagtgga tgttacggcc 120
gtctgcatcg acgggacgat gatcatcgat gtggactcgg cttggtcttt ggaagaatct 180
gaacagttca tctcgtcaat tgaagaaggt ctgaacaaaa tcctggacgg tcgtgcatcc 240
cagcagacta gccgctttcc ggatgtgccg cagccagcag agacctacac cccatac 297

<210> SEQ ID NO 270
<211> LENGTH: 297
<212> TYPE: DNA
<213> ORGANISM: Artificial Sequence
<220> FEATURE:
<223> OTHER INFORMATION: Synthetic nucleotide

<400> SEQUENCE: 270
gatgtggact cggcttggtc tttggaagaa tctgaacagt tcatctcgtc aattgaagaa 60
ggtctgaaca aaatcctgga cggtcgtgca tcccagcaga ctagccgctt tccggatgtg 120
ccgcagccag cagagaccta caccccatac ttcgaatatc tggaaccgcc gcgccagggc 180
ccgaccctgt ttctgctgcc accgggtgaa ggtggtgcgg aatcttactt caacaacatc 240
gtcaaacgct tgcgtcaaac taacatggtt gtctttaaca actactacct gcactcc 297

<210> SEQ ID NO 271
<211> LENGTH: 296
<212> TYPE: DNA
<213> ORGANISM: Artificial Sequence
<220> FEATURE:
<223> OTHER INFORMATION: Synthetic nucleotide

<400> SEQUENCE: 271
gaatatctgg aaccgccgcg ccagggcccg accctgtttc tgctgccacc gggtgaaggt 60
ggtgcggaat cttacttcaa caacatcgtc aaacgcttgc gtcaaactaa catggttgtc 120
tttaacaact actacctgca ctccaaacgt ctgcgcacct tcgaggaact ggctgaaatg 180
tatctggacc aggtacgcgg catccaaccg cacggtccat accacttcat cggctggagc 240
ttcgggggca ttctggcgat ggagatgtcc cgtcgtctgg ttgcgagcga cgaaaa 296

<210> SEQ ID NO 272
<211> LENGTH: 282
<212> TYPE: DNA
<213> ORGANISM: Artificial Sequence
<220> FEATURE:
<223> OTHER INFORMATION: Synthetic nucleotide

<400> SEQUENCE: 272
ggcattctgg cgatggagat gtcccgtcgt ctggttgcga gcgacgaaaa aattggtttt 60
ctgggtatta tcgacaccta tttcaacgta cgtggtgcca ctcgcaccat tggccttggt 120
gatactgaaa tcctggatcc gatccaccac atctataacc cggacccggc aaactttcag 180
cgtctgccgt ctgccaccga ccgtatcgtc ctgtttaagg ccatgcgtcc gaataataaa 240
tatgaatcag aaaaccagcg tcgcctgtat gagtactacg ac 282

<210> SEQ ID NO 273
<211> LENGTH: 202
<212> TYPE: DNA
<213> ORGANISM: Artificial Sequence
<220> FEATURE:
<223> OTHER INFORMATION: Synthetic nucleotide

<400> SEQUENCE: 273
ctacgacgcg ttagattcca cggactggac cgcatgttac caggcgatcc ctacctcctc 60
atggtcgcgc ctgcgcacga tccacacctt cccgggttcg gaaatccaca accgctggtc 120
ccgttgcgtt cgtctgagcc gtaacaccag ccttgccatc gacccgtctc tggcggctca 180
gtacatcggt cgttggaagt aa 202

<210> SEQ ID NO 274
<211> LENGTH: 980
<212> TYPE: DNA
<213> ORGANISM: Artificial Sequence
<220> FEATURE:

<223> OTHER INFORMATION: Synthetic nucleotide

<400> SEQUENCE: 274
atgacccaat tgaagccgcc taacgggacc actccgatcg gcttcagcgc cactactagc 60
ctgaacgcta gcggctcttc ctcggttaag aatggtacca tcaagccttc gaatggtatc 120
ttcaaacctt ctactcgtga caccatggac ccgtgctcgg gcaacgccgc tgacggctcc 180
attcgcgtac gttttcgcgg tggcatcgaa cgttggaaag agtgtgtaaa ccaagtgccg 240
gagcgttgcg acctgtctgg tctgaccacg gacagcaccc gctaccagct ggcttcgacc 300
ggcttcggcg acgcgagcgc ggcttaccag gaacgtctga tgactgtgcc ggtagatgtt 360
catgctgcgc tccaggagct gtgcctggaa cgccgcgtct ctgtgggttc tgtgatcaac 420
ttcagcgttc accagatgct gaagggtttt ggcaacggta ctcacactat caccgcgagc 480
ctgcaccgcg aacagaatct gcagaactcc tctccgtctt gggtcgtttc ccctactatc 540
gtgacccatg aaaaccgcga tggctggtca gtggcgcagg cagtggagtc tatcgaggct 600
ggtcgtggct ccgaaaagga atctgtgacc gcgattgatt ccggctcctc cctggtcaaa 660
atgggtctgt tcgatctgct ggtttccttc gtcgatgcgg atgacgcgcg tatcccttgc 720
ttcgactttc cgctggctgt tattgtgcgc gagtgcgatg caaacctgtc tctcaccctt 780
cgcttctcgg actgcctgtt caacgaggaa accatttgta atttcacgga tgccctcaat 840
atcctgttgg ctgaggcagt tatcggtcgt gtaactccgg tagccgatat cgagctgctg 900
tctgcagagc agaaacaaca gctggaggaa tggaacaaca ccgatggtga atatccgtct 960
agcaagcgtc tgcaccacct 980

<210> SEQ ID NO 275
<211> LENGTH: 1203
<212> TYPE: DNA
<213> ORGANISM: Artificial Sequence
<220> FEATURE:
<223> OTHER INFORMATION: Synthetic nucleotide

<400> SEQUENCE: 275
gtgaatatcc gtctagcaag cgtctgcacc acctgattga agaggtggtg gaacgtcacg 60
aagacaaaat cgctgtggtg tgcgacgaac gtgaactgac ttacggtgaa ctcaatgccc 120
agggcaactc cctggcgcgt tacctgcgca gcattggtat tctgcctgaa cagctggttg 180
cgctgtttct ggacaaatcc gaaaaattga tcgtaaccat cctgggcgtc tggaaatccg 240
gtgctgctta cgtgccaatt gacccgacct accctgacga acgtgttcgt ttcgttctgg 300
acgacacgaa agcccgtgcg attatcgctt ccaatcagca tgttgaacgc ctccagcgtg 360
aagtaatcgg tgatcgcaac ctgtgcatca tccgtctcga accactgctg gcgagccttg 420
cgcaggattc ttctaaattc cctgcccaca acctggatga tttgccgctg accagccagc 480
agctggcgta cgttacttat accagcggta ccaccggctt tccgaaaggc attttcaaac 540
agcacactaa cgttgttaac tccatcacag acctgtccgc tcgttacggt gttgcaggtc 600
aacaccatga agctatcctg ctcttcagtg cttgcgtttt cgaaccgttc gttcgtcaga 660
ctctgatggc cctggtgaac ggtcacctgc tcgccgtgat taacgatgta gaaaaatatg 720
acgctgacac cctcctccca tttatccgcc gtcactctat cacctatctg aacggtactg 780
cgtcggttct ccaagagtat gacttctctg actgtccgag cctgaaccgt atcatcctgg 840
tgggcgagaa cctgaccgaa gcacgttacc tggcactgcg tcagcgtttc aaaaatcgta 900
ttctgaacga gtacggtttc accgagtctg cgttcgtgac tgcgctgaaa attttcgatc 960
cggaaagcac ccgcaaagat acctccctgg ggcgtccggt gcgcaatgtt aaatgctata 1020
tcttgaaccc tagcctgaaa cgcgtgccaa ttggtgctac aggtgagctg catattggcg 1080
gcctgggtat ctccaagggt tacttgaatc gtccggaact gacgccgcac cgcttcatcc 1140
cgaacccgtt tcagaccgat tgcgaaaaac agctgggtat caactctctg atgtacaaaa 1200
ccg 1203

<210> SEQ ID NO 276
<211> LENGTH: 645
<212> TYPE: DNA
<213> ORGANISM: Artificial Sequence
<220> FEATURE:
<223> OTHER INFORMATION: Synthetic nucleotide

<400> SEQUENCE: 276
atcgtccgga actgacgccg caccgcttca tcccgaaccc gtttcagacc gattgcgaaa 60
aacagctggg tatcaactct ctgatgtaca aaaccggtga tctggctcgc tggctcccga 120
acggtgaagt tgaatacctg ggccgtgcgg atttccagat caaactgcgc ggtattcgta 180
ttgagccggg cgaaatcgag actatgctgg cgatgtatcc gcgcgttcgt acctccctgg 240
tggtttccaa gaaattacgt aacggtcctg aagaaacaac gaacgaacac ctggtaggct 300
actacgtatg cgactccgca tctgtttccg aagcggatct gctgtccttc ctggagaaga 360
agctgccgcg ttatatgatt ccgactcgtc tggtacagct gagccagatc ccggttaacg 420
tcaacggtaa agccgatctg cgtgctctgc cggcggttga tatctccaac agcaccgaag 480
ttcgttctga tctgcgtggt gataccgaaa ttgccctcgg cgaaatctgg gcggacgtgc 540
tgggcgcgcg tcagcgttcg gttagccgta acgataactt tttccgcctc ggtggccact 600
ctatcacctg catccagctg attgcgcgta tccgtcagcg tcagc 645

<210> SEQ ID NO 277
<211> LENGTH: 1043
<212> TYPE: DNA
<213> ORGANISM: Artificial Sequence
<220> FEATURE:
<223> OTHER INFORMATION: Synthetic nucleotide

<400> SEQUENCE: 277
acctgcatcc agctgattgc gcgtatccgt cagcgtcagc gtttgtctgt gtctatctct 60
gtggaagacg tgtttgctac acgcactctt gagcgtatgg ccgacctgtt gcaaaacaaa 120
cagcaagaga aatgcgacaa accacacgaa gcaccgactg aactgcttga agaaaacgct 180
gcgactgata acatctacct ggcgaacagc ctgcagcaag gtttcgtcta ccattacctg 240
aaaagcatgg aacaaagtga tgcttatgta atgcagagcg ttctgcgtta caacaccacc 300
ctttccccgg atctgttcca gcgtgcctgg aaacacgcgc agcaaagctt cccggctctg 360
cgtctgcgct tctcttggga aaaagaagtc ttccagctgc tggatcagga cccgcctctg 420
gactggcgtt tcctctactt cactgatgtg gcggctggtg cagtagaaga ccgtaaactg 480
gaagatttac gccgccagga cctcaccgag cgttttaaac tggatgtggg ccgtctgttt 540
cgcgtttacc tgatcaaaca cagcgaaaac cgtttcactt gtctgttctc ttgtcaccac 600
gctatcctgg acggctggtc cttaccgctt ctgttcgaaa aagtacacga aacatacctg 660
caactgctgc acggcgataa cctgacctcc tctatggatg atccatacac ccgtacccaa 720
cgctacctgc atgcgcaccg cgaagatcac ctcgactttt gggctggcgt ggtgcagaaa 780
atcaacgaac gttgcgatat gaatgctctg ttaaacgaac gcagccgcta taaagtgcag 840
ctggccgact acgatcaggt acaggaacag cgtcagctga cgatcgctct gagcggtgac 900
gcgtggctgg cggatctgcg ccagacatgc agtgcgcagg gcatcacgct gcactctatc 960
ctgcaatttg tatggcatgc agttctgcat gcctacggtg gcggtactca cactatcact 1020
ggcaccacta tttctggtcg caa 1043

<210> SEQ ID NO 278
<211> LENGTH: 1245
<212> TYPE: DNA
<213> ORGANISM: Artificial Sequence
<220> FEATURE:
<223> OTHER INFORMATION: Synthetic nucleotide

<400> SEQUENCE: 278
acggtggcgg tactcacact atcactggca ccactatttc tggtcgcaac ctcccgatcc 60
tgggtatcga gcgtgcggta ggcccgtaca ttaacaccct gccgttagtg ttggaccatt 120
ctacttttaa agacaagacg atcatggaag ctattgaaga cgtccaagcg aaggtgaatg 180
ttatgaactc ccgtggtaat gtagaactgg gtcgcctgca caaaaccgac ctgaaacatg 240
gcctgttcga ttctctgttt gtgctggaaa actatccaaa cctggataaa tcccgtactc 300
tggagcacca aactgaactg ggttactcca tcgagggtgg taccgaaaaa ctgaactatc 360
cgctggcggt gattgctcgt gaggttgaga ccactggcgg ctttactgtt agcatctgct 420
atgcgagcga actgtttgaa gaggtgatga tcagcgagct tctccatatg gtacaggata 480
ccctgatgca ggttgcacgc gggctcaacg aacctgtggg ctccctggaa tacctgtctt 540
ccatccagtt agagcagctg gcagcgtgga acgccaccga agcggagttc ccggacacga 600
ccctgcatga aatgttcgag aacgaagcat ctcaaaagcc ggataaaatt gcagtcgtgt 660
acgaagaaac ctctctgacc tatcgcgagc tgaacgaacg tgccaatcgc atggcgcacc 720
agctgcgttc cgacgtttct ccgaacccga acgaagtgat cgcgctggtt atggacaaga 780
gtgaacacat gatcgtaaat atcttggctg tgtggaaatc tggtggcgca tacgtgccga 840
tcgatccggg ctacccgaat gaccgtattc agtatatcct cgaggacact caggcgttgg 900
ctgttatcgc agattcttgt tacctgcctc gtatcaaagg tatggccgcg tctggtacgc 960
tgctctaccc gtctgtcctg ccggcaaacc cagacagcaa atggtctgtg tcaaacccgt 1020
cgccgctgtc tcgtagcacc gacctggcat acatcatcta cacctctggc accaccggcc 1080
gcccgaaagg cgtgactgtg gagcatcacg gtgtggtgaa cctgcaggta tccctgagca 1140
aagtttttgg tctgcgtgac accgacgacg aagtcatcct gtctttttct aactacgttt 1200
tcgatcactt cgtagaacag atgactgatg ctatcctgaa cgggc 1245

<210> SEQ ID NO 279
<211> LENGTH: 1157
<212> TYPE: DNA
<213> ORGANISM: Artificial Sequence
<220> FEATURE:
<223> OTHER INFORMATION: Synthetic nucleotide

<400> SEQUENCE: 279
ctaactacgt tttcgatcac ttcgtagaac agatgactga tgctatcctg aacgggcaga 60
cgctgctggt tctgaacgat ggtatgcgtg gtgacaaaga acgcctgtac cgctacatcg 120
aaaagaaccg tgtaacttat ctgtctggta ctccatctgt ggtgtctatg tatgagttca 180
gccgtttcaa agaccacctg cgccgcgtcg attgcgtcgg tgaagctttc agcgagccgg 240
tcttcgacaa aatccgtgaa accttccacg gtttggttat caatggttat ggcccaactg 300
aagttagcat cactacccat aagcgtttat accctttccc agagcgccgc atggataagt 360
cgatcggcca gcaggtccac aactctacta gctacgtact gaatgaagat atgaagcgta 420
ccccgatcgg tgctgtgggt gagctgtacc tgggcggtga aggtgttgtc cgcggttatc 480
ataatcgtgc ggatgttacc gccgagcgct tcatcccgaa cccgttccag tctgaggaag 540
ataaacgtga aggccgtaac agtcgcctgt acaagacggg tgatctggtt cgctggatcc 600
cgggtagctc cggcgaagtc gaatacctgg gtcgcaatga cttccaggtt aagattcgcg 660
gcctccgtat cgagctgggt gaaatcgaag cgatcctgag cagctaccac ggcattaaac 720
agagcgtagt gatcgcaaaa gactgccgtg agggggcaca gaaattcctg gtcggctatt 780
acgttgcaga cgctgccctg ccgtccgcag cgatccgtcg tttcatgcag tcgcgcctcc 840
cgggttacat ggttccgtcc cgtctgatcc tggtttctaa attccctgtt actccgtccg 900
ggaagctgga caccaaagca ctgccgccgg cggaggaaga aagcgaaatc gacgttgttc 960
caccgcgctc cgaaattgag cgttctctct gcgacatctg ggctgaactg ctggaaatgc 1020
acccggaaga aatcggcatt tactctgact tcttctcctt gggcggcgac agcctgaaat 1080
ctactaagtt atccttcatg atccatgagt cctttaaccg tgctgtgagc gttagcgcgt 1140
tattctgcca tcgcaca 1157

<210> SEQ ID NO 280
<211> LENGTH: 1066
<212> TYPE: DNA
<213> ORGANISM: Artificial Sequence
<220> FEATURE:
<223> OTHER INFORMATION: Synthetic nucleotide

<400> SEQUENCE: 280
tccttcatga tccatgagtc ctttaaccgt gctgtgagcg ttagcgcgtt attctgccat 60
cgcacagttg aagctcaaac tcacctgatc ttgaacgacg cagcagatgt acacgaaatt 120
accccgatcg attgcaacga cacccagatg atcccggttt cccgtgcaca ggaacgtctg 180
ctgttcattc atgaattcga aaacggttct aacgcttaca acattgacgc ggctttcgaa 240
ctgccaggtt ctgtggacgc gagcctgctg gaacaggccc ttcgtggcaa cctggcacgt 300
cacgaagcac tgcgcaccct gctggttaaa gatcacgcca ctggtattta cctgcagaaa 360
gtactgagtc cggacgaagc gcaaggtatg ttttctgtta atgtagatac tgctaaacag 420
gttgaacgtc tggatcagga aattgcttct ctgtctcagc acgtcttccg cctggacgac 480
gaactgccgt gggaggcgcg catcctgaaa ctggaatctg gcggtctgta cctgatcttg 540
gccttccacc acacctgctt cgatgcatgg agcctgaaag ttttcgaaca ggagctgcgc 600
gcgctgtacg cagcgcttca gaaaacgaaa tctgcagcga acttaccggc attaaaagca 660
cagtataagg aatacgctct gtaccaccgc cgccagctta gcggcgaccg catgcgtaac 720
ctgtccgatt tctggttacg taaactgatc ggtctggaac cactgcagct gatcaccgat 780
cgtccgcgtc cggttcagtt caaatacgac ggtgacgatc tgagcatcga actgtccaag 840
aaagagaccg aaaacctgcg cggcgttgca aaacgttgta agtcttcctt atatgttgta 900
ctggtatctg tttactgtgt catgctggca agctacgcca accagagcga tgttagcgtg 960
ggcatcccag tatcacaccg tacgcacccg cagttccagt ctgttatcgg ctttttcgtt 1020
aacctggtcg ttctgcgtgt agatatcagc cagtccgcta tttgcg 1066

-continued

<210> SEQ ID NO 281
<211> LENGTH: 894
<212> TYPE: DNA
<213> ORGANISM: Artificial Sequence
<220> FEATURE:
<223> OTHER INFORMATION: Synthetic nucleotide

<400> SEQUENCE: 281
ggtcgttctg cgtgtagata tcagccagtc cgctatttgc ggtttaatcc gtcgcgtcat 60
gaaagaactg gttgacgcgc agctgcacca ggatatgccg ttccaggaag ttacgaaact 120
gctgcaggtg gataacgatc ctagccgtca cccgttggtt cagaacgtat ttaactttga 180
gtctcgcgcg aacggtgaac acgatgcccg ctctgaagac gagggctctc ttgcattcaa 240
tcagtaccgt ccggttcagc cggttgacag cgtggccaaa ttcgatctga acgccaccgt 300
caccgaactg gaatccggtc tgcgtgttaa tttcaactac gcgaccagct tattcaataa 360
atccaccatc cagggcttcc tgcacacata tgaatacctt ctgcgtcagc tgtccgaact 420
gagcgctgaa ggcatcaacg aagataccca gctgtcactg gttcgcccga ctgagaacgg 480
ggatctgcac ctgccactgg cccagtctcc gctcgcgacc actgcagaag aacagaaagt 540
tgcttccctg aaccaggctt tcgaacgtga agccttcctg gcggcggaaa aaatcgccgt 600
tgttcaaggg gaccgcgctc tgtcgtatgc cgacctgaac ggtcaggcta atcaactggc 660
gcgttatatc cagtccgtct cctgcatcgg tgccgacgac ggcatcgccc tgatgctgga 720
aaagagcatc gatactatca tctgcattct ggcaatctgg aaagcaggcg ccgcgtatgt 780
gccgctggat ccgacctacc caccaggccg tgtacaactg atcctggagg aaatcaaagc 840
gaaagctgtg ctggtacact cttcccacgc ctctaaatgt gaacgtcacg gtgc 894

<210> SEQ ID NO 282
<211> LENGTH: 1325
<212> TYPE: DNA
<213> ORGANISM: Artificial Sequence
<220> FEATURE:
<223> OTHER INFORMATION: Synthetic nucleotide

<400> SEQUENCE: 282
cctctaaatg tgaacgtcac ggtgccaaag tcattgcagt agactctccg gctattgaaa 60
cggcagtgag ccagcagtct gcagctgatc tgccgaccat tgctagcctg ggtaatctgg 120
catatatcat ctttactagc ggcacttctg gcaaaccgaa aggcgttctg gtagagcaaa 180
aagccgttct gctgctgcgc gacgccctgc gtgagcgtta cttcggtcgt gattgtacca 240
aacatcacgg tgttctgttc ctgagcaact acgttttcga cttctccgta gaacagctgg 300
ttctgtctgt actctcaggc cacaaactga ttgtcccgcc ggcggagttt gtggcggatg 360
acgaattcta tcgtatggcc tctacccacg gtctttctta cctgtctggc accccgagcc 420
tgcttcaaaa aatcgatctg gcacgtctgg atcacctgca ggttgtaacc gcggcgggtg 480
aggaactcca cgcgacccag tacgaaaaaa tgcgtcgtcg ttttaacggt ccaatctaca 540
acgcttatgg tgttaccgag acaacggtgt acaacatcat cgctgaattc accaccaact 600
ccatcttcga aaacgcatta cgcgaagtcc tgccgggcac ccgtgcgtac gttctgaacg 660
cggcgctgca gccggttcca ttcgacgctg tgggtgaact gtatctggcc ggcgatagcg 720
taacccgtgg ttacctgaac cagccgttgc tgaccgatca gcgtttcatc cctaacccgt 780
tctgcaagga agaagacatc gcgatgggtc gtttcgctcg tctgtacaaa accggcgacc 840
tggttcgctc tcgcttcaac cgccagcagc agccgcagct ggaatacctg ggccgtggcg 900
acctgcagat taaaatgcgt ggttaccgca ttgaaattag cgaagtacag aacgtgctga 960
cctcctcccc gggcgtacgc gaaggtgcgg ttgtggctaa atatgaaaac aacgacacgt 1020
atagccgtac tgcacattcc ttagtcggtt attataccac tgataacgaa acagtttcag 1080
aagctgatat cctcaccttc atgaaagcgc gtctgccgac ctatatggtg ccttctcacc 1140
tgtgctgcct ggaaggtgct ctgccagtca ctattaacgg taaactggac gttcgtcgtc 1200
tgcctgaaat tatcaacgac agtgcgcaat cctcatattc cccgccgcgc aacattatcg 1260
aagcgaaaat gtgccgttta tgggaaagcg cgctgggtat ggaacgctgc ggtattgacg 1320
atgac 1325

<210> SEQ ID NO 283
<211> LENGTH: 1251
<212> TYPE: DNA
<213> ORGANISM: Artificial Sequence
<220> FEATURE:
<223> OTHER INFORMATION: Synthetic nucleotide

<400> SEQUENCE: 283
cgtttatggg aaagcgcgct gggtatggaa cgctgcggta ttgacgatga cctcttcaag 60
ctgggggggg attctatcac cagtctgcac ctcgtcgcac agattcacaa tcaggtgggc 120
tgtaagatta ccgtgcgcga tattttcgaa caccgtaccg cgcgtgctct ccacgatcac 180
gttttcatga aggatagcga tcgctctaac gtcacccagt tccgtaccga gcaggggccg 240
gtcattggcg aagctccgct gctgccgatc caggattggt tcttgagcaa agctctgcag 300
caccctatgt actggaacca cacgttctac gtacgtaccc cggaactgga cgttgattcc 360
ctgagtgcgg ccgttcgtga cctgcagcag taccacgacg ttttccgcat gcgcctgaaa 420
cgcgaagaag ttggctttgt acagtccttt gccgaagact ttccccggc gcagctgcgt 480 gtactgaacg tgaaggacgt ggatggtagc gcggcggtta acgaaatcct ggacggttgg 540
caaagcggct tcaacctgga aaacggtccg atcggctcga tcggttatct gcatggctat 600
gaagaccgct ccgcacgtgt gtggttttct gtacaccaca tggccattga cactgtttcc 660
tggcagatcc tggttcgtga tctgcagact ctgtaccgta acggttccct gggttccaaa 720
ggttcttcat ttcgccaatg ggccgaggca atccaaaact acaaagcgag cgactcggaa 780
cgtaaccatt ggaacaagct ggttatggaa actgcatcgt cgatcagcgc gctgccgacc 840
tccactggtt ctcgcgtacg tctctcccgt tctctgtctc ctgaaaaaac tgcttctctg 900
atccagggtg gcatcgatcg tcaggatgta agcgtatacg attctctgct gacttctgtt 960
ggcctggctt tgcaacacat cgcgccgact ggcccgtcta tggttacaat cgagggtcac 1020
ggccgcgaag aagttgacca gaccctggat gtttctcgta cgatgggctg gttcactacc 1080
atgtatccgt tcgaaatccc gcgtctgtcg acggaaaaca tcgtgcaggg tgttgttgct 1140
gtaagtgaac gcttccgcca agttccggct cgcggtgttg gttatggtac tctgtacggt 1200
tacacccagc accctctgcc gcaggttact gttaactacc tgggccagct g 1251

<210> SEQ ID NO 284
<211> LENGTH: 1076
<212> TYPE: DNA
<213> ORGANISM: Artificial Sequence
<220> FEATURE:
<223> OTHER INFORMATION: Synthetic nucleotide

<400> SEQUENCE: 284

-continued

```
acacccagca ccctctgccg caggttactg ttaactacct gggccagctg gctcgtaaac     60
agagcaagcc gaaagaatgg gttctggcag ttggtgataa cgagttcgag tacggtctga    120
tgacctcccc ggaggataag gaccgttcga gctccgcagt ggatgttacg gccgtctgca    180
tcgacgggac gatgatcatc gatgtggact cggcttggtc tttggaagaa tctgaacagt    240
tcatctcgtc aattgaagaa ggtctgaaca aaatcctgga cggtcgtgca tcccagcaga    300
ctagccgctt tccggatgtg ccgcagccag cagagaccta caccccatac ttcgaatatc    360
tggaaccgcc gcgccagggc ccgaccctgt ttctgctgcc accgggtgaa ggtggtgcgg    420
aatcttactt caacaacatc gtcaaacgct tgcgtcaaac taacatggtt gtctttaaca    480
actactacct gcactccaaa cgtctgcgca ccttcgagga actggctgaa atgtatctgg    540
accaggtacg cggcatccaa ccgcacggtc cataccactt catcggctgg agcttcgggg    600
gcattctggc gatggagatg tcccgtcgtc tggttgcgag cgacgaaaaa attggttttc    660
tgggtattat cgacacctat ttcaacgtac gtggtgccac tcgcaccatt ggccttggtg    720
atactgaaat cctggatccg atccaccaca tctataaccc ggacccggca aactttcagc    780
gtctgccgtc tgccaccgac cgtatcgtcc tgtttaaggc catgcgtccg aataataaat    840
atgaatcaga aaaccagcgt cgcctgtatg agtactacga cgcgttagat tccacggact    900
ggaccgcatg ttaccaggcg atccctacct cctcatggtc gcgcctgcgc acgatccaca    960
ccttcccggg ttcggaaatc cacaaccgct ggtcccgttg cgttcgtctg agccgtaaca   1020
ccagccttgc catcgacccg tctctggcgg ctcagtacat cggtcgttgg aagtaa       1076
```

METHOD OF PREPARING NUCLEIC ACID MOLECULES

CROSS REFERENCE TO PRIOR APPLICATIONS

This application is a National Stage Application of PCT International Patent Application No. PCT/KR2012/006147 filed on Aug. 1, 2012, under 35 U.S.C. §371, which claims priority to Korean Patent Application No. 10-2011-0076408 filed on Aug. 1, 2011, which are all hereby incorporated by reference in their entirety.

FIELD OF THE DISCLOSURE

The present disclosure relates to a method of preparing nucleic acid molecules, and more specifically to a method that enables efficient synthesis of long nucleic acid molecules.

BACKGROUND

Typically employed DNA synthesis procedures for scalable DNA construction have the following disadvantages: (a) high cost of oligonucleotides, (b) low assembly efficiency into long DNA sequences, (c) time-consuming cloning, and (d) high cost of target DNA sequence validation. Above all, the major synthesis costs are the costs of oligonucleotides and sequencing. It would thus be desirable to design a protocol for massively parallelizing synthesis products in order to achieve effective, highly scalable DNA synthesis. DNA oligonucleotides derived from DNA microchips have previously been utilized to synthesize scalable low-cost DNA (Tian, J., et al., 2004). However, the low assembly efficiency of chip-derived oligonucleotides hinders target gene construction, and a laborious DNA assembly optimization process is consequently required. The inefficiency of DNA assembly from chip-derived oligonucleotides is largely associated with the incomplete removal of flanking regions of double-stranded (ds)-oligonucleotides prior to their assembly and the uneven concentration of each chip-cleaved oligonucleotide (Kim H., et al., 2011). Furthermore, it was observed that a greater number of oligonucleotides (i.e. higher complexity) in a DNA assembly pool made DNA assembly less efficient (Kim H., et al., 2011; Borovkov A. Y., et al., 2010). As a consequence, only a small sub-pool of oligonucleotides (i.e. <20) are often amplified to ensure high assembly efficiency. There is a need to develop a high-efficiency DNA assembly process using a large number of microchip oligonucleotides present in a pool in order to attain all advantages of ultra-low cost DNA microchip oligonucleotides.

For scalable DNA synthesis, it is preferable to decrease the sequencing cost for target DNA validation. In recent years, costs for high-throughput sequencing technologies have been considerably lowered. Under such circumstances, utilization of high-throughput sequencing technology has great potential for DNA synthesis at ultra-low cost. However, unlike colony-based Sanger sequencing validation, it is difficult to collect the desired DNA from a pool of high-throughput sequenced DNA mixtures. Although recent high-throughput sequencing technologies can be applied to partially addressable spots (for example, clonal spots available from Roche-454, Illumina and SOLiD, and single-molecule spots available from Helicos and PacBio), it is difficult to isolate target DNA due to the difficulty associated with the collection of the desired DNA from high-throughput sequencing plates. In a notable report (Matzas M., et al., 2010), chip-cleaved oligonucleotides were sequenced by 454 sequencing technology, and directly isolated from the 454 sequencing plate using a bead picker pipette. These sequence-validated 'oligonucleotides' were subsequently processed and used to assemble 200 bp target DNA fragments. This study demonstrates the possibility of convergence of next-generation sequencing technology and microchip oligonucleotides in terms of DNA synthesis cost reduction. In this study, however, high-throughput sequencing was carried out on chip oligonucleotides rather than on assembled DNA fragments. Accordingly, challenges associated with DNA assembly into larger sequences are still in early stages. Furthermore, an effective error-free oligonucleotide picking process necessitates a highly tuned bead picking robot and an image processing system.

A number of papers and patent publications are referenced and cited throughout the specification. The disclosures of the papers and patent publications are incorporated herein by reference in their entireties in order to more fully describe the state of the art to which the present disclosure pertains and the disclosure of the present disclosure.

SUMMARY

According to one embodiment of the present disclosure, there is provided a method of preparing nucleic acid molecules, including (a) providing nucleic acid fragments constituting at least a portion of the complete sequence of a target nucleic acid, (b) tagging the nucleic acid fragments with barcode sequences, (c) validating the sequences of the nucleic acid fragments tagged with the barcode sequences, and (d) recovering desired nucleic acid fragments among the sequence-validated nucleic acid fragments using the barcode sequences.

According to a further embodiment of the present disclosure, there is provided a method of preparing nucleic acid molecules, including (a) providing nucleic acid fragments constituting at least a portion of the complete sequence of a target nucleic acid, (b) assembling the nucleic acid fragments to synthesize intermediates having sizes whose sequences are validatable by a parallel sequencing technology, (c) tagging the intermediates with barcode sequences, (d) validating the sequences of the intermediates tagged with the barcode sequences, (e) recovering desired intermediates among the sequence-validated intermediates using the barcode sequences, and (f) assembling the recovered intermediates to form long nucleic acid molecules.

According to another embodiment of the present disclosure, there is provided a method of preparing nucleic acid molecules, including (a) providing a pool of oligonucleotides containing restriction enzyme digestion sequences and generic flanking sequences, (b) cleaving the restriction enzyme digestion sequence portions to provide a pool of mixtures including the oligonucleotides, each containing the generic flanking sequences at one end, and the oligonucleotides, each containing none of the generic flanking sequences at one end, and (c) assembling the oligonucleotides using the generic flanking sequences to randomly synthesize nucleic acid fragments.

According to yet another embodiment of the present disclosure, a method of preparing nucleic acid molecules, including (a) providing a pool of oligonucleotides, (b) assembling the oligonucleotides to randomly synthesize nucleic acid fragments, (c) connecting base sequences for amplification to the randomly synthesized nucleic acid fragments, and (d) amplifying the nucleic acid fragments with primers bound to the base sequences for amplification.

DETAILED DESCRIPTION

Figure 1:
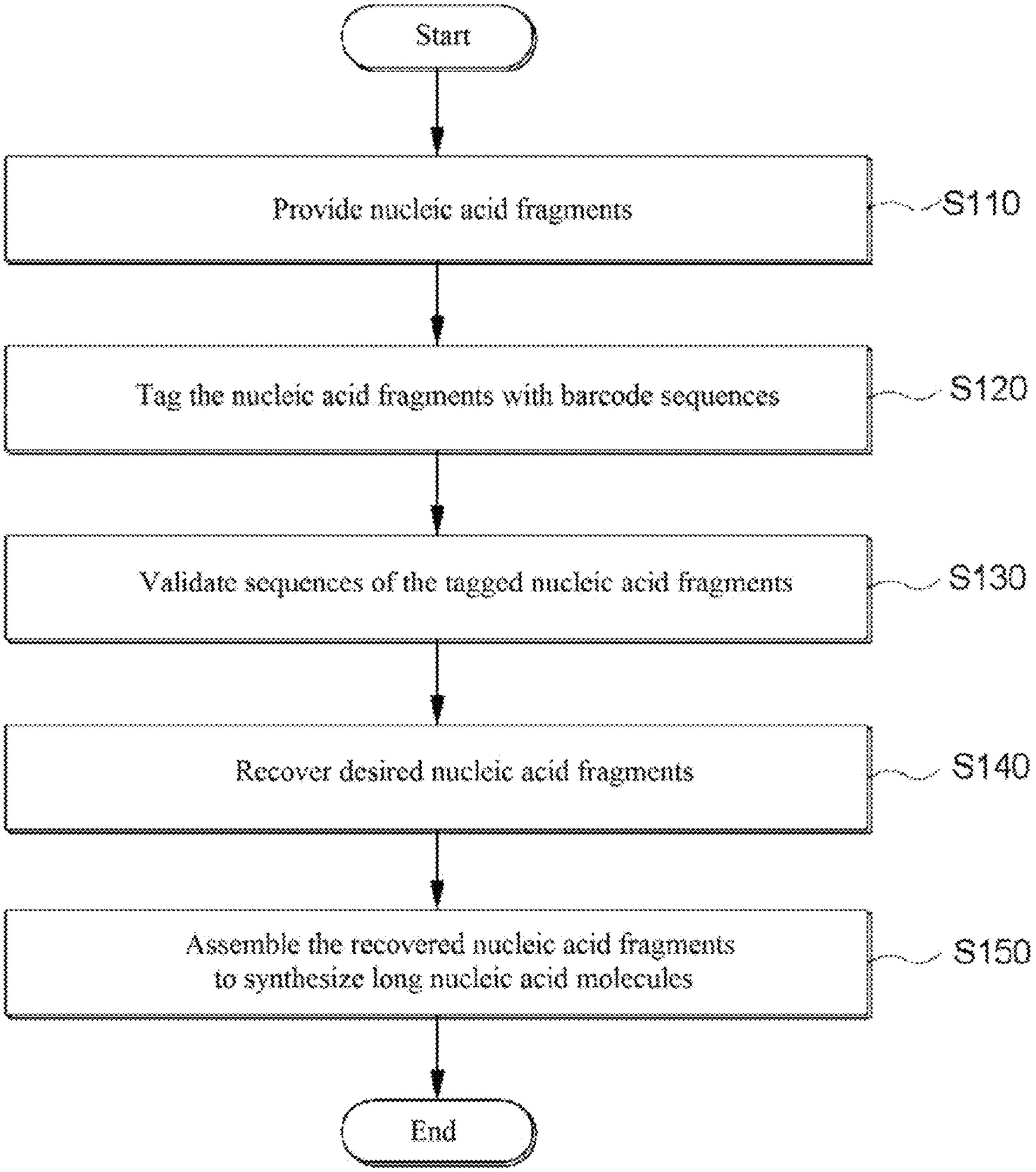
FIG. 1 is a flow chart illustrating a method of preparing nucleic acid molecules according to one embodiment of the present disclosure.

Embodiments of the present disclosure will now be described in more detail with reference to the accompanying drawings. These embodiments are provided so that this disclosure will fully convey the scope of the disclosure to those skilled in the art. Accordingly, the present disclosure may be embodied in many different forms and should not be construed as limited to the exemplary embodiments set forth herein. In the drawings, the dimensions, such as widths, lengths and thicknesses, of elements may be exaggerated for convenience. It will be understood that when a first element is referred to as being "connected" or "attached" to a second element, the first element can be directly connected or attached to the second element or a third element may also be interposed between the first and second elements.

FIG. 1 is a flow chart illustrating a method of preparing nucleic acid molecules according to one embodiment of the present disclosure. Referring to FIG. 1, in step S110, nucleic acid fragments constituting at least a portion of the complete sequence of a target nucleic acid are provided. The nucleic acid fragments may be naturally occurring or artificially synthesized ones. Preferably, the nucleic acid fragments are derived from DNA microchips providing several million kinds of base sequences at low costs or from a pool of synthetic oligonucleotides. The pool of synthetic oligonucleotides may be prepared by methods well known in the art. For example, the pool of synthetic oligonucleotides may be prepared from resin-based oligonucleotides but is not limited thereto. Preferably, the nucleic acid fragments are derived from DNA microchips.

When it is intended to synthesize large target nucleic acid molecules, the nucleic acid fragments may be ones that are free of sequence errors such as insertion, deletion, transition and transversion.

The nucleic acid fragments provided in step S110 may be directly extracted from a pool of oligonucleotides. Alternatively, the nucleic acid fragments may be prepared by amplifying and assembling oligonucleotides so as to have lengths above a predetermined level. When it is intended to synthesize long target nucleic acid molecules, the nucleic acid fragments may be made by various processes, including a hierarchical gene synthesis process (*Journal of Biotechnology* 151 (2011) 319-324) or a random gene synthesis process, which will be described below.

In the present specification, random gene synthesis is also referred to as "shotgun synthesis", and nucleic acid fragments made by such a shotgun synthesis method are also referred to as "shotgun products."

Shotgun sequencing is a process in which analyte DNA is randomly fragmented, sequencing adaptors are connected to the nucleic acid fragments, followed by high-throughput sequencing analysis. Shotgun sequencing includes arranging the individual fragments and identifying the complete sequence of the original analyte DNA using a computer program. Shotgun synthesis proceeds in the exact reverse order to that of the shotgun sequencing. Oligonucleotides constituting a portion of the sequence of nucleic acid molecules to be synthesized are constructed and assembled randomly to make nucleic acid fragments, which are analyzed by high-throughput sequencing. Desired nucleic acid fragments are recovered among the analyzed nucleic acid fragments and are used to make the final nucleic acid molecules.

According to one embodiment of the present disclosure, the nucleic acid fragments provided in step S110 may be shotgun products prepared by a shotgun synthesis method. Oligonucleotides designed to contain generic flanking sequences may be used to make the shotgun products.

Figure 2:
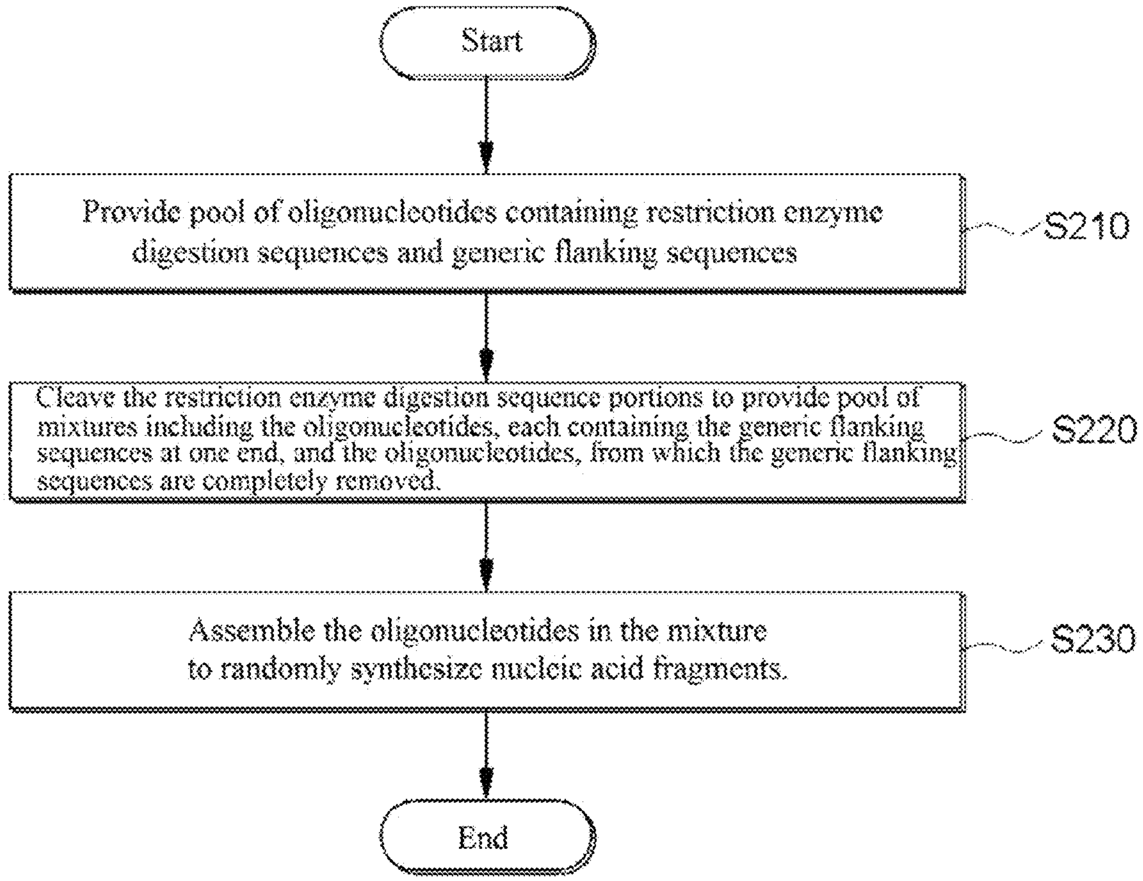
FIG. 2 is a flow chart illustrating a random gene synthesis process according to one embodiment of the present disclosure.

FIG. 2 is a flow chart illustrating a random gene synthesis process according to one embodiment of the present disclosure. Referring to FIG. 2, in step S210, a pool of oligonucleotides, each containing restriction enzyme digestion sequences and generic flanking sequences at at least one end, is provided. In step S220, the restriction enzyme digestion sequence portions are cleaved to provide a pool of mixtures including the oligonucleotides, each containing the generic flanking sequences at one end, and the oligonucleotides, each containing none of the generic flanking sequences at one end. In step S230, the oligonucleotides in the mixture are assembled using the generic flanking sequences to randomly synthesize nucleic acid fragments.

In step S210, the generic flanking sequence may exist at one or both ends of the oligonucleotide. For example, the oligonucleotides used in the random gene synthesis (shotgun synthesis) process may contain, from the 5' to 3' direction, 5'-end generic flanking sequences, the oligonucleotide sequences constituting the target nucleic acid, and 3'-end generic flanking sequences.

The 5'-end generic flanking sequences and 3'-end generic flanking sequences existing at the ends of the oligonucleotides are priming regions where the amount of the oligonucleotide derived from DNA chips is amplified, and are used as annealing regions of primer sets for the production of a sufficient amount of the oligonucleotides.

The oligonucleotides may contain restriction enzyme digestion sequences. The nucleic acid fragments contain 5'-restriction enzyme digestion sequences with the 5'-end generic flanking sequences, and 3'-restriction enzyme digestion sequences with the 3'-end generic flanking sequences. The 5'-restriction enzyme digestion sequences and the 3'-restriction enzyme digestion sequences in the oligonucleotides may be identical to or different from each other.

The oligonucleotides are 50-500 base pairs (bp), more preferably 100-300 bp, even more preferably 120-200 bp, most preferably about 150 bp in length.

According to one embodiment of the present disclosure, the oligonucleotides may contain portions or all of the sequence of the target nucleic acid. When the oligonucleotides contain portions of the sequence of the target nucleic acid, the target oligonucleotides with varying sizes are sequentially assembled to synthesize the target nucleic acid molecules containing all of the sequence.

The pool of the oligonucleotides may be one that is cleaved from DNA microchips. Alternatively, the pool of the oligonucleotides may be a mixture of oligonucleotides synthesized on a solid. The cleaved oligonucleotides may be amplified to ensure an amount necessary for long gene synthesis. This amplification may be perform by polymerase chain reaction (PCR) using the generic flanking sequences.

Next, the generic flanking sequences are cleaved using a restriction enzyme recognizing the restriction enzyme digestion sequences in the amplified oligonucleotides. The pool of the cleaved oligonucleotides may take the form of a mixture including the oligonucleotides, each containing none of the generic flanking sequences because the restriction enzyme digestion sequences at both ends are completely cleaved, and the oligonucleotides, each containing the generic flanking sequences remaining at one end because only the restriction enzyme digestion sequences at one end are cleaved.

The oligonucleotides of the mixtures can be assembled by polymerase chain reaction assembly (PCA) using the generic flanking sequences. At this time, the oligonucleotides are sequentially assembled to make fragments with varying lengths. Such fragments may be randomly assembled to each other. Thus, the small or large fragments may be randomly assembled at various locations in the PCR solution to synthesize longer fragments containing all or portions of the sequence of the target nucleic acid molecules. This assembly may proceed until the oligonucleotides, each containing the generic flanking sequence at one end, overlap each other to make nucleic acid fragments containing the generic flanking sequences at both ends.

Figure 3:
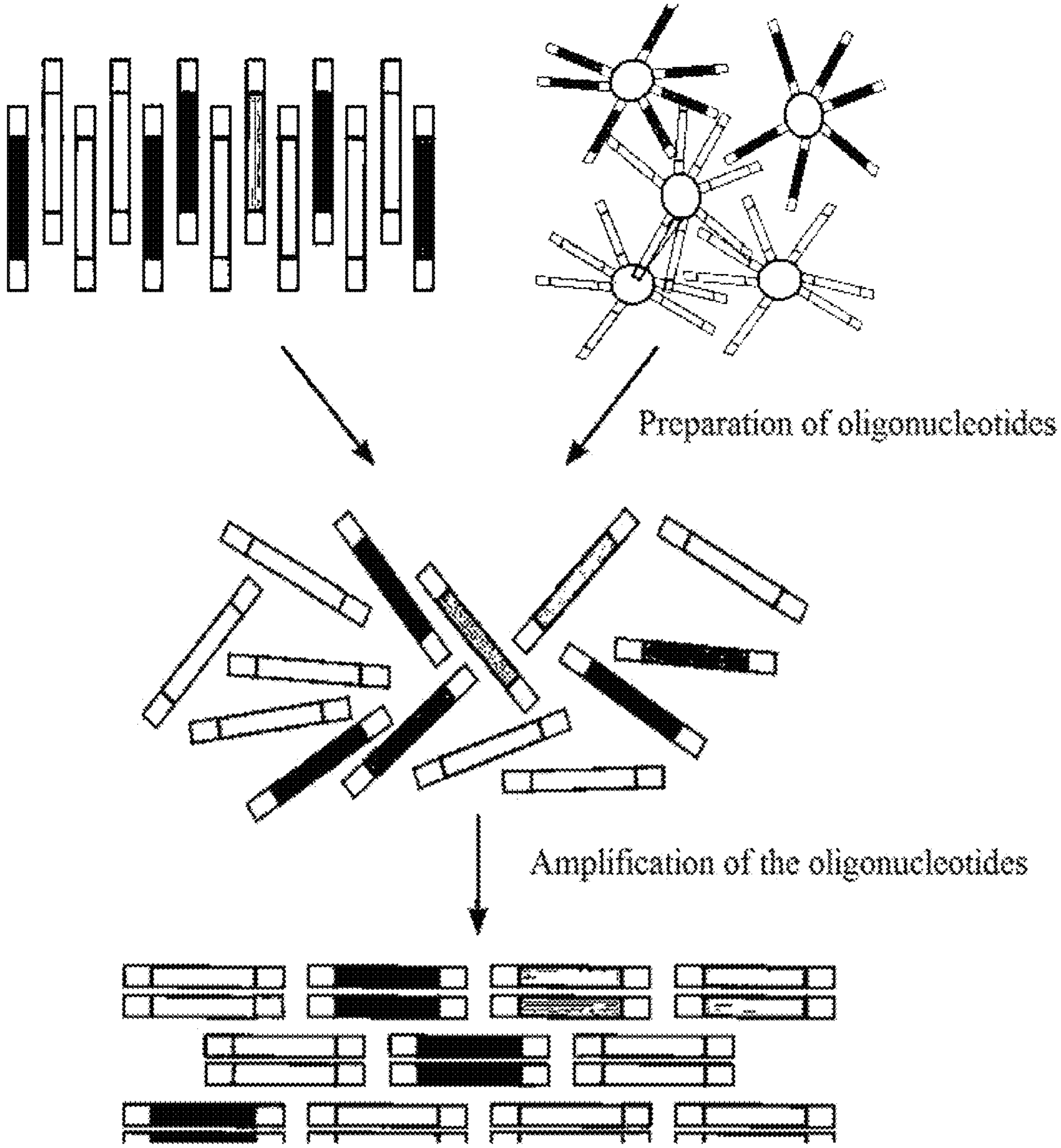
FIGS. 3 and 4 illustrate procedures for the synthesis of nucleic acid fragments by random synthesis processes.
Figure 4:
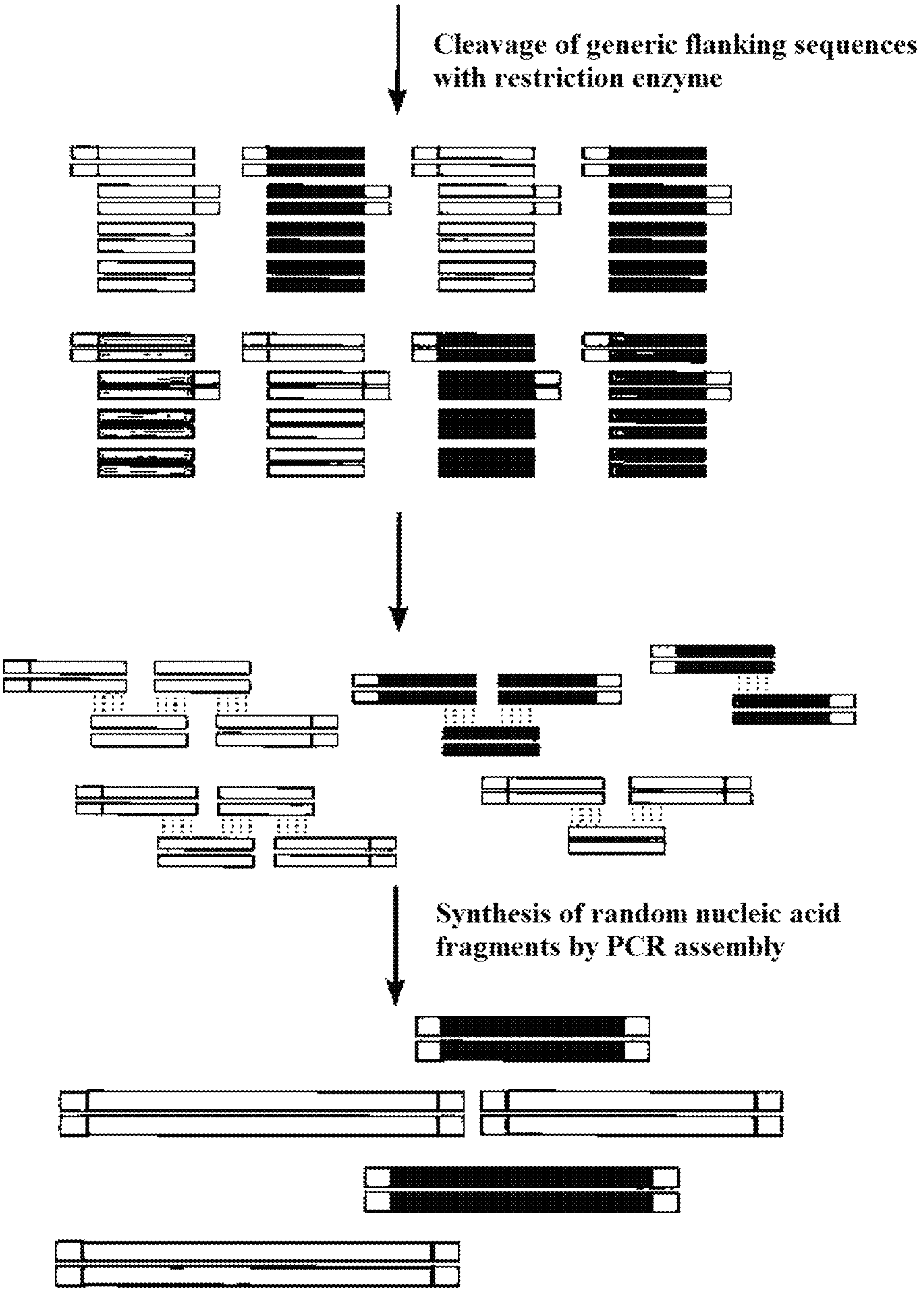

The oligonucleotides of step S210 are elaborately designed to form desired shotgun products. Several oligonucleotides may be assembled in such a manner that they overlap each other through some complementary sequences of the oligonucleotide sequences. The oligonucleotides are designed for random assembly to form shotgun products. For example, if a shotgun product (e.g., ~400 bp) containing the 5'-end regions of the target nucleic acid molecules consists of 5 target oligonucleotides, it may be formed through sequential assembly among the following oligonucleotides cleaved using restriction enzymes: from the 5' to 3' direction, to form a 5'-end region, a first oligonucleotide containing a 5'-end generic flanking sequence and a portion of the sequence of the target nucleic acid molecules and from which the restriction enzyme digestion sequences are partially cleaved; a second oligonucleotide including a region (e.g., 20-50 bp long) overlapping the 3'-end region of the first oligonucleotide; a third oligonucleotide including a region overlapping the 3'-end region of the second oligonucleotide; a fourth oligonucleotide including a region overlapping the 3'-end region of the third oligonucleotide; and a fifth oligonucleotide containing a sequence including a region overlapping the 3'-end region of the fourth oligonucleotide and a 3'-end generic flanking sequence. FIGS. 3 and 4 illustrate procedures for the synthesis of nucleic acid fragments by random synthesis processes.

In a modified embodiment, the nucleic acid fragments may be prepared by the following method.

First, a pool of oligonucleotides is provided. Next, raw oligonucleotides without the addition of generic flanking sequences, etc. are assembled to randomly synthesize nucleic acid fragments, unlike the previous embodiment. Base sequences for amplification are connected to the randomly synthesized nucleic acid fragment, and then the nucleic acid fragments are amplified with primers bound to the base sequences for amplification to obtain amplified nucleic acid fragments.

As described above, the preparation of nucleic acid molecules by random synthesis processes is advantageous in that several kinds of libraries of nucleic acid fragments can be prepared simultaneously.

According to one embodiment of the present disclosure, the nucleic acid fragments of step S110 may include the complete sequence of a target nucleic acid. For the synthesis of error-free long DNA, the sequences of the nucleic acid fragments may be validated using a parallel sequencing system. When the performance of the parallel sequencing system to validate the sequences of the nucleic acid fragments is taken into consideration, the nucleic acid fragments are preferably 20-3,000 bp, more preferably 200-1,000 bp, more preferably 300-500 bp, even more preferably 350-450 bp, most preferably 380-420 bp in length. Despite this preferred numerical range, an improvement in the performance of parallel sequencing systems for the analysis of several thousand by long DNA can extend the size of the nucleic acid fragments to several thousand by long DNA.

The term "nucleotide" as used herein refers to a single- or double-stranded deoxyribonucleotide or ribonucleotide and includes naturally occurring nucleotide analogs unless stated otherwise (Scheit, Nucleotide Analogs, John Wiley, New York (1980); Uhlman and Peyman, Chemical Reviews, 90:543-584 (1990)).

The term "oligonucleotide" as used herein refers to an oligomer or polymer of nucleotides or an analog thereof. According to one embodiment of the present disclosure, the gene amplification is carried out by PCR. According to one embodiment of the present disclosure, the primers (for example, the generic flanking sequences) are used in gene amplification reactions.

The term "amplification reactions" as used herein refers to reactions for amplifying target nucleic acid sequences. Various amplification reactions were reported in the art and include, but are not limited to, polymerase chain reaction (PCR) (U.S. Pat. Nos. 4,683,195, 4,683,202, and 4,800,159), reverse transcription polymerase chain reaction (RT-PCR) (Sambrook et al., Molecular Cloning. A Laboratory Manual, 3rd ed. Cold Spring Harbor Press (2001)), the methods of Miller, H. I. (WO 89/06700) and Davey, C. et al. (EP 329, 822), multiplex PCR (McPherson and Moller, 2000), ligase chain reaction (LCR) (17, 18), Gap-LCR (WO 90/01069), repair chain reaction (EP 439,182), transcription-mediated amplification (TMA) (19) (WO88/10315), self sustained sequence replication (20) (WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (APPCR) (U.S. Pat. Nos. 5,413,909 and 5,861,245), nucleic acid sequence based amplification (NASBA) (U.S. Pat. Nos. 5,130,238, 5,409, 818, 5,554,517, and 6,063,603), and strand displacement amplification (21, 22). Other possible amplification methods are described in U.S. Pat. Nos. 5,242,794, 5,494,810, and 4,988,617, and U.S. patent application Ser. No. 09/854,317.

In a most preferred embodiment of the present disclosure, the amplification procedure is carried out in accordance with PCR disclosed in U.S. Pat. Nos. 4,683,195, 4,683,202, and 4,800,159.

PCR is one of the most well-known nucleic acid amplification methods and many modifications and applications thereof have been developed. For example, traditional PCR procedures have been modified to develop touchdown PCR, hot start PCR, nested PCR, and booster PCR with improved PCR specificity or sensitivity. In addition, multiplex PCR, real-time PCR, differential display PCR (DD-PCR), rapid amplification of cDNA ends (RACE), inverse polymerase chain reaction (IPCR), vectorette PCR and thermal asymmetric interlaced PCR (TAIL-PCR) have been developed for specific applications. Details of PCR can be found in McPherson, M. J., and Moller, S. G. PCR. BIOS Scientific Publishers, Springer-Verlag New York Berlin Heidelberg, N.Y. (2000), the teachings of which are incorporated herein by reference. Examples of preferred target nucleic acid molecules that can be used in the present disclosure include, but are not particularly limited to, DNA (gDNA and cDNA) and RNA. DNA is more preferred. Examples of target nucleic acids suitable for use in the present disclosure include nucleic acids from prokaryotic cells, eukaryotic cells (e.g., protozoans, parasites, bacteria, yeasts, higher plants, lower animals, and higher animals, including mammals and humans), viruses (e.g., herpes virus, HIV, influenza virus, Epstein-Barr virus, hepatitis virus, and poliovirus), and viroids.

The primers used in the present disclosure are hybridized or annealed to sites of the template to form double-stranded structures. Suitable conditions of nucleic acid hybridization for the formation of such double stranded structures are described in Joseph Sambrook, et al., Molecular Cloning, A Laboratory Manual, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985).

A variety of DNA polymerases can be used for amplification in the present disclosure and include "Klenow" fragment of *E. coli* DNA polymerase I, thermostable DNA polymerases, and bacteriophage T7 DNA polymerase. Preferred are thermostable DNA polymerases that can be obtained from a variety of bacterial species, including DNA polymerases and Phusion polymerases of *Thermus aquaticus* (Taq), *Thermus thermophilus* (Tth), *Thermus filiformis, Thermis flavus, Thermococcus literalis, Pyrococcus furiosus* (Pfu), *Thermus antranikianii, Thermus caldophilus, Thermus chliarophilus, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana* and *Thermosipho africanus*. Most preferably, *Pyrococcus furiosus* (Pfu) or Phusion high-fidelity DNA polymerase is used.

When the polymerization reaction is carried out, it is preferred to provide excessive amounts of the components necessary for amplification to a reaction vessel. The excessive amounts of the components necessary for amplification refer to amounts of the components in which the amplification reaction is not substantially limited by the concentrations of the components. It is desirable to provide, to the reaction mixture, cofactors such as $Mg^{2+}$ and dATP, dCTP, dGTP and dTTP in amounts sufficient to reach a desired degree of amplification. All enzymes used in the amplification reaction may be active under the same reaction conditions. Indeed, a buffer allows all enzymes to reach their optimum reaction conditions. Thus, the use of a buffer enables the amplification of a single reactant without any change in reaction conditions such as the addition of other reactants.

In the present disclosure, annealing is carried out under stringent conditions that allow for specific binding between the target nucleotide sequences (e.g., the generic flanking sequences of the target oligonucleotides) and the primers. The stringent annealing conditions are sequence-dependent and vary depending on ambient environmental parameters. The oligonucleotide pool thus amplified can be used to make primary amplification products. The primary amplification products can be used to prepare secondary amplification products, which can be assembled into larger target nucleic acid molecules (e.g., ≥10 kb).

The term "primer" as used herein refers to an oligonucleotide that can act as a point of initiation of synthesis when placed under conditions in which synthesis of a primer extension product complementary to a nucleic acid strand (a template) is induced, i.e., in the presence of nucleotides and a polymerase, such as DNA polymerase, and under appropriate temperature and pH conditions. Preferably, the primer is deoxyribonucleotide and a single strand. The primers used in the present disclosure may include naturally occurring dNMP (i.e., dAMP, dGMP, dCMP and dTMP), modified nucleotides, and non-naturally occurring nucleotides. Other examples of the primers include ribonucleotides.

The primers should be sufficiently long to prime the synthesis of extension products in the presence of a polymerase (such as DNA polymerase). The length of the primers may vary depending on many factors, e.g., temperature, application, and sources of the primers. The primers are typically 15-30 nucleotides long. Short primer molecules generally necessitate a lower temperature to form sufficiently stable hybridization composites with templates.

The term "annealing" or "priming" as used herein refers to the apposition of an oligodeoxynucleotide or nucleic acid to a template nucleic acid. The apposition enables the polymerase to polymerize nucleotides into a nucleic acid molecule complementary to the template nucleic acid or a portion thereof. The term "hybridization" as used herein refers to a process in which two single-stranded nucleic acids form a duplex structure by pairing of complementary base sequences. The hybridization may occur when complementarity between single-stranded nucleic acid sequences is perfectly matched or even when partially mismatching bases are present. The degree of complementarity necessary for hybridization may vary depending on hybridization reaction conditions, particularly temperature.

The term "complementary" as used herein means a level of complementarity sufficient to selectively hybridize with the nucleotide sequence under certain particular hybridization or annealing conditions, and is intended to include both substantially complementary and perfectly complementary, preferably perfectly complementary.

Referring back to FIG. 1, in step S120, the nucleic acid fragments are tagged with barcode sequences. The barcode sequences are introduced into the nucleic acid fragments to recover error-free fragments or other desired fragments among the nucleic acid fragments provided in the previous step or to selectively amplify and assemble them in order to synthesize target nucleic acid molecules. The barcode sequences may be added to the generic flanking sequences present at the ends of the nucleic acid fragments.

The kinds of the barcode sequences are not particularly limited so long as they can be added to distinguish the nucleic acid fragments from each other. The number of the kinds of the barcode sequences is preferably greater than that of the nucleic acid fragments to distinguish the individual nucleic acid fragments. For example, the barcode sequences may be mixtures of two or more kinds of randomly or intentionally designed oligonucleotides.

According to one embodiment of the present disclosure, poly-N degenerate-barcode sequences among the barcode sequences may use poly-N degenerate DNA or may also use sequences barcoded with two or more different sequences randomly made using a computer program well known in the art.

The tagging with the barcode sequences is not particularly limited and may be performed by a method selected from the group consisting of PCR, emulsion PCR and ligation. For example, assembly of the barcode sequences to shotgun synthesized DNA fragments by PCR or ligation of double-stranded (ds) DNA including poly-N degenerate-barcode sequences may be used for the tagging.

Figure 5:
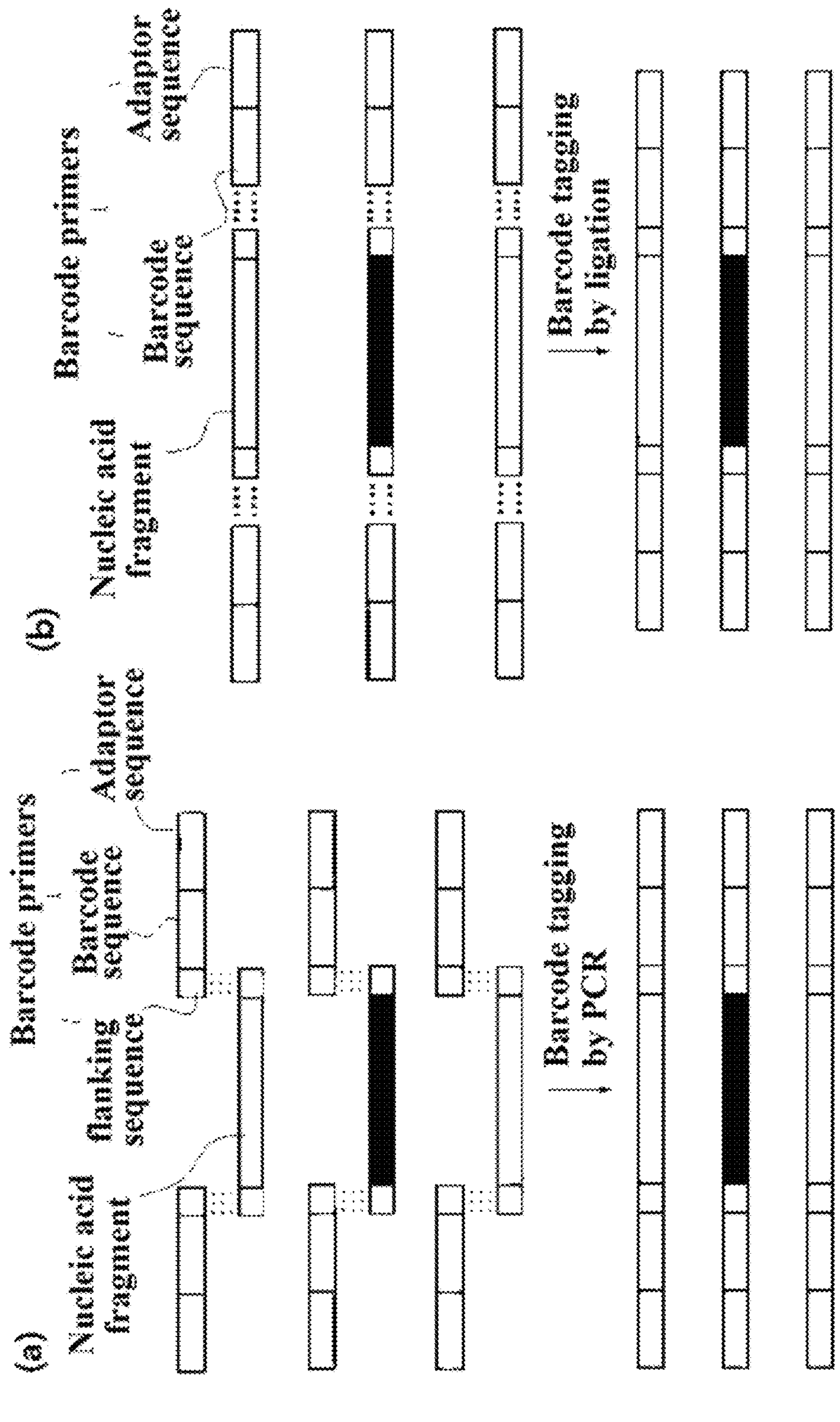
FIG. 5 illustrates two procedures for tagging nucleic acid fragments with barcode sequences according to embodiments of the present disclosure.

FIG. 5 illustrates two procedures for tagging nucleic acid fragments with barcode sequences according to embodiments of the present disclosure. (a) and (b) of FIG. 5 illustrate barcode tagging procedures by PCR and by ligation, respectively.

In step S130, the sequences of the nucleic acid fragments tagged with the barcode sequences are validated. Parallel sequencing is preferably used to validate the sequences of the tagged nucleic acid fragments. As a result, the sequences of the tagged nucleic acid fragments, together with the tagging barcode sequences, can be validated.

According to one embodiment of the present disclosure, the parallel sequencing or high-throughput sequencing is carried out by a suitable method well known in the art, for example, using a Roche-454 sequencing system or a high-throughput sequencing system with a read length of 100 bp or more.

According to one embodiment of the present disclosure, sequencing adaptor sequences may be further added to the barcode sequences. Sequences containing the barcode sequences added to the nucleic acid fragments are herein referred to as "barcode primers" for convenience.

The term "adaptor sequences" as used herein refers to sequences that enable high-throughput sequencing analysis of the nucleic acid fragments. For example, the adaptor sequences includes all commercially available sequences for 454-sequencing used in the present disclosure. Examples of preferred adaptor sequences include, but are not limited to, adaptor sequences of Roche-454 sequencing platforms and adaptor sequences of other next-generation sequencing technologies.

The term "generic flanking sequences" as used herein refers to base sequences that are added to both ends of the oligonucleotides to selectively amplify particular oligonucleotides among the pool of oligonucleotides. The base sequences added to the 5'-ends of different oligonucleotides necessary for assembly into target nucleic acid molecules are identical to each other, and the base sequences added to the 3'-ends of different oligonucleotides are identical to each other.

According to one embodiment of the present disclosure, an amplification procedure using the primers bound to the adaptor sequences may be performed using the tagged nucleic acid fragments as templates for sequence validation.

The barcode sequences are not limited to particular lengths and are, for example, 5-300 bp, preferably 10-100 bp, more preferably 12-40 bp, even more preferably 15-30 bp in length taking into consideration the sequencing performance on the entire sequences including the nucleic acid fragments. This numerical range may vary with the advance of sequencing technologies. For example, when the poly-N degenerate-barcode sequences are 20 bp long, $4^{20}$ kinds of the barcode sequences are possible.

The barcode primers may contain, for example, from the 5' to 3' direction, 454-adaptor sequences, poly-N degenerate-barcode sequences, restriction enzyme digestion sequences, and generic flanking sequences. The primers for amplification may be designed to bind to the 454-adaptor sequences.

The sequence validation enables identification of error-free nucleic acid fragments among the nucleic acid fragments and the barcode sequences added thereto.

On the other hand, the restriction enzyme digestion sequences contained in the barcode primers serve to remove the sequencing adaptor sequences of the nucleic acid fragments. The reason for this removal is because the presence of the adaptor sequences hinders subsequent assembly of the nucleic acid fragments because of attached beads in sequencing analysis.

In step S140, desired nucleic acid fragments are recovered among the sequence-validated nucleic acid fragments using the barcode sequences. The validation of the sequences of the desired nucleic acid fragments and the tagging barcode sequences by sequencing in the previous step enables recovery of the desired nucleic acid fragments using the barcode sequences. Specifically, the recovery step may be carried out by selectively amplifying the desired nucleic acid fragments with primers corresponding to the barcode sequences and recovering the amplified nucleic acid fragments. Alternatively, the recovery step may be carried out by selectively hybridizing the desired nucleic acid fragments with oligonucleotides corresponding to the barcode sequences and recovering the hybridized nucleic acid fragments. For example, the desired nucleic acid fragments may be error-free nucleic acid fragments.

The desired nucleic acid fragments may be recovered using a computer program. Specifically, the sequences of the nucleic acid fragments are imaginarily assembled using a computer program and are compared with the complete sequence of desired target nucleic acid molecules. Thereafter, primers synthesized based on the most optimized information on sequences flanking DNA fragments or primers hybridizing therewith can be used to recover the desired nucleic acid fragments.

According to one embodiment of the present disclosure, the computer program may be any of those known in the art. Examples of more preferred computer programs include in-house Python programs and programs constructed using Perl, C, C++ or other programming languages.

According to one embodiment of the present disclosure, the computer program is used to synthesize sequences complementary to the selected barcode sequences into oligos. Next, only error-free fragments capable of optimizing the synthesis of target DNA are recovered among the nucleic acid fragments (i.e. mixtures of erroneous fragments and error-free fragments) by amplification (PCR) or hybridization using the synthesized barcode oligos. Examples of methods for the recovery of error-free fragments using the synthesized barcode sequences include, but are not limited to, DNA capture methods using microchips and hybridization methods for recovering desired error-free fragments by attaching desired barcode sequences to biotinylated beads or magnetic beads, in addition to PCR.

According to one embodiment of the present disclosure, when the nucleic acid fragments are provided by shotgun assembly, the length of the error-free barcoded nucleic acid fragments may be 200 bp or more. When a next-generation sequencing system capable of analyzing DNA with 1,000 bp or more is used, the error-free barcoded nucleic acid fragments may be 1,000 bp or more in length. More preferably, the error-free barcoded nucleic acid fragments are from about 200 bp to about 10 kb or more in length.

In step S150, recovered nucleic acid fragments can be assembled to form long nucleic acid molecules.

According to one embodiment of the present disclosure, the target nucleic acid molecules prepared by the present disclosure include, but are not limited to, target genes, target gene clusters, target genomes, and natural or synthetic nucleic acid molecules.

The term "target gene cluster" or "target genome" as used herein refers to a cluster or genome that includes at least two genes encoding a desired target (gene). The cluster or genome may include cluster or genome regions capable of generating two or more gene products (e.g., genome regions including one or more multiple splicing products of the same gene).

According to one embodiment of the present disclosure, a target gene cluster or target genome that can be synthesized by the method of the present disclosure may have a length of about 10 kb or longer. For example, the target gene cluster or target genome may include a penicillin biosynthetic gene cluster DNA sequence (11,376 bp) from *Penicillium chrysogenum*, and the penicillin biosynthetic gene cluster may include pcbAB, pcbC, and penDE genes.

The term "natural or synthetic nucleic acid molecules" as used herein is intended to include DNA (gDNA and cDNA) and RNA molecules, and nucleotides as basic units of the nucleic acid molecules include not only natural nucleotides but also analogues having modified sugar or base moieties (Scheit, *Nucleotide Analogs*, John Wiley, New York (1980); Uhlman and Peyman, *Chemical Reviews,* 90:543-584 (1990)).

Figure 6:
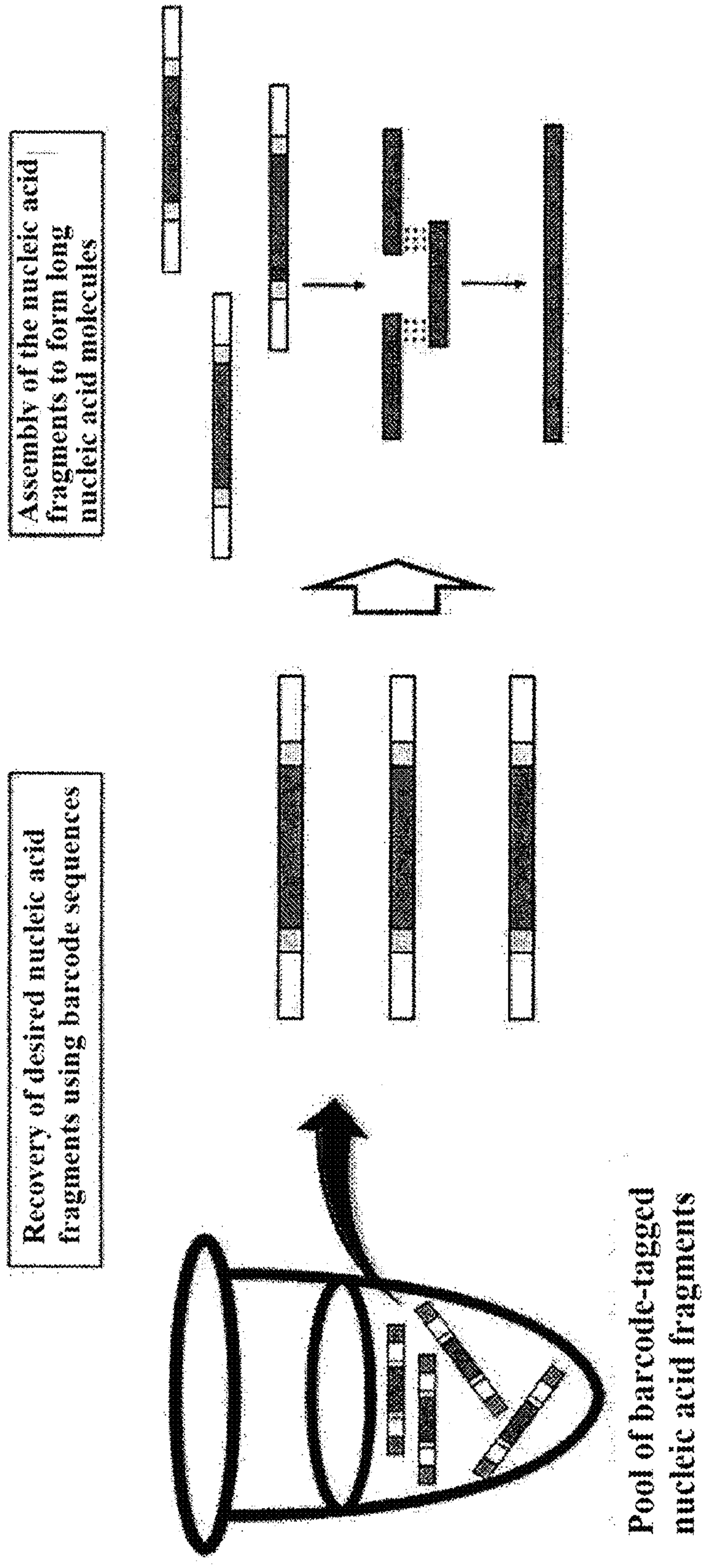
FIG. 6 illustrates a procedure for recovering desired nucleic acid fragments from a pool of barcode-tagged nucleic acid fragments and assembling the recovered nucleic acid fragments to form long nucleic acid molecules.

FIG. 6 illustrates a procedure for recovering the desired nucleic acid fragments from the pool of the barcode-tagged nucleic acid fragments and assembling the recovered nucleic acid fragments to form long nucleic acid molecules. According to one embodiment of the present disclosure, the nucleic acid molecules may be prepared by a method including the following steps.

Nucleic acid fragments constituting at least a portion of the complete sequence of a target nucleic acid are provided (step (a)). The size of the nucleic acid fragments provided in step (a) may be from 20 to 300 bp.

The nucleic acid fragments are assembled to synthesize intermediates having sizes whose sequences can be validated by a parallel sequencing technology (step (b)). The size of the intermediates is not particularly limited and may be, for example, from 50 to 3,000 bp. The intermediates may be increased to a desired size with the advance of parallel sequencing technologies such as next-generation sequencing technology. The intermediates may be synthesized by various synthesis processes, including hierarchical synthesis or random synthesis (shotgun synthesis).

The intermediates are tagged with barcode sequences (step (c)). Preferably, sequencing adaptor sequences are added to the barcode sequences for sequence validation.

The sequences of the intermediates tagged with the barcode sequences are validated (step (d)). The sequence validation of the intermediates tagged in step (d) may be performed by a parallel sequencing technology. The method may further include amplifying the tagged nucleic acid fragments using the sequencing adaptor sequences between steps (c) and (d).

Desired intermediates are recovered among the sequence-validated intermediates using the barcode sequences (step (e)). The desired intermediates may have error-free sequences.

The recovered intermediates are assembled to form long nucleic acid molecules (step (f)). The size of the long nucleic acid molecules may be 1,000 bp or more.

Figure 7:
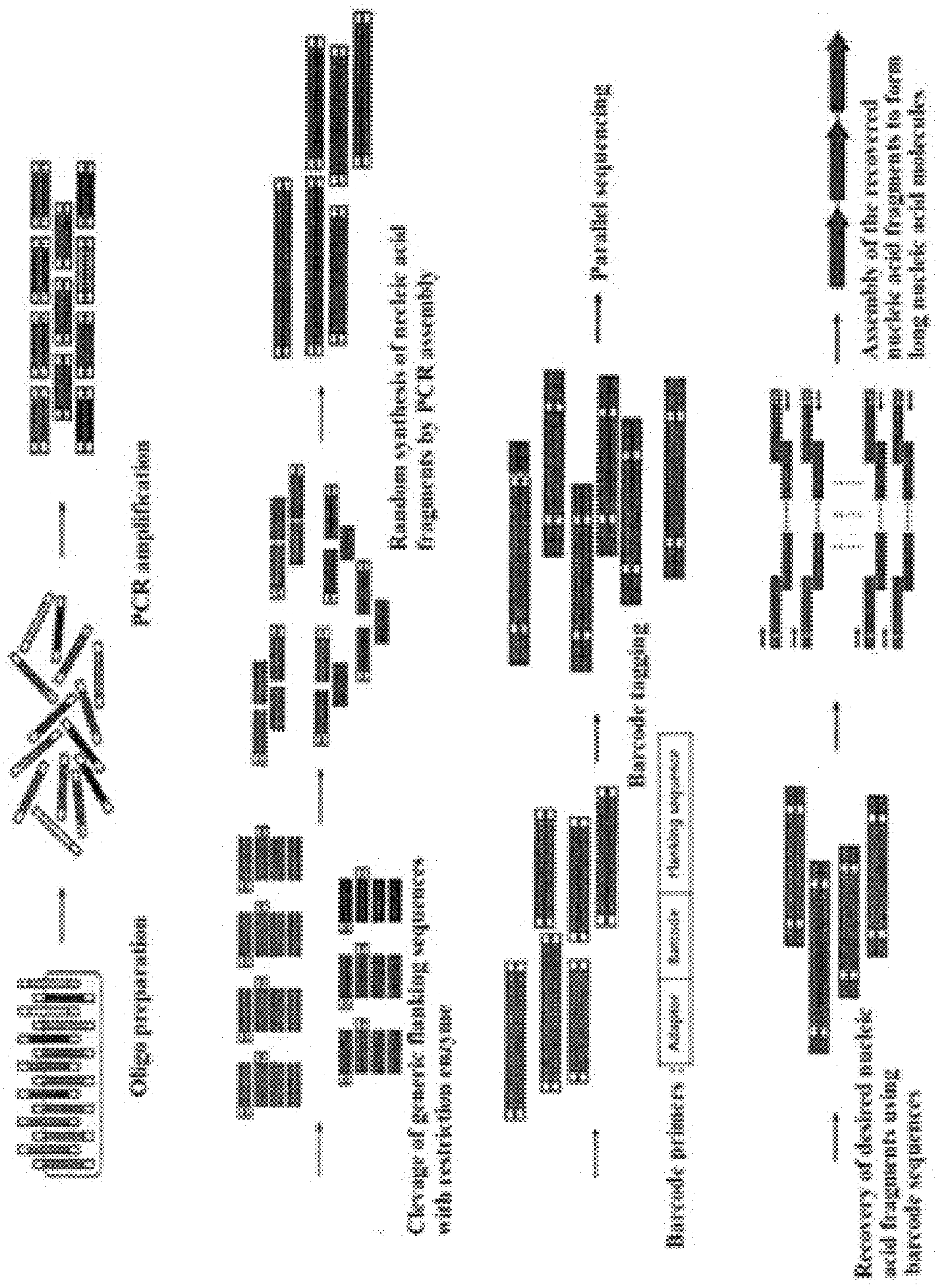
FIG. 7 schematically illustrates simultaneous utilization of a number of oligonucleotides for shotgun synthesis to obtain large target DNA molecules.

FIG. 7 schematically illustrates simultaneous utilization of a number of oligonucleotides for shotgun synthesis to obtain large target DNA molecules. Shotgun synthesis using about 200 oligonucleotides may cause random fragments with varying sizes of 100 bp (monomeric forms of oligonucleotides) to 1,000 bp. The assembly fragments in the form of intermediates are effectively barcoded by degenerate primers for high-throughput sequencing. The sequence-validated fragments are used in the subsequent assembly process.

Referring to FIG. 7, first, oligonucleotides are prepared from chips. The oligonucleotides are designed to have flanking sequences with Type IIS restriction enzyme sites (EarI or BtsI), and are synthesized on a DNA microarray. After oligonucleotides are cleaved from the chips, PCR amplification is carried out to increase the concentration of the oligonucleotides. The amplified oligonucleotides are cleaved using Type IIS restriction enzymes to remove the flanking sequences. Because the efficiency of the restriction enzymes is less than 100%, there are still uncut flanking sequences. Shotgun DNA assembly PCR using the remaining uncut flanking sequences is carried out to synthesize random fragments of the target genes. The sequences of the synthesized random fragments are analyzed by high-throughput sequencing technology. To this end, the synthesized fragments are tagged with the barcode primers using PCR. The PCR products are sequenced by 454 high-throughput sequencing and analyzed using an in-house Python program to identify error-free gene fragments and connected barcode sequences. To recover the error-free gene fragments, PCR is carried out from the pool of shotgun-assembled target gene fragments using barcode primer sequences. After removing the degenerate barcode sequences and flanking sequences from the recovered fragments by Type IIS restriction enzyme digestion, the error-free shotgun synthesis fragments are finally assembled into the full-length target gene.

Figure 8:
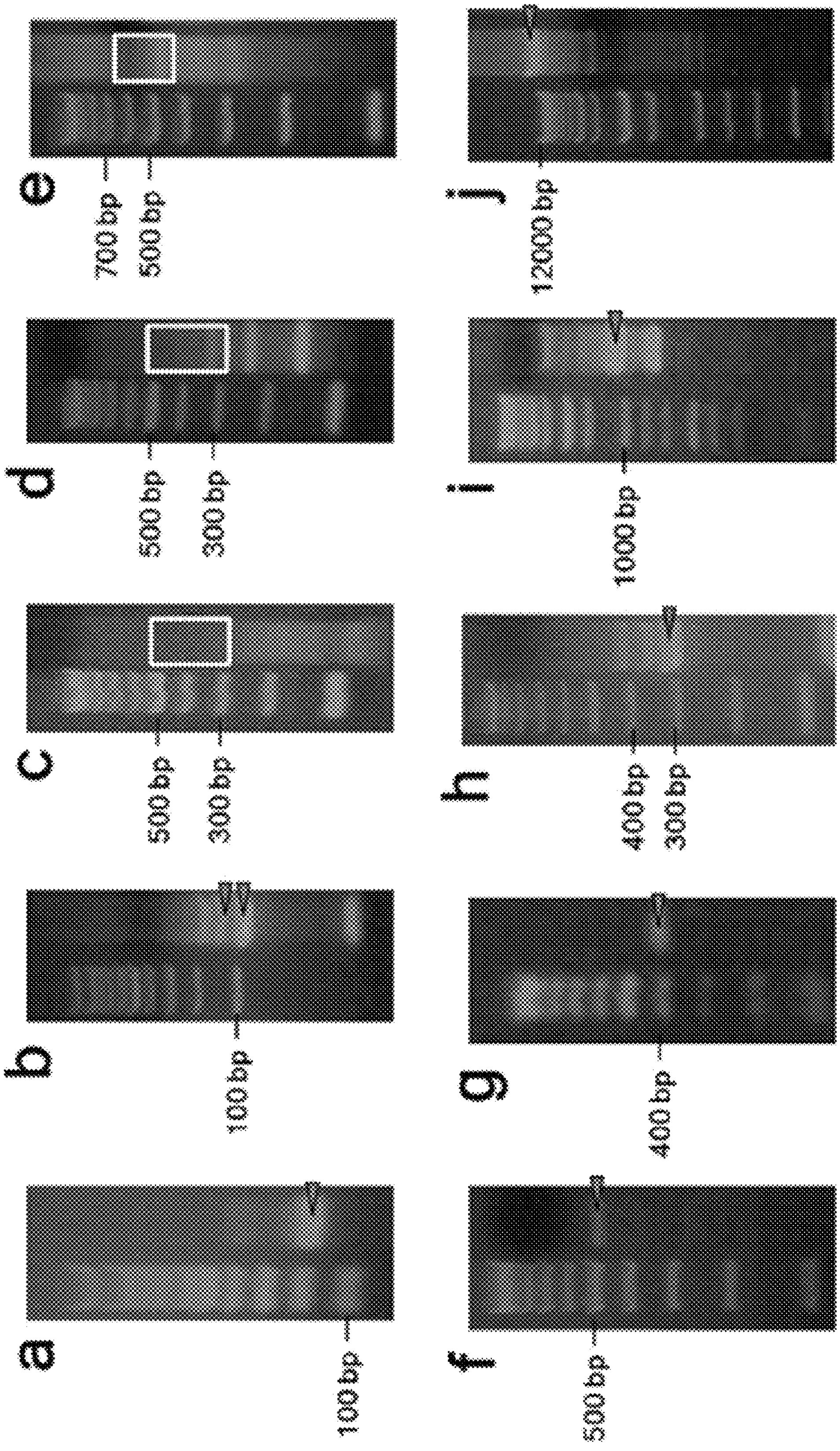
FIG. 8 shows PCR products produced in individual steps.

FIG. 8 shows PCR products produced in the individual steps. FIG. 8*a* shows PCR products produced by second round PCR using chip flanking primers. FIG. 8*b* shows results obtained after electrophoresis of the PCR products cleaved by Type IIS restriction enzyme in 4% agarose gel. The indicated two bands were excised and gel-purified together. FIG. 8*c* shows smear bands of PCR products assembled randomly using the Pen gene cluster fragments of FIG. 8*b*, which were amplified by chip flanking primers. The smear bands were excised and gel-purified. FIG. 8*d* shows PCR products obtained by re-amplification of the bands in the white box of FIG. 8*c* using chip flanking primers. The bands in the white box were excised and gel-purified. FIG. 8*e* shows smear bands obtained from PCR using barcode primers. The smear bands in the white box were excised and gel-purified. FIG. 8*f* shows products obtained by 100-fold dilution of the products obtained from the bands of FIG. 8*e* and amplification of the diluted products using 454-adaptor primers. If the concentration of the products obtained from the bands of FIG. 8*e* is excessively high, PCR is not conducted properly. The amplification products were excised, purified, diluted, cloned into TOPO vector, and submitted for Roche-454 sequencing. Daughter fragment 11-d produced by PCR was re-amplified with primers containing degenerate sequences. The resulting PCR amplification products are shown in FIG. 8*g*.

FIG. 8*h* shows three bands obtained by excising the bands shown in FIG. 8*g* with a Type IIS restriction enzyme. FIG. 8*i* shows Fragment 11 prepared by assembly of the bands shown in FIG. 8*h* and other daughter fragments. Fragment 11 is indicated by the arrow. FIG. 8*j* shows a final gene cluster obtained after assembly of 11 fragments.

Figure 9:
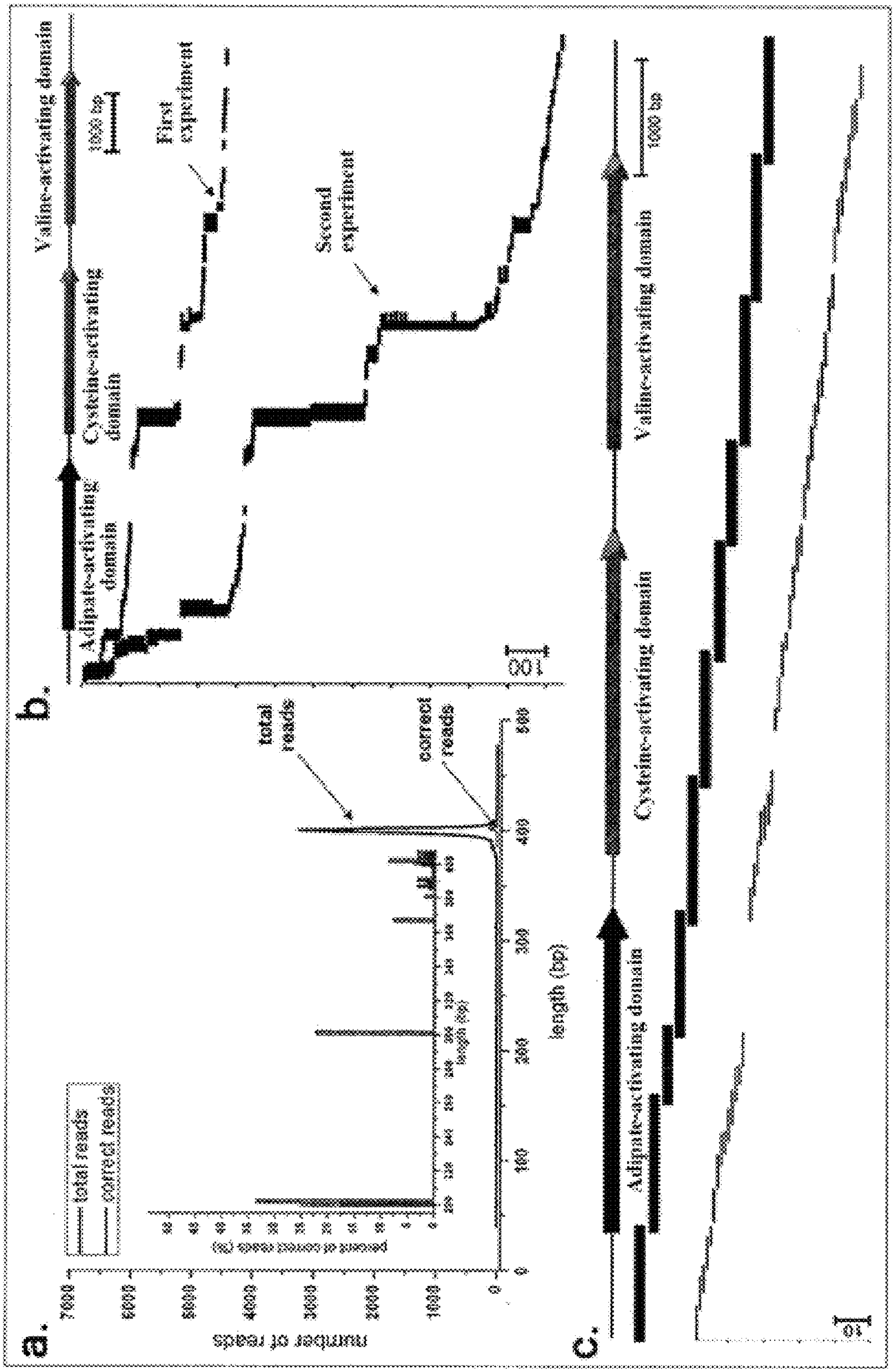
FIG. 9 shows computational analysis of 454 sequencing data from shotgun synthesis.

FIG. 9 shows computational analysis of 454 sequencing data from shotgun synthesis. FIG. 9*a* shows the number of 454 sequencing reads versus the length of the gene fragments. The upper and lower lines show the number of total 454 sequencing reads (total reads) and the error-free fragment reads (correct reads), respectively. The most abundant and correct reads have a length of 400 bp (they are typically 300 bp without barcode flanking regions). The inset in FIG. 9*a* shows that the percentage of error-free gene fragments tends to decrease as the length of the gene fragments increases. FIG. 9*b* shows computational analysis of two independent experiments (first and second experiments), and graphically aligned error-free gene fragments after the removal of the flanking barcode sequences. The first, second and third arrows on top of the figure represent clusters of genes (adipate-activating, cysteine-activating and valine-activating domains, respectively). The y-axis indicates the number of error-free gene fragments corresponding to various parts of the target gene. The scale bars at the bottom left and top right indicate 100 bp fragments and 1,000 bp base pairs, respectively. FIG. 9*c* shows the results of hierarchical shotgun synthesis. Optimized and selected gene fragments (~300 bp) were assembled into 1,000 bp gene fragments, which were then continuously assembled to synthesize the target gene (penicillin synthetic gene cluster (N-(5-amino-5-carboxypentanoyl)-L-cysteinyl-D-valine synthase); ~11.4 kb).

The foregoing embodiments of the present disclosure offer the following advantages.

The method of the present disclosure enables scalable synthesis of large target nucleic acid molecules in a more economical and efficient manner. According to the method of the present disclosure, amplification products containing the sequence of a target nucleic acid are prepared using an elaborately designed target oligonucleotide pool, 300-500 bp error-free shotgun assembly fragments are selectively recovered from the amplification products using barcode sequences, and larger target nucleic acid molecules (e.g., ≥~10 kb) are synthesized using the error-free shotgun assembly fragments. In addition, the method of the present disclosure enables gene synthesis at lower cost than conventional methods using resin-based oligonucleotides. Therefore, the present disclosure can be applied as a novel method for the synthesis of large target nucleic acid molecules and thus provides very excellent means that can considerably reduce gene synthesis cost.

The present disclosure will be explained in more detail with reference to the following examples. These examples are provided for illustrative purposes only and it will be obvious to those skilled in the art that are not intended to limit the scope of the present disclosure in accordance with the subject matter of the present disclosure.

EXAMPLES

Materials

AccuPrep™ gel purification kits for DNA purification and AccuPrep™ plasmid extraction kits for plasmid extraction were purchased from Bioneer (Korea). Pfu polymerase pre-mix and Taq polymerase pre-mix were purchased from Solgent (Korea). Phusion polymerase pre-mix, restriction enzymes [EarI (20,000 U/ml) and BtsI (10,000 U/ml)], NEB buffer 4(10) and competent cells (C-2566) were purchased from New England Biolabs (NEB) (USA). TOP Cloner™ Blunt core kits (6 TOP cloner buffer, sterile water, pTop blunt V2) were purchased from Enzynomics (Korea). Microchip oligonucleotides and primers were purchased from Agilent (USA) and Macrogen (Korea), respectively. Sanger sequencing and Roche-454 sequencing were requested to Macrogene (Korea).

Target Penicillin Biosynthetic Gene Cluster and Oligonucleotide Sequence Design

Penicillin biosynthetic gene cluster (N-(5-amino-5-carboxypentanoyl)-L-cysteinyl-D-valine synthase) DNA sequence (11,376 bp) from *Penicillium chrysogenum* was chosen as a synthetic model. A codon-optimized penicillin biosynthetic gene cluster sequence was designed using the web-based program Optimizer (Puigb, P. et al., 2007). Twenty-four nucleotides (5-GCAGAGTAAAGACCGTG-CACTTAT-3 SEQ ID NO: 1) were added to the microchip oligonucleotides.

Each Agilent chip oligonucleotide was 150 nucleotides in length and consisted of flanking sequences and target DNA sequences. Oligonucleotides (114 plus and 114 minus strands) for target DNA sequences were designed in such a way that upon annealing, complementary oligonucleotides contained overlapping regions for assembly. These 228 oligonucleotide sequences were flanked by generic PCR primer sequences.

Processing of Sub-Pools of Agilent Microchip Oligonucleotides

Lyophilized Agilent microchip oligonucleotides were suspended in 100 μl water. A higher concentration of the microchip oligonucleotide subpool (228 oligonucleotides targeting the penicillin biosynthetic gene cluster) was prepared using PCR amplification with flanking primers. The components included in each PCR reaction mixture were 8 μl water, 10 μl 2 Pfu polymerase pre-mix, 0.5 μl cleaved oligonucleotide pool, and 1 μl 10 μM forward and reverse primers. The first PCR reaction was performed as follows: (a) a pre-denaturation step at 95° C. for 3 min; (b) a 20-cycle PCR step, each cycle consisting of 95° C. for 30 s, 55° C. for 30 s, and 72° C. for 1 min; and (c) a final elongation step at 72° C. for 10 min. Thereafter, to amplify the oligos, the second PCR reaction was performed on the PCR products amplified by the first PCR reaction. For the PCR, the following reagents were used: 18 μl water, 25 μl 2 Pfu polymerase pre-mix, 3 μl of the first PCR products, and 2 μl 10 μM forward and reverse primers. The second PCR conditions were the same as for the first PCR reaction with the exception of the number of reaction cycles (i.e. 12). After verification of the desired products by 4% agarose gel electrophoresis, restriction enzyme digestion was carried out as follows: when EarI was used, 2.5 μl EarI, 5 μl NEB buffer, 0.5 μl 100×BSA and 50 μl PCR products were mixed, followed by digestion at 37° C. for 3 h; and when BtsI was used, 2.5 μl BtsI, 5 μl NEB buffer, 0.5 μl 100×BSA and 50 μl PCR products were mixed, followed by digestion at 55° C. for 3 h. The restriction digest products were electrophoresed through 4% agarose gels and gel-purified.

Shotgun Assembly

The gel-purified products were assembled using the first round shotgun assembly PCR. For the PCR, the following reagents were used: 20 μl Pfu polymerase pre-mix and 20 μl purified products (the sub-pool of 228 microchip oligonucleotides). The PCR conditions were as follows: a pre-denaturation step at 95° C. for 3 min; (b) a 36-cycle PCR step, each cycle consisting of 95° C. for 30 s, 60° C. for 30 s, and 72° C. for 1 min; and (c) a final elongation step at 72° C. for 10 min. After the PCR products were electrophoresed through an agarose gel (1.5%), gel regions (target size=~350 bp) of 300-500 bp were excised.

Processing of the Shotgun Assembly Products by Barcoding and 454 Sequencing

The detailed procedure is illustrated in FIG. 7. The gel-purified shotgun assembly fragments were amplified using flanking primers for PCR. For the PCR, the following reagents were used: 10 μl water, 25 μl Pfu polymerase pre-mix, 10 μl of the purified shotgun assembly fragments, and 2.5 μl 10 μM forward and reverse primers. The PCR conditions were as follows: (a) a pre-denaturation step at 95° C. for 3 min; (b) a 18-cycle PCR step, each cycle consisting of 95° C. for 30 s, 55° C. for 30 s, and 72° C. for 1 min; and (c) a final elongation step at 72° C. for 10 min. As a result, bands between 300 and 450 bp were excised and purified using an AccuPrep™ DNA purification kit (Bioneer, Korea).

The fragments were barcoded by a primer pair that consisted of, from the 5' to 3' direction, a 454 DNA sequencing-adaptor sequence, a 454 high-throughput sequencing key sequence (e.g., 5-TCAG-3), a 20-mer degenerate primer (i.e. made of poly N sites), an EcoP15I Type IIS restriction enzyme site, and the flanking primer sequences. The EarI or BtsI site was located at the 3' end of the flanking sequence of the chip oligonucleotides. The EcoP15I site was introduced into the PCR amplification procedure for shotgun assembly of the fragments using the barcoded primers. For the PCR, the following reagents were used: 6 μl water, 20 μl 2 Pfu polymerase pre-mix, 10 μl the assembled gene fragment pool, and 2 μl forward and reverse barcode primers. The PCR conditions were as follows: (a) a pre-denaturation step at 95° C. for 3 min; (b) a 18-cycle PCR step, each cycle consisting of 95° C. for 30 s, 55° C. for 30 s, and 72° C. for 1 min; and (c) a final elongation step at 72° C. for 10 min. After the PCR products were electrophoresed through an agarose gel (1.5%), the gel was excised to purify assembled fragments (450-600 bp). These gel-purified fragments were diluted 100-fold and the diluted products were then used for a final PCR amplification step involving 454 DNA sequencing-adaptor primers (Macrogene, Korea). For the PCR, the following reagents were used: 17.5 μl water, 25 μl Pfu, 2.5 μl of the 100-fold diluted gel-purified products and 2.5 μl forward and reverse primers. Eight replicate 20 μl PCR reaction products. The PCR reaction conditions were as follows: (a) a pre-denaturation step at 95° C. for 3 min; (b) a 25-cycle PCR step, each cycle consisting of 95° C. for 30 s, 71° C. for 30 s, and 72° C. for 1 min; and (c) a final elongation step at 72° C. for 10 min. Thereafter, the PCR products were electrophoresed through an agarose gel (1.5%), followed by gel purification (450-500 bp). The eight replicates were pooled prior to 454 sequencing.

Prior to 454 sequencing, cloning of the barcoded target gene fragments was performed, and several colonies were selected and submitted for Sanger sequencing evaluation. Gel-purified and barcoded products were cloned into the TOPO vector using the TOP Cloner™ Blunt core kit (Enzynomics, Korea). Competent cells derived from C2566 (New England Biolabs, USA), an *Escherichia coli* strain, were then transformed with the cloned products. After overnight growth on agar plates at 37° C., several colonies were chosen for colony PCR using M13F-pUC and M13R-pUC universal primer pairs. After confirmation of the presence of inserted DNA, Sanger sequencing was conducted prior to Roche-454 sequencing. Thereafter, the sequences of the gene fragments and the barcode primer sequences were validated using the Lasergene program (DNAstar, Madison, Wis.). After verification of the sequences, the pool of assembly PCR products was selected for Roche-454 high-throughput sequencing. The sequencing data were analyzed using an in-house Python program, and error-free gene fragments were selected.

Algorithm of In-House Python Program to Analyze the 454 High-Throughput Sequencing The primary task of the computer program was to select error-free shotgun assembly samples for subsequent assembly. The 454 sequencing read results (454 reads) were aligned to the target penicillin biosynthetic gene cluster sequence using the in-house Python programming language. DNA fragments with desired restriction enzyme sites (i.e. EcoP15I and either, EarI or BtsI sites) at both ends of the read were selected based on the sequencing data with a high quality score (Phred-like consensus quality >30, which corresponded to a base call accuracy >99.9%). Flanking sequences containing the enzyme site were eliminated from the processed gene fragments, and the flanking sequence-removed internal sequences were aligned to the target penicillin biosynthetic gene cluster sequence. When these internal sequences matched perfectly with the reference sequence, the aligned sequences were graphically listed along with their target gene cluster sequence (FIG. 9*b*). Subsequently, the program determined the optimal set of internal sequences that overlapped by more than 15 bp with other fragments necessary for subsequent assembly.

These selected gene fragments were recombined into the complete target gene (FIG. 9*c*). The Python scripts used for the analysis are available upon request.

Synthesis of the Target Gene Cluster from the Target Assembly Products

Amplification of the Desired Shotgun Assembly Products and Elimination of the Flanking Sequences from the Shotgun Assembly Products As described above, an in-house Python program was used to select optimum sets of shotgun assembly products. These overlapping error-free DNA fragments were selectively amplified from shotgun assembly DNA mixtures using selected barcode primer pairs. For the PCR, the following reagents were used: 8 μl water, 10 μl Phusion polymerase pre-mix, 1 μl forward and reverse barcode primers, and 1 μl of the shotgun assembly DNA mixture.

The PCR conditions were as follows: (a) a pre-denaturation step at 95° C. for 3 min; (b) a 30-cycle PCR step, each cycle consisting of 95° C. for 30 s, 60° C. for 30 s, and 72° C. for 1 min; and (c) a final elongation step at 72° C. for 10 min. The barcode primers are listed in Table 1.

Sequences of degenerate primers used for PCR recovery of error-free fragments

| Fragment (Daughter fragment) | CODE | Restriction enzyme used | Primer sequence Forward direction (5'→3') | Primer sequence Reverse direction (5'→3') | Nested PCR Primer sequence Forward direction (5'→3') | Nested PCR Primer sequence Reverse direction (5'→3') |
|---|---|---|---|---|---|---|
| 1-a | G2JQR9I0 7H3VM7 | EcoP15I from BtsI reaction pool | CTATTTGATGTT CGTAGTTCCAG (SEQ ID NO: 2) | AGCCTTTTCA AAGCGAAAG (SEQ ID NO: 3) | | |
| 1-b | G2JQR9I0 7H5WCJ | EcoP15I from EarI | ATCTATTAGGTC ATAGTAGGCAG | CATGCAGAGG AAACCATAAA | | |

-continued

Sequences of degenerate primers used for PCR recovery of error-free fragments

| Fragment (Daughter fragment) | CODE | Restriction enzyme used | Primer sequence Forward direction (5'→3') | Primer sequence Reverse direction (5'→3') | Nested PCR Primer sequence Forward direction (5'→3') | Nested PCR Primer sequence Reverse direction (5'→3') |
|---|---|---|---|---|---|---|
| | | reaction pool | (SEQ ID NO: 4) | (SEQ ID NO: 5) | | |
| 1-c | G2JQR9I07H38JU | Earl | TGCTATTCTTTC TGCCTTTTCAG (SEQ ID NO: 6) | GAATGTTTGT TGCGTTTCCA (SEQ ID NO: 7) | | |
| 1-d | G2JQR9I07IKM12 | EcoP15I from Earl pool | TCGAGCTCAAT AGTTTTTTCAG (SEQ ID NO: 8) | TTTATGATTGCA TTCAGCAGCAG (SEQ ID NO: 9) | | |
| 1-e | G2JQR9I06HC8AH | Earl | TTACTCCATTT TGCACTCTCAG (SEQ ID NO: 10) | ATTCTTTGGCC TTTGTTGACAG (SEQ ID NO: 11) | | |
| 2-a | G2JQR9I06HCZWA | Nest PCR from Btsl pool | TTAGTTTCAACATG TATATACAGCAGC (SEQ ID NO: 12) | ATGTGTATATTC GACACTTTCAGC (SEQ ID NO: 13) | GTGAATATCCG TCTAGCAAGC (SEQ ID NO: 14) | CAGTTCACGTTC GTCGCACACCAC (SEQ ID NO: 15) |
| 2-b | G2JQR9I06GYZ2I | EcoP15I from Btsl pool | CTATTTTCAG TGTGCCTTT (SEQ ID NO: 16) | TCCTAAGTTG ATGAAACTTT (SEQ ID NO: 17) | | |
| 2-c | G2JQR9I06GUX19 | Earl | TATCTGGTA GGAGGGGTT (SEQ ID NO: 18) | TAGAACTGGC AATGACGCTG (SEQ ID NO: 19) | | |
| 2-d | G2JQR9I06G2U2M | Earl | TTCTGTTTGT CTTAAATGCG (SEQ ID NO: 20) | TACCGTTTTT AAGATTGCGT (SEQ ID NO: 21) | | |
| 2-e | G2JQR9I07IH5UA | EcoP15I from Btsl pool | CTGAAATTCA TTTATGTTTG (SEQ ID NO: 22) | CTATGGGGT ACCTTTTTG (SEQ ID NO: 23) | | |
| 2-f | G2JQR9I06G01OD | EcoP15I from Earl pool | ATATTCGAGC GTATGTATTA (SEQ ID NO: 24) | AAGTGATTGT TTACAGTCTC (SEQ ID NO: 25) | | |
| 2-g | G2JQR9I07IKZ70 | EcoP15I from Earl pool | TCATTTCGAG AAAAGGCCGA (SEQ ID NO: 26) | GGGTTCTTTC CCTTATTTTG (SEQ ID NO: 27) | | |
| 3-a | G2JQR9I06HH7SE | Earl | AACGAGGATA TACAAATATA (SEQ ID NO: 28) | AAGTGTTGAG AGTGGTATAT (SEQ ID NO: 29) | | |
| 3-b | G2JQR9I07H5FTG | Earl | ATGGAGCTTT TATGTGGTTA (SEQ ID NO: 30) | AATTGTCTAG TTTCGTTGTT (SEQ ID NO: 31) | | |
| 3-c | G2JQR9I06GWSUY | EcoP15I from Btsl pool | TGTTGGTTGT TCAATGGAGT (SEQ ID NO: 32) | ATACTTGTTTCA ATTTTGTCCAGC (SEQ ID NO: 33) | | |
| 4-a | G2JQR9I06GX0BH | Nest PCR from Earl pool | TATTTTTTTCCA ATTTTTTACAGC (SEQ ID NO: 34) | ATCCTCTGCT ATTCTGTTGC (SEQ ID NO: 35) | ACCTGCATCCA GCTGATTGCGC GTATCCGTCAG CGTCAGCGTTT GTCTGTGTCTA TCTCTGTG (SEQ ID NO: 36) | GGGAAAGGGT GGTGTTGTAA (SEQ ID NO: 37) |
| 4-b | G2JQR9I07H7Z2P | Nest PCR from Earl pool | CTAATTTGAA TGCAGTCCGT (SEQ ID NO: 38) | ACATTACCTTT GGAAAAAACC (SEQ ID NO: 39) | CATGGAACAA AGTGATGCTT (SEQ ID NO: 40) | TCCAGCAGCT GGAAGACTT (SEQ ID NO: 41) |
| 4-c | G2JQR9I06HCPB7 | Nest PCR from Earl pool | TTAAGTATGAT TAATGCTGTCA (SEQ ID NO: 42) | CGATATTGTTCA TAATATGTCAG (SEQ ID NO: 43) | TCTGCGCTTC TCTTGGGAA (SEQ ID NO: 44) | GGCGTAAATC TTCCAGTTTA (SEQ ID NO: 45) |

-continued

Sequences of degenerate primers used for PCR recovery of error-free fragments

| Fragment (Daughter fragment) | CODE | Restric-tion enzyme used | Primer sequence Forward direction (5'→3') | Primer sequence Reverse direction (5'→3') | Nested PCR Primer sequence Forward direction (5'→3') | Nested PCR Primer sequence Reverse direction (5'→3') |
|---|---|---|---|---|---|---|
| 4-d | G2JQR9I0 6GS219 | Nest PCR from EarI pool | GTGGTATGC ACGTTGGTC (SEQ ID NO: 46) | TATGTGAGTGAT CNCCGTTTCAG (SEQ ID NO: 47) | TGGTGCAGTA GAAGACCGTA (SEQ ID NO: 48) | TTTTTCGAAC AGAAGCGGTA (SEQ ID NO: 49) |
| 4-e | G2JQR9I0 6HA06O | Nest PCR from BtsI pool | ATTACTTAGGG TATTGCGTTC (SEQ ID NO: 50) | AGACCTTCAG TCTTTGCGAT (SEQ ID NO: 53) | CGTTTACCTGA TCAAACACAGC (SEQ ID NO: 52) | AGCTGCACT TTATAGCGG (SEQ ID NO: 53) |
| 4-f | G2JQR9I0 7IGZCH | Nest PCR from EarI pool | ATAGCGTTATTA ATTTCTGTCAG (SEQ ID NO: 54) | ATAGTTATTC GGCTAGTCCT (SEQ ID NO: 55) | TGCTCTGTTA AACGAACGCA (SEQ ID NO: 56) | TTGCGACCAGA AATAGTGGTG (SEQ ID NO: 57) |
| 5-a | G2JQR9I0 7ILSL3 | EcoP15I from BtsI pool | TCATAGAGGA GGTGCTATGG (SEQ ID NO: 58) | CGGATCGTTT ATTGACTGTT (SEQ ID NO: 59) | | |
| 5-b | G2JQR9I0 7IMJ1B | EcoP15I from EarI pool | GATATTTCGC GGTTCTGTTG (SEQ ID NO: 60) | AGGTAAAGGTTA CTTAAACTCAG (SEQ ID NO: 61) | | |
| 5-c | G2JQR9I0 6GZ26W | EcoP15I from BtsI pool | TAGTCTTTGC CGGTTTATTA (SEQ ID NO: 62) | TTGCAAAGA TTCTACAGA (SEQ ID NO: 63) | | |
| 5-d | G2JQR9I0 7IQTYC | EcoP15I from EarI pool | CTAAACTCTT TACTTCCTAT (SEQ ID NO: 64) | AGCTCGTTAT TATGTGGCTT (SEQ ID NO: 65) | | |
| 5-e | G2JQR9I0 7IBIHM | EcoP15I from EarI pool | TTATGAGAAA TGTTTCACTG (SEQ ID NO: 66) | TAGAACACTA TCAAATCTAG (SEQ ID NO: 67) | | |
| 5-f | G2JQR9I0 7IEGMC | EarI | TTTGTAATTTGA CTCTGATGCAG (SEQ ID NO: 68) | TAGGAATCTTTT GACTTTTCACAG (SEQ ID NO: 69) | | |
| 6-a | G2JQR9I0 7IQ369 | Nest PCR from EarI pool | TACTGGGAGCAA ACAATTCTCAG (SEQ ID NO: 70) | TTCGTCTGCTG TTTTCACTCAG (SEQ ID NO: 71) | CTAACTACGTTT TCGATCACTTCG (SEQ ID NO: 72) | TTCACGGATTT TGTCGAAGAC (SEQ ID NO: 73) |
| 6-b | G2JQR9I0 6HBBGB | Nest PCR from EarI pool | GTGGGATGG AAGCTCCTC (SEQ ID NO: 74) | TGTATTATGTCC TTTTTGCCAGC (SEQ ID NO: 75) | GCTTTCAGCGAG CCGGTCTTCGAC AAAATCCGTGA AACCTTCCACG GTTTGGTTATC (SEQ ID NO: 76) | CAGGTACAGCT CACCCAC (SEQ ID NO: 77) |
| 6-c | G2JQR9I0 7H1GGH | EcoP15I from EarI pool | TGTTGGATAT ATAGGGTTAC (SEQ ID NO: 78) | CATGGGGATG ATGTGTACTT (SEQ ID NO: 79) | | |
| 6-d | G2JQR9I0 7HZ198 | EcoP15I from EarI pool | AATTCACTCA GAATAATTTT (SEQ ID NO: 80) | ATTTAGTTGG AATTAATCTC (SEQ ID NO: 81) | | |
| 6-e | G2JQR9I0 7IMS4O | EarI | CTACTGTTCG TTCCCAATTA (SEQ ID NO: 82) | TTGGTGTAAA ACTGGGGGAA (SEQ ID NO: 83) | | |
| 7-a | G2JQR9I0 7H02JG | EcoP15I from EarI pool | ATGTGTTATA GAAGTTGTTG (SEQ ID NO: 84) | TGACATGTGT TATCCCTGCT (SEQ ID NO: 85) | | |
| 7-b | G2JQR9I0 6HGWSA | EarI | TTTCAGAAAC TTAAACTTAC (SEQ ID NO: 86) | TTATAAGAAG TAATAGGAAT (SEQ ID NO: 87) | | |
| 7-c | G2JQR9I0 7H8TE4 | EarI | TATACAATCT ATTGGTAATC (SEQ ID NO: 88) | TGGAATACTT TAATCCTTTC (SEQ ID NO: 89) | | |

-continued

Sequences of degenerate primers used for PCR recovery of error-free fragments

| Fragment (Daughter fragment) | CODE | Restriction enzyme used | Primer sequence Forward direction (5'→3') | Primer sequence Reverse direction (5'→3') | Nested PCR Primer sequence Forward direction (5'→3') | Nested PCR Primer sequence Reverse direction (5'→3') |
|---|---|---|---|---|---|---|
| 7-d | G2JQR9I07H7QRT | EcoP15I from Btsl pool | TTACATGCTT TCGACACATA (SEQ ID NO: 90) | TGTATAGTGT GAGGATCTTT (SEQ ID NO: 91) | | |
| 7-e | G2JQR9I07IEEEC | EcoP15I from Btsl pool | GTTAATTTCT GGGGATACGT (SEQ ID NO: 92) | TAACTCACGC TTTTTATAAG (SEQ ID NO: 93) | | |
| 7-f | G2JQR9I07IPGUX | Earl | TTCTTGTCACT CTCTTTATCCA (SEQ ID NO: 94) | TCTATCGGTT TTCGGGTTT (SEQ ID NO: 95) | | |
| 8-a | G2JQR9I06G6PRN | Nest PCR from Btsl pool | GAAGCACCTGTC TTATTTAACAG (SEQ ID NO: 96) | TGATCTTCC CGGGTAGGC (SEQ ID NO: 97) | GGTCGTTCTGC GTGTAGATAT (SEQ ID NO: 98) | CTGCAGCAGTT TCGTAACTTC (SEQ ID NO: 99) |
| 8-b | G2JQR9I07IRU8F | EcoP15I from Earl pool | TCATCCTATT ACGATGCCCG (SEQ ID NO: 100) | GCGTTGGAAG CTTTTTATTG (SEQ ID NO: 101) | | |
| 8-c | G2JQR9I07IJA46 | EcoP15I from Earl pool | ATTTATAAGG ACGGGCCAGC (SEQ ID NO: 102) | AAACGNTCCC CGTATTGGTA (SEQ ID NO: 103) | | |
| 8-d | G2JQR9I07IBAZE | EcoP15I from Btsl pool | TAATCTGATC GATGCTAGGA (SEQ ID NO: 104) | TTTTGATTCA ATCCTCCTAA (SEQ ID NO: 105) | | |
| 9-a | G2JQR9I07IQ5TF | Earl | TTTCCTATTTC TTCATTGGCAG (SEQ ID NO: 106) | TTGCGATGGT TTACTTTGAT (SEQ ID NO: 107) | | |
| 9-b | G2JQR9I07IK8X6 | Earl | ATCATTGCAC TTGTTGTTCG (SEQ ID NO: 108) | GGAAGGTTTT TTACTGATTT (SEQ ID NO: 109) | | |
| 9-c | G2JQR9I06HGDLG | Earl | TTATTCGTGG ATTGGTGTTC (SEQ ID NO: 110) | ATTTTTCTAG GTTCTGATTA (SEQ ID NO: 111) | | |
| 9-d | G2JQR9I06G8AYI | EcoP15I from Earl pool | TGATTTCACC ACTAAGTCT (SEQ ID NO: 112) | CCTCCTTTAT TTCTCGTGC (SEQ ID NO: 113) | | |
| 9-e | G2JQR9I07ITPM8 | Earl | TAAAGTTATC ATGTGCTACC (SEQ ID NO: 114) | TGTAAACCTA TATTCATCTC (SEQ ID NO: 115) | | |
| 9-f | G2JQR9I06HH6RD | Nest PCR from Earl pool | GTTCATTGCATA ATGCTTCTCAG (SEQ ID NO: 116) | TTAAAGCCCTTT ACATCCAGCAGC (SEQ ID NO: 117) | CTAACCCGTTC TGCAAGGAAG (SEQ ID NO: 118) | CGGCTGCTGC TGGCGG (SEQ ID NO: 119) |
| 9-g | G2JQR9I07IAIBJ | EcoP15I from Earl pool | ATTGATATGT AAGAGATTTC (SEQ ID NO: 120) | AATAGGTACC ATTTTCGTT (SEQ ID NO: 121) | | |
| 10-a | G2JQR9I06G19MG | Nest PCR from Earl pool | GATTACTACATT TTTCTCAACAG (SEQ ID NO: 122) | CTTTTGGGGG GGGTTGGGCC (SEQ ID NO: 123) | CGTTTATGG GAAAGCGC (SEQ ID NO: 124) | GCTATCCTTCA TGAAAACGTG (SEQ ID NO: 125) |
| 10-b | G2JQR9I07IHPYZ | Earl | AATTGGTTAC CTCTATCCCC (SEQ ID NO: 126) | CTCATACTGG GATCCGATTT (SEQ ID NO: 127) | | |
| 10-c | G2JQR9I07H9H15 | EcoP15I from Earl pool | GCATAAAGCG GGAGGCTTCT (SEQ ID NO: 128) | CTGTGTCATA GAATAGTGC (SEQ ID NO: 129) | | |
| 10-d | G2JQR9I07IS7M7 | EcoP15I from Btsl pool | TTTCGACCGA TTTCAGTCTG (SEQ ID NO: 130) | TTTTTTGAC GGTAATTA (SEQ ID NO: 131) | | |

-continued

Sequences of degenerate primers used for PCR recovery of error-free fragments

| Fragment (Daughter fragment) | CODE | Restriction enzyme used | Primer sequence Forward direction (5'→3') | Primer sequence Reverse direction (5'→3') | Nested PCR Primer sequence Forward direction (5'→3') | Nested PCR Primer sequence Reverse direction (5'→3') |
|---|---|---|---|---|---|---|
| 10-e | G2JQR9I0 7H9WDO | EarI | CTTCCTGTG GGTTTTCTA (SEQ ID NO: 132) | TTTTACATCA TTCGCGTATT (SEQ ID NO: 133) | | |
| 10-f | G2JQR9I0 7IA5L7 | EcoP15I from EarI pool | TTTTTGAGCT ACGCTTTCGG (SEQ ID NO: 134) | TCAATACAT TCTACTTT (SEQ ID NO: 135) | | |
| 11-a | G2JQR9I0 7IN2PX | EcoP15I from EarI pool | GTCAGTAGTA TACCGTTCGT (SEQ ID NO: 136) | CGATCTAAGA TTGCCTTCCT (SEQ ID NO: 137) | | |
| 11-b | G2JQR9I0 71E917 | EarI | TCTCATAATTGG GAATTGTACAG (SEQ ID NO: 138) | TTTATGTTTTTG AATTAGCAGCA (SEQ ID NO: 139) | | |
| 11-c | G2JQR9I0 71QTJR | EarI | ATCTTTTATG TACTTTGTGA (SEQ ID NO: 140) | TTTTTCAACA CTTTTAGTGT (SEQ ID NO: 141) | | |
| 11-d | G2JQR9I0 7IM5CB | EarI | TAATTTCCT GTGCAACT (SEQ ID NO: 142) | TCTTGTTTAT TTCTTTGGGT (SEQ ID NO: 143) | | |
| 11-e | G2JQR9I0 6G547R | Nest PCR from BtsI pool | ATGTATCCTCGC TCTTTAACCAG (SEQ ID NO: 144) | CACCCGGTTTG ATTATTACTCA (SEQ ID NO: 145) | GGCATTCTGG CGATGGAGAT (SEQ ID NO: 146) | GTCGTAGTACT CATACAGGCG (SEQ ID NO: 147) |
| 11-f | G2JQR9I0 7HZAYS | Nest PCR from BtsI pool | CTAACGCATTG TCAGGTTTCC (SEQ ID NO: 148) | ACTCCGGATAC CAGTGTAGAAC (SEQ ID NO: 149) | GAATCAGAAAA CCAGCGTCGCC TGTATGAGTAC TACGACGCGTT AGATTCCAC (SEQ ID NO: 150) | TTACTTCCAAC GACCGATGTAC TGAGCCGCC (SEQ ID NO: 151) |

TABLE 2

Sequences of daughter fragments obtained after PCR recovery

| Fragment (Daughter fragment) | Sequence(5'→3') | Expected length (bp) |
|---|---|---|
| 1-a | CTATTTGATGTTCGTAGTTCCAGCAGCACCGACTAATGCAGGCTGGCAGTAATGACCCAATTGAAGCCGC CTAACGGGACCACTCCGATCGGCTTCAGCGCCACTACTAGCCTGAACGCTAGCGGCTCTTCCTCGGTTAA GAATGGTACCATCAAGCCTTCGAATGGTATCTTCAAACCTTCTACTCGTGACACCATGGACCCGTGCTCG GGCAACGCCGCTGACGGCTCCATTCGCGTACGTTTTCGCGGTGGCATCGAACGTTGGAAAGAGTGTGTAA ACCAAGTGCCGGAGCGTTGCGACCTGTCTGGTCTGACCACGGACAGCACCCGCTACCAGCTGGCTTCCGA ACACATGACCCTGCGACCTGCTGAGCCTTTTCAAAGCGAAAG (SEQ ID NO: 152) | 392 |
| 1-b | ATCTATTAGGTCATAGTAGGCAGCAGAGGGCATCTTAGCGGTCGCTCTTCTGGCTTCGGCGACGCGAGCG CGGCTTACCAGGAACGTCTGATGACTGTGCCGGTAGATGTTCATGCTGCGCTCCAGGAGCTGTGCCTGGA ACGCCGCGTCTCTGTGGGTTCTGTGATCAACTTCAGCGTTCACCAGATGCTGAAGGGTTTTGGCAACGGT ACTCACACTATCACCGCGAGCCTGCACCGCGAACAGAATCTGCAGAACTCCTCTCCGTCTTGGGTCGTTT CCCCTACTATCGTGACCCATGAAAACCGCGATGGCTGGTCAGTGGCGCAGGCAGTGGAGTCTATCGAGGC TAGAAGACCACACATGGCACCTTTGCTGCTGCATGCAGAGGAAACCATAAAT (SEQ ID NO: 153) | 402 |
| 1-c | TGCTATTCTTTCTGCCTTTTCAGCAGCAAAGGTGCCATGTGTGGCTCTTCTGGCAACGGTACTCACACTA TCACCGCGAGCCTGCACCGCGAACAGAATCTGCAGAACTCCTCTCCGTCTTGGGTCGTTTCCCCTACTAT CGTGACCCATGAAAACCGCGATGGCTGGTCAGTGGCGCAGGCAGTGGAGTCTATCGAGGCTGGTCGTGGC TCCGAAAAGGAATCTGTGACCGCGATTGATTCCGGCTCCTCCCTGGTCAAAATGGGTCTGTTCGATCTGC TGGTTTCCTTCGTCGATGCGGATGACGCGCGTATCCCTTGCTTCGACTTTCCGCTGGCTGTTATTGTGCG CAGAAGAGCGACCGCTAAGATGCCCTCTGCTGTGGAAACGCAACAAACATTC (SEQ ID NO: 159) | 402 |
| 1-d | TCGAGCTCAATAGTTTTTTCAGCAGCACCGACTAATGCAGGCTGGCGTGATGACGCGCGTATCCCTTGCT TCGACTTTCCGCTGGCTGTTATTGTGCGCGAGTGCGATGCAAACCTGTCTCTCACCCTTCGCTTCTCGGA CTGCCTGTTCAACGAGGAAACCATTTGTAATTTCACGGATGCCCTCAATATCCTGTTGGCTGAGGCAGTT ATCGGTCGTGTAACTCCGGTAGCCGATATCGAGCTGCTGTCTGCAGAGCAGAAACAACAGCTGGAGGAAT | 400 |

TABLE 2-continued

Sequences of daughter fragments obtained after PCR recovery

| Fragment (Daughter fragment) | Sequence(5'→3') | Expected length (bp) |
|---|---|---|
| | GGAACAACACCGATGGTGAATATCCGTCTAGCAAGCGTCTGCACCACCTGATTGAAGAGGTGGTGGAACC ACTGCGAACACATGACCCTGCGACCTGCTGCTGCTGAATGCAATCATAAA (SEQ ID NO: 155) | |
| 1-e | TTACTCCATTTTGCACTCTCAGCAGCACCGACTAATGCAGGCTGGCATGATGACGCGCGTATCCCTTGCT TCGACTTTCCGCTGGCTGTTATTGTGCGCGAGTGCGATGCAAACCTGTCTCTCACCCTTCGCTTCTCTTC AACGAGGAAACCATTTGTAATTTCACGGATGCCCTCAATATCCTGTTGGCTGAGGCAGTTATCGGTCGTG TAACTCCGGTAGCCGATATCGAGCTGCTGTCTGCAGAGCAGAAACAACAGCTGGAGGAATGGAACAACAC CGATGGTGAATATCCGTCTAGCAAGCGTCTGCACCACCTGATTGAAGAGGTGGTGGAACCACTACGAACA CATGACCCTGCGACCTGCTGTCAACAAAGGCCAAAGAAT (SEQ ID NO: 156) | 389 |
| 2-a | TTAGTTTCAACATGTATATACAGCAGCACCGACTAATGCAGGCTGGAGTGCAACGAGGAAACCATTTGTA ATTTCACGGATGCCCTCAATATCCTGTTGGCTGAGGCAGTTATCGGTCGTGTAACTCCGGTAGCCGATAT CGAGCTGCTGTCTGCAGAGCAGAAACAACAGCTGGAGGAATGGAACAACACCGATGGTGAATATCCGTCT AGCAAGCGTCTGCACCACCTGATTGAAGAGGTGGTGGAACGTCACGAAGACAAAATCGCTGTGGTGTGCG ACGAACGTGAACTGACTTACGGTGAACTCAATGCCCACGGCAACTCCCTGGCGCGTTACCTGCACAGCAT CACTGCGAACACATGACCCTGCGACCTGCTGAAAGTGTCGAATATACACAT (SEQ ID NO: 157) | 401 |
| 2-b | CTATTTTCAGTGTGCCTTTCAGCAGCACCGACTAATGCAGGCTGGAGTGGTCACGAAGACAAAATCGCTG TGGTGTGCGACGAACGTGAACTGACTTACGGTGAACTCAATGCCCAGGGCAACTCCCTGGCGCGTTACCT GCGCAGCATTGGTATTCTGCCTGAACAGCTGGTTGCGCTGTTTCTGGACAAATCCGAAAAATTGATCGTA ACCATCCTGGGCGTCTGGAAATCCGGTGCTGCTTACGTGCCAATTGACCCGACCTACCCTGACGAACGTG TTCGTTTCGTTCTGGACGACACGAAAGCCCGTGCGATTATCGCTTCCAATCAGCATGTTGAACGCCTCCC ACTGCGAACACATGACCCTGCGACCTGCTGAAAGTTTCATCAACTTAGGA (SEQ ID NO: 158) | 400 |
| 2-c | TATCTGGTAGGAGGGGTTCAGCAG- CAAAGGTGCCATGTGTGGCTCTTCTAATTGATCGTAACCATCCTGG GCGTCTGGAAATCCGGTGCTGCTTACGTGCCAATTGACCCGACCTACCCTGACGAACGTGTTCGTTTCGT TCTGGACGACACGAAAGCCCGTGCGATTATCGCTTCCAATCAGCATGTTGAACGCCTCCAGCGTGAAGTA ATCGGTGATCGCAACCTGTGCATCATCCGTCTCGAACCACTGCTGGCGAGCCTTGCGCAGGATTCTTCTA AATTCCCTGCCCACAACCTGGAT- GATTTGCCGCTGACCAGCCAGCAGCTGGCGTACGTTACTTATACCAAG AAGAGTGACCGCTAAGATGCCCTCTGCTGCAGCGTCATTGCCAGTTCTA(SEQ ID NO: 159) | 400 |
| 2-d | TTCTGTTTGTCTTAAATGCGCAGCAGAGGGCATCTTAGCGGTCGCTCTTCTAGCGTGAAGTAATCGGTGA TCGCAACCTGTGCATCATCCGTCTCGAACCACTGCTGGCGAGCCTTGCGCAGGATTCTTCTAAATTCCCT GCCCACAACCTGGATGATTTGCCGCTGACCAGCCAGCAGCTGGCGTACGTTACTTATACCAGCGGTACCA CCGGCTTTCCGAAAGGCATTTTCAAACAGCACACTAACGTTGTTAACTCCATCACAGACCTGTCCGCTCG TTACGGTGTTGCAGGTCAACACCATGAAGCTATCCTGCTCTTCAGTGCTTGCGTTTTCGAACCGTTCGTT CAGAAGAGCCACACATGGCACCTTTGCTGCTGACGCAATCTTAAAAACGGTA (SEQ ID NO: 160) | 402 |
| 2-e | CTGAAATTCATTTATGTTTGCAGCAGCACCGACTAATGCAGGCTGGCAGTGGTTAACTCCATCACAGACC TGTCCGCTCGTTACGGTGTTGCAGGTCAACACCATGAAGCTATCCTGCTCTTCAGTGCTTGCGTTTTCGA ACCGTTCGTTCGTCAGACTCTGATGGCCCTGGTGAACGGTCACCTGCTCGCCGTGATTAACGATGTAGAA AAATATGACGCTGACACCCTCCTCCCATTTATCCGCCGTCACTCTATCACCTATCTGAACGGTACTGCGT CGGTTCTCCAAGAGTATGACTTCTCTGACTGTCCGAGCCTGAACCGTATCATCCTCTGCGAACACATCGA CCCTGCGACCTGCTGCAAAAAGGTACCCCATAG (SEQ ID NO: 161) | 383 |
| 2-f | ATATTCGAGCGTATGTATTACAGCAGCACCGACTAATGCAGGCTGGCGTCTCTATCACCTATCTGAACGG TACTGCGTCGGTTCTCCAAGAGTATGACTTCTCTGACTGTCCGAGCCTGAACCGTATCATCCTGGTGGGC GAGAACCTGACCGAAGCACGTTACCTGGCACTGCGTCAGCGTTTCAAAAATCGTATTCTGAACGAGTACG GTTTCACCGAGTCTGCGTTCGTGACTGCGCTGAAAATTTTCGATCCGGAAAGCACCCGCAAAGATACCTC CCTGGGGCGTCCGGTGCGCAATGTTAAATGCTATATCTTGAACCCTAGCCTGAAACGCGTGCCAATTGGC ATGCGAACACATGACCCTGCGACCTGCTGGAGACTGTAAACAATCACTT (SEQ ID NO: 162) | 399 |
| 2-g | TCATTTCGAGAAAAGGCCGACAGCAGGTCGCAGGGTCATGTGTTCGCAGTGGAACGAGTACGGTTTCACC GAGTCTGCGTTCGTGACTGCGCTGAAAATTTTCGATCCGGAAAGCACCCGCAAAGATACCTCCCTGGGGC GTCCGGTGCGCAATGTTAAATGCTATATCTTGAACCCTAGCCTGAAACGCGTGCCAATTGGTGCTACAGG TGAGCTGCATATTGGCGGCCTGGGTATCTCCAAGGGTTACTTGAATCGTCCGGAACTGACGCCGCACCGC TTCATCCCGAACCCGTTTCAGACCGATTGCGAAAAACAGCTGGGTATCAACTCTCTGATGTACAAAACCG GCACTGTCAGCCTGCATTAGTCGGTGCTGCTGCAAAATAAGGGAAAGAACCC(SEQ ID NO: 163) | 402 |
| 3-a | AACGAGGATATACAAATATACAGCAGCAAAGGTGCCATGTGTGGCTCTTCTTGAATCGTCCGGAACTGAC GCCGCACCGCTTCATCCCGAACCCGTTTCAGACCGATTGCGAAAAACAGCTGGGTATCAACTCTCTGATG TACAAAACCGGTGATCTGGCTCGCTGGCTCCCGAACGGTGAAGTTGAATACCTGGGCCGTGCGGATTTCC AGATCAAACTGCGCGGTATTCGTATTGAGCCGGGCGAAATCGAGACTATGCTGGCGATGTATCCGCGCGT TCGTACCTCCCTGGTGGTTTCCAAGAAATTACGTAACGGTCCTGAAGAAACAACGAACGAACACCTGGTA GAGAAGAGCGACCGCTAAGATGCCCTCTGCTGATATACCACTCTCAACACTT(SEQ ID NO: 169) | 402 |
| 3-b | ATGGAGCTTTTATGTGGTTACAGCAGAGGACATCTTAGCGGTCGCTCTTCTCGGATTTCCAGATCAAACT GCGCGGTATTCGTATTGAGCCGGGCGAAATCGAGACTATGCTGGCGATGTATCCGCGCGTTCGTACCTCC CTGGTGGTTTCCAAGAAATTACGTAACGGTCCTGAAGAAACAACGAACGAACACCTGGTAGGCTACTACG TATGCGACTCCGCATCTGTTTCCGAAGCGGATCTGCTGTCCTTCCTGGAGAAGAAGCTGCCGCGTTATAT GATTCCGACTCGTCTGGTACAGCTGAGCCAGATCCCGGTTAACGTCAACGGTAAAGCCGATCTGCGTGCT CAGAAGAGCCACACATGGCACCTTTGCTGCTGAACAACGAAACTAGACAATT (SEQ ID NO: 165) | 402 |

TABLE 2-continued

Sequences of daughter fragments obtained after PCR recovery

| Fragment (Daughter fragment) | Sequence(5'→3') | Expected length (bp) |
|---|---|---|
| 3-c | TGATTATGGTGGTTGCGGTGCAGCAGCACCGACTAATGCAGGCTGGCAGTGTTCCTGGAGAAGAAGCTGC<br>CGCGTTATATGATTCCGACTCGTCTGGTACAGCTGAGCCAGATCCCGGTTAACGTCAACGGTAAAGCCGA<br>TCTGCGTGCTCTGCCGGCGGTTGATATCTCCAACAGCACCGAAGTTCGTTCTGATCTGCGTGGTGATACC<br>GAAATTGCCCTCGGCGAAATCTGGGCGGACGTGCTGGGCGCGCGTCAGCGTTCGGTTAGCCGTAACGATA<br>ACTTTTTCCGCCTCGGTGGCCACTCTATCACCTGCATCCAGCTGATTGCGCGTATCCGTCAGCGTCAGCG<br>TCACTGCGAACACATGACCCTGCGACCTGCTGCAGAATAACTAAATTAGTAT(SEQ ID NO: 166) | 402 |
| 4-a | TATTTTTTTCCAATTTTTTACAGCAGCACCGACTAATGCAGGCTGGCAACCTGCATCCAGCTGATTGCGC<br>GTATCCGTCAGCGTCAGCGTTTGTCTGTGTCTATCTCTGTGGAAGACGTGTTTGCTACACGCACTCTTGA<br>GCGTATGGCCGACCTGTTGCAAAACAAACAGCAAGAGAAATGCGACAAACCACACGAAGCACCGACTGAA<br>CTGCTTGAAGAAAACGCTGCGACTGATAACATCTACCTGGCGAACAGCCTGCAGCAAGGTTTCGTCTACC<br>ATTACCTGAAAAGCATGGAACAAAGTGATGCTTATGTAATGCAGAGCGTTCTGCGTTACAACACCACCCT<br>TTCCCGGATCTGTTCCAGCGTGCCTGGAAACACGCGCAGCCTGCGAACACATGACCCTGCGACCTGCTGG<br>CAACAGAATAGCAGAGGAT (SEQ ID NO: 167) | 399 |
| 4-b | CTAATTTGAATGCAGTCCGTCAGCAGCACCGACTAATGCAGGCTGGCAGTAAGCATGGAACAAAGTGATG<br>CTTATGTAATGCAGAGCGTTCTGCGTTACAACACCACCCTTTCCCCGGATCTGTTCCAGCGTGCCTGGAA<br>ACACGCGCAGCAAAGCTTCCCGGCTCTGCGTCTGCGCTTCTCTTGGGAAAAAGAAGTCTTCCAGCTGCTG<br>GGATCAGGACCCGCCTCTGGACTGGCGTTTCCTCTACTTCACTGATGTGGTGGCAGGTGCAGATCCCCGT<br>TNTCAGTCGGGCGAACCAGTGACAGCTGGGTATCTTCGTTGATGCCTCAGCGCTCAGTTCGGACAGCTGA<br>CGCAGAAGGTACACTGCGAACACATGACCCTTCGACCTGCTTGGTTTTTTCCAAAGGTAATGT (SEQ<br>ID NO: 168) | 413 |
| 4-c | TTAAGTATGATTAATGCTGTCAGCAGCACCGACTAATGCAGGCTGGCGTGCAAAGCTTCCCGGCTCTGCG<br>TCTGCGCTTCTCTTGGGAAAAAGAAGTCTTCCAGCTGCTGGATCAGGACCCGCCTCTGGACTGGCGTTTC<br>CTCTACTTCACTGATGTGGCGGCTGGTGCAGTAGAAGACCGTAAACTGGAAGATTTACGCCACCAGGACC<br>TCACCGAGCGTTTTAAACTGGATGTGGGCCGTCTGTTTCGCGTTTACCTGATCAAACACAGCGAAAACCG<br>TTTCACTTGTCTGTTCTCTTGTCACCCGCTATCCTGGACGGCTGGTCCTTACCGCTTCTGTTCGAAAACC<br>CTGCGAACACATGACCCTGCGACCTGCTGACATATTATGAACAATATCG (SEQ ID NO: 169) | 399 |
| 4-d | GTGGTATGCACGTTGGTCCTCAGCAGCACCGACTAATGCAGGCTGGCAGTCCAAAGCTTCCCGGCTCTGC<br>GTCTGCGCTTCTCTTGGGAAAAAGAAGTCTTCCAGCTGCTGGATCAGGACCCGCCTCTGGACTGGCGTTT<br>CCTCTACTTCACTGATGTGGCGCTGGTGCAGTAGAAGACCGTAAACTGGAAGATTTACGCCGCCAGGACC<br>TCACCGAGCGTTTTAAACTGGATGTGGGCCGTCTGTTTCGCGTTTACCTGATCAAACACAGCGAAAACCG<br>TTTCACTTGTCTGTTCTCTTGTCACCACGCTATCCTGGACGGCTGGTCCTTACCGCTTCTGTTCGAAAAA<br>CNCTGCGAACACATGACCCTGCGACCTGCTGAAACGGEGATCACTCACATA (SEQ ID NO: 170) | 401 |
| 4-e | ATTACTTAGGGTATTGCGTTCAGCAGCACCGACTAATGCAGGCTGGCAGGCGTTTACCTGATCAAACACA<br>GCGAAAACCGTTTCACTTGTCTGTTCTCTTGTCACCACGCTATCCTGGACGGCTGGTCCTTACCGCTTCT<br>GTTCGAAAAAGTACACGAAACATACCTGCAACTGCTGCACGGCGATAACCTGACCTCCTCTATGGATGAT<br>CCATACACCCGTACCCAACGCTACCTGCATGCGCACCGCGAAGATCACCTCGACTTTTGGGCTGGCGTGG<br>TGCAGAAAATCAACGAACGTTGCGATATGAATGCTCTGTTAAACGAACGCAGCCGCTATAAAGTGCAGCT<br>CACTGCGAACACATGACCCTGCGACCTGCTGATCGCAAAGACTGAAGGTCT (SEQ ID NO: 171) | 401 |
| 4-f | ATAGCGTTATTAATTTCTGTCAGCAGAGGGCATCTTAGGGGTCGCTCTTCTAAGATCACCTCGACTTTTG<br>GGCTGGCGTGGTGCAGAAAATCAACGAACGTTGCGATATGATGCTCTGTTAAACGAACGCAGCCGCTATA<br>AAGTGCAGCTGGCCGACTACGATCAGGTACAGGAACAGCGTCAGCTGACGATCGCTCTGAGCGGTGACGC<br>GTGGCTGGCGGATCTGCGCCAGACATGCAGTGCGCAGGGCATCACGCTGCACTCTATCCTGCAATTTGTA<br>TGGCATGCAGTTCTGCATGCCTACGGTGGCGGTACTCACACTATCACTGGCACCACTATTTCTGGTCGCA<br>AGAAGCGCCACACATGGCACCTTTGCTGCTGAGGACTAGCCGAATAACTAT (SEQ ID NO: 172) | 401 |
| 5-a | TCATAGAGGAGGTGCTATGGCAGCAGGTCGCAGGGTCATGTGTTCGCAGTGCTACGGTGGCGGTACTCAC<br>ACTATCACTGGCACCACTATTTCTGGTCGCAACCTCCCGATCCTGGGTATCGAGCGTGCGGTAGGCCCGT<br>ACATTAACACCCTGCCGTTAGTGTTGGACCATTCTACTTTTAAAGACAAGACGATCATGGAAGCTATTGA<br>AGACGTCCAAGCGAAGGTGAATGTTATGAACTCCCGTGGTAATGTAGAACTGGGTCGCCTGCACAAAACC<br>GACCTGAAACATGGCCTGTTCGATTCTCTGTTTGTGCTGGAAAACTATCCAAACCTGGATAAATCCAGCC<br>TGCATTAGTCGGTGCTGCTGAACAGTCAATAAACGATCCG (SEQ ID NO: 173) | 390 |
| 5-b | GATATTTCGCGGTTCTGTTGCAGCAGCACCGACTAATGCAGGCTGGCAGTAGCTATTGAAGACGTCCAAG<br>CGAAGGTGAATGTTATGAACTCCCGTGGTAATGTAGAACTGGGTCGCCTGCACAAAACCGACCTGAAACA<br>TGGCCTGTTCGATTCTCTGTTTGTGCTGGAAAACTATCCAAACCTGGATAAATCCCGTACTCTGGAGCAC<br>CAAACTGAACTGGGTTACTCCATCGAGGGTGGTACCGAAAAACTGAACTATCCGCTGGCGGTGATTGCTC<br>GTGAGGTTGAGACCACTGGCGGCTTTACTGTTAGCATCTGCTATGCGAGCGAACTGTTTGAAGAGGTGAT<br>CACTGCGAACACATGACCCTGCGACCTGCTGAGTTTAAGTAACCTTTACCT (SEQ ID NO: 174) | 401 |
| 5-c | TAGTCTTTGCCGGTTTATTACAGCAGCACCGACTAATGCAGGCTGGCAGTGAACTGAACTATCCGCTGGC<br>GGTGATTGCTCGTGAGGTTGAGACCACTGGCGGCTTTACTGTTAGCATCTGCTATGCGAGCGAACTGTTT<br>GAAGAGGTGATGATCAGCGAGCTTCTCCATATGGTACAGGATACCCTGATGCAGGTTGCACGCGGGCTCA<br>ACGAACCTGTGGGCTCCCTGGAATACCTGTCTTCCATCCAGTTAGAGCAGCTGGCAGCGTGGAACGCCAC<br>CGAAGCGGAGTTCCCGGACACGACCCTGCATGAAATGTTCGAGAACGAAGCATCTCAAAAGCCGGATAAA<br>ACACTGCGAACACATGACCCTGCGACCTGCTGTCTGTAGAATCTTTGCAA (SEQ ID NO: 175) | 400 |

TABLE 2-continued

Sequences of daughter fragments obtained after PCR recovery

| Fragment (Daughter fragment) | Sequence(5'→3') | Expected length (bp) |
|---|---|---|
| 5-d | CTAAACTCTTTACTTCCTATCAGCAGAGGGAATCTTAGCGGTCGCTCTTCTTTAGAGCAGCTGGCAGCGTGGAACGCCACCGAAGCGGAGTTCCCGGACACGACCCTGCATGAAATGTTCGAGAACGAAGCATCTCAAAAGCCGGATAAAATTGCAGTCGTGTACGAAGAAACCTCTCTGACCTATCGCGAGCTGAACGAACGTGCCAATCGCATGGCGCACCAGCTGCGTTCCGACGTTTCTCCGAACCCGAACGAAGTGATCGCGCTGGTTATGGACAAGAGTGAACACATGATCGTAAATATCTTGGCTGTGTGGAAATCTGGTGGCGCATACGTGCCGATCGATCCGAGAAGATCCACACATGGCACCTTTGCTGCTGAAGCCACATAATAACGAGCT (SEQ ID NO: 176) | 402 |
| 5-e | TTATGAGAAATGTTTCACTGCAGCAGAGGGCATCTTAGCGGTCGCGGACAAGAGTGAACACATGATCGTAAATATCTTGGCTGTGTGGAAATCTGGTGGCGCATACGTGCCGATCGATCCGGGCTACCCGAATGACCGTATTCAGTATATCCTCGAGGACACTCAGGCGTTGGCTGTTATCGCAGATTCTTGTTACCTGCCTCGTATCAAAGGTATGGCCGCGTCTGGTACGCTGCTCTACCCGTCTGTCCTGCCGGCAAACCCAGACAGCAAATGGTCTGTGTCAAACCCGTCGCCGCTGTCTCGTAGCACCGACCTGGCAGAAGAGCCACACATGGCACCTTTGCTGCTGCTAGATTTGATAGTGTTCTA (SEQ ID NO: 177) | 372 |
| 5-f | TTTGTAATTTGACTCTGATGCAGCAGAGGGCATCTTAGCGGTCGCTCTTCTCGTCTGGTACGCTGCTCTACCCGTCTGTCCTGCCGGCAAACCCAGACAGCAAATGGTCTGTGTCAAACCCGTCGCCGCTGTCTCGTAGCACCGACCTGGCATACATCATCTACACCTCTGGCACCACCGGCCGCCCGAAAGGCGTGACTGTGGAGCATCACGGTGTGGTGAACCTGCAGGTATCCCTGAGCAAAGTTTTTGGTCTGCGTGACACCGACGACGAAGTCATCCTGTCTTTTTCTAACTACGTTTTCGATCACTTCGTAGAACAGATGACTGATGCTATCCTGAACGGGCAGAAGAAGAGCCACACAAGGCACCTTTGCTGCTGTGAAAAGTCAAAAGATTCCTA (SEQ ID NO: 178) | 403 |
| 6-a | TACTGGGAGCAAACAATTCTCAGCAGCACCGACTAATGCAGGCTGGCAGTAGGTCTGCGTGACACCGACGACGAAGTCATCCTGTCTTTTTCTAACTACGTTTTCGATCACTTCGTAGAACAGATGACTGATGCTATCCTGAACGGGCAGACGCTGCTGGTTCTGAACGATGGTATGCGTGGTGACAAAGAACGCCTGTACCGCTACATCGAAAAGAACCGTGTAACTTATCTGTCTGGTACTCCATCTGTGGTGTCTATGTATGAGTTCAGCCGTTTCAAAGACCACCTGCGCCGCGTCGATTGCGTCGGTGAAGCTTTCAGCGAGCCGGTCTTCGACAAAATCCGTGAACACTACGAACACATGACCCAGCGACCTGCTGAGTGAAAACAGCAGACGAA (SEQ ID NO: 179) | 400 |
| 6-b | GTGGGATGGAAGCTCCTCGACAGCAGAGGGCATCTTAGCGGTCGCTCTCTACCTTCCACGGTTTGGTTATCAATGGTTATGGCCCAACTGAAGTTAGCATCACTACCCATAAGCGTTTATACCCTTTCCCAGAGCGCCGCATGGATAAGTCGATCGGCCAGCAGGTCCACAACTCTACTAGCTACGTACTGAATGAAGATATGAAGCGTACCCCGATCGGTGCTGTGGGTGAGCTGTACCTGGGCGGTGAAGGTGTTGTCCGCGGTTATCATAATCGTGCGGTGTTACCGCCGAGCGCTTCATCCCGAACCCGTTCCAGTCTGAGGAAGATAAACGTGAAGGCCGTAACAGAAGAACCACACATGGCACCTTTGCTGCTGGCAAAAAGGACATAATACA (SEQ ID NO: 180) | 399 |
| 6-c | TTGTTGGATATATAGGGTTACAAAAGAGGGCATCTTAGCGGTCGCTCTTCTCGATCGGCCAGCAGGTCCACAACTCTACTAGCTACGTACTGAATGAAGATATGAAGCGTACCCCGATCGGTGCTGTGGGTGAGCTGTACCTGGGCGGTGAAGGTGTTGTCCGCGGTTATCATAATCGTGCGGATGTTACCGCCGAGCGCTTCATCCCGAACCCGTTCCAGTCTGAGGAAGATAAACGTGAAGGCCGTAACAGTCGCCTGTACAAGACGGGTGATCTGGTTCGCTGGATCCCGGGTAGCTCCGGCGAAGTCGAATACCTGGGTCGCAATGACTTCCAGGTTAAGATTCGCGAGAAGAACCACACATGGCACCTTTGCTGCTGAAGTACACATCATCCCCATG (SEQ ID NO: 181) | 402 |
| 6-d | AATTCACTCAGAATAATTTTCAGCAGCAAAGGTGCCTTGTGTGGCTCTCTCGGCGAAGTCGAATACCTGGGTCGCAATGACTTCCAGGTTAAGATTCGCGGCCTCCGTATCGAGCTGGGTGAAATCGAAGCGATCCTGAGCAGCTACCACGGCATTAAACAGAGCGTAGTGATCGCAAAAGACTGCCGTGAGGGGGCACAGAAATTCCTGGTCGGCTATTACGTTGCAGACGCTGCCCTGCCGTCCGCAGCGATCCGTCGTTTCATGCAGTCGCGCCTCCCGGGTTACATGGTTCCGTCCCGTCTGATCCTGGTTTCTAAATTCCCTGTTACTCCGTCCGGGAAGCTGGAAGAAGAGCGACCGCTAAGATGCCCTCTGCTGGAGATTAATTCCAACTAAAT (SEQ ID NO: 182) | 401 |
| 6-e | CTACTGTTCGTTCCCAATTACAGCAGAGGGCATCTTAGCGGTCGCTCTTCTCGTCTGATCCTGGTTTCTAAATTCCCTGTTACTCCGTCCGGGAAGCTGGACACCAAAGCACTGCCGCCGGCGGAGGAAGAAAGCGAAATCGACGTTGTTCCACCGCGCTCCGAAATTGAGCGTTCTCTCTGCGACATCTGGGCTGAACTGCTGGAAATGCACCCGGAAGAAATCGGCATTTACTCTGACTTCTTCTCCTTGGGCGGCGACAGCCTGAAATCTACTAAGTTATCCTTCATGATCCATGAGTCCTTTAACCGTGCTGTGAGCGTTAGCGCGTTATTCTGCCATCGCACAGTTAGAAGAGCCACACATGGCACCTTTGCTGCTGTTCCCCCAGTTTTACACCAA (SEQ ID NO: 183) | 402 |
| 7-a | ATGTGTTATAGAAGTTGTTGCAGCAGAGGGCATCTTAGCGGTCCTAAGTTATCCTTCATGATCCATGAGTCCTTTAACCGTGCTGTGAGCGTTAGCGCGTTATTCTGCCATCGCACAGTTGAAGCTCAAACTCACCTGATCTTGAACGACGCAGCAGATGTACACGAAATTACCCCGATCGATTGCAACGACACCCAGATGATCCCGGTTTCCCGTGCACAGGAACGTCTGCTGTTCATTCATGAATTCGAAAACGGTTCTAACGCTTACAACATTGACGCGGCTTTCGAACTGCCAGGTTCTGTGGACGCGAGCCTGCTAGAAGAGCCACACATGGCACCTGTGCTGCTGAGCAGGGATAACACATGTCA (SEQ ID NO: 184) | 371 |
| 7-b | TTTCAGAAACTTAAACTTACCAGCAGAGGGCATCTTAGCGGTCGCTCTTCTGAAGCTCAAACTCACCTGATCTTGAACGACGCAGCAGATGTACACGAAATTACCCCGATCGATTGCAACGACACCCAGATGATCCCGGTTTCCCGTGCACAGGAACGTCTGCTGTTCATTCATGAATTCGAAAACGGTTCTAACGCTTACAACATTGACGCGGCTTTCGAACTGCCAGGTTCTGTGGACGCGAGCCTGCTGGAACAGGCCCTTCGTGGCAACCTGGCACGTCACGAAGCACTGCGCACCCTGCTGGTTAAAGATCACGCCACTGGTATTTACCTGCAGAAAGTACTGAATAGAAGAGCCACACATGGCACCTTTGCTGCTGATTCCTATTACTTCTTATAA (SEQ ID NO: 185) | 402 |
| 7-c | TATACAATCTATTGGTAATCCAGCAGAGGGCATCTTAGCGGTCGCTCTTCTAGGAACGTCTGCTGTTCATTCATGAATTCGAAAACGGTTCTAACGCTTACAACATTGACGCGGCTTTCGAACTGCCAGGTTCTGTGGACGCGAGCCTGCTGGAACAGGCCCTTCGTGGCAACCTGGCACGTCACGAAGCACTGCGCACCCTGCTGGTTA | 402 |

TABLE 2-continued

| Sequences of daughter fragments obtained after PCR recovery | | |
|---|---|---|
| Fragment (Daughter fragment) | Sequence(5'→3') | Expected length (bp) |
| | AAGATCACGCCACTGGTATTTACCTGCAGAAAGTACTGAGTCCGGACGAAGCGCAAGGTATGTTTTCTGT TAATGTAGATACTGCTAAACAGGTTGAACGTCTGGATCAGGAAATTGCTTCTCTGTCTCAGCACGTCTTC CAGAAGAGCCACACATGGCACCTTTGCTGCTGGAAAGGATTAAAGTATTCCA (SEQ ID NO: 186) | |
| 7-d | TTACATGCTTTCGACACATACAGCAGGTCGCAGGGTCATGTGTTCGCAGTGGGTTGAACGTCTGGATCAG GAAATTGCTTCTCTGTCTCAGCACGTCTTCCGCCTGGACGACGAACTGCCGTGGGAGGCGCGCATCCTGA AACTGGAATCTGGCGGTCTGTACCTGATCTTGGCCTTCCACCACACCTGCTTCGATGCATGGAGCCTGAA AGTTTTCGAACAGGAGCTGCGCGCGCTGTACGCAGCGCTTCAGAAAACGAAATCTGCAGCGAACTTACCG GCATTAAAAGCACAGTATAAGGAATACGCTCTGTACCACCGCCGCCAGCTTAGCGGCGACCGCATGCGTA ACACAGCCAGCCTGCATTAGTCGGTGCTGCTGAAAGATCCTCACACTATACA (SEQ ID NO: 187) | 402 |
| 7-e | GTTAATTTCTGGGGATACGTCAGCAGAGGGCATCTTAGCGGTCGTTCTTCTGAATACGCTCTGTACCACC GCCGCCAGCTTAGCGGCGACCGCATGCGTAACCTGTCCGATTTCTGGTTACGTAAACTGATCGGTCTGGA ACCACTGCAGCTGATCACCGATCGTCCGCGTCCGGTTCAGTTCAAATACGACGGTGACGATCTGAGCATC GAACTGTCCAAGAAAGAGACCGAAAACCTGCGCGGCGTTGCAAAACGTTGTAAGTCTTCCTTATATGTTG TACTGGTATCTGTTTACTGTGTCATGCTGGCAAGCTACGCCAACCAGAGCGATGTTAGCGTGGGCATCCC AAGAAGACCACACATGTCACCTTTGCTGCTGCTTATAAAAAGCGTGAGTTA (SEQ ID NO: 188) | 401 |
| 7-f | TACCTGTGATCTGCGTCGTACAGCAGAGGGCATCTTAGCGGTCGCTCTTCTTGATCACCGATCGTCCGCG TCCGGTTCAGTTCAAATACGACGGTGACGATCTGAGCATCGAACTGTCCAAGAAAGAGACCGAAAACCTG CGCGGCGTTGCAAAACGTTGTAAGTCTTCCTTATATGTTGTACTGGTATCTGTTTACTGTGTCATGCTGG CAAGCTACGCCAACCAGAGCGATGTTAGCGTGGGCATCCCAGTATCACACCGTACGCACCCGCAGTTCCA GTCTGTTATCGGCTTTTTCGTTAACCTGGTCGTTCTGCGTGTAGATATCAGCCAGTCCGCTATTTGCGGT TAGAAGAGCCACACATGGCACCTTTGCTGCTGTCTTCATCGATAAATACAAA (SEQ ID NO: 189) | 402 |
| 8-a | GAAGCACCTGTCTTATTTAACAGCAGCACCGACTAATGCAGGCTGGCATGAAAACGTTGTAAGTCTTCCT TATATGTTCTGGTATCTGTTTACTGTGTCATGCTGGCAAGCTACGCCACCAGAGCGATGTTAGCGTGGGC ATCCCAGTATCACACCGTACGCACCCGCAGTTCCAGTCTGTTATCGGCTTTTTCGTTAACCTGGTCGTTC TGCGTGTAGATATCAGCCAGTCCGCTATTTGCGGTTTAATCCGTCGCGTCATGAAAGAACTGGTTGACGC GCAGCTGCACCAGGATATGCCGTTCCAGGAAGTTACGAAACTGCTGCAGGTGGATAACGATCCTAGCACT GCGAACACATGACCCTGCGACCTGCTGAAGCCTACCCGGGAAGATCA (SEQ ID NO: 190) | 397 |
| 8-b | TCATCCTATTACGATGCCCGCAGCAGCAAAGGTGCCATGTGTGGCTCTTTATGCCGTTCCAGGAAGTTAC GAAACTGCTGCAGGTGGATAACGATCCTAGCCGTCACCCGTTGGTTCAGAACGTATTTAACTTTGAGTCT CGCGCGAACGGTGAACACGATGCCCGCTCTGAAGACGAGGGCTCTCTTGCATTCAATCAGTACCGTCCGG TTCAGCCGGTTGACAGCGTGGCCAAATTCGATCTGAACGCCACCGTCACCGAACTGGAATCCGGTCTGCG TGTTAATTTCAACTACGCGACCAGCTTATTCAATAAATCCACCATCCAGGGCTTCCTGCACACATATGAA AGAAGAGGACCGCTAAGATGCCCTCTGCTGCAATAAAAAGCTTCCAACGC (SEQ ID NO: 191) | 400 |
| 8-c | ATTTATAAGGACGGGCCAGCCAGCAGAGGGCATCTTAGCGGTCGCTCTTCTCCAGCTTATTCAATAAATC CACCATCCAGGGCTTCCTGCACACATATGAATACCTTCTGCGTCAGCTGTCCGAACTGAGCGCTGAAGGC ATCAACGAAGATACCCAGCTGTCACTGGTTCGCCCGACTGAGAACGGGGATCTGCACCTGCCACTGGCCC AGTCTCCGCTCGCGACCACTGCAGAAGAACAGAAAGTTGCTTCCCTGAACCAGGCTTTCGAACGTGAAGC CTTCCTGGCGGCGGAAAAAATCGCCGTTGTTCAAGGGGACCGCGCTCTGTCGTATGCCGACCTGAACGGT CAGAAACCACACATGGCACCTTTGCTGCTGTACCAATACGGGGANCGTTT (SEQ ID NO: 192) | 400 |
| 8-d | TAATCTGATCGATGCTAGGACAGCAGGTCGCAGGGTCATGTGTTCGTAGTGCGCCGTTGTTCAAGGGGAC CGCGCTCTGTCGTATGCCGACCTGAACGGTCAGGCTAATCAACTGGCGCGTTATATCCAGTCCGTCTCCT GCATCGGTGCCGACGACGGCATCGCCCTGATGCTGGAAAAGAGCATCGATACTATCATCTGCATTCTGGC AATCTGGAAAGCAGGCGCCGCGTATGTGCCGCTGGATCCGACCTACCCACCAGGCCGTGTACAACTGATC CTGGAGGAAATCAAAGCGAAAGCTGTGCTGGTACACTCTTCCCACGCCTCTAAATGTGAACGTCACGGTG CCACTGCCAGCCTGCATTAGTCGGTGCTGCTGTTAGGAGGATTGAATCAAAA (SEQ ID NO: 193) | 402 |
| 9-a | TAGCCCTTTTCGTATTTGCATCAGCAGCAAAGGTGCCATGTGTGGCTCTTTCCTACCCACCAGGCCGTGT ACAACTGATCCTGGATGAAATCAAAGCGAAACTGTGCTGGTACACTCTTCCACGCCTCTAAATGTGAACG TCACGGTGCCAAAGTCATTGCAGTAGACTCTCCGGCTATTGAAACGGCAGTGAGCCAGCAGTCTGCAGCT GATCTGCCGACCATTGCTAGCCTGGGTAATCTGGCATATATCATCTTTACTAGCGGCACTTCTGGCAAAC CGAAAGGCGTTCTGGTAGAGCAAAAAGCCGTTCTGCTGCTGCGCGACGCCCTGCGTGAGCGTTACTTCGA GAAGAGCGACCGCTAAGATGCCCTCTGCTGTAGACTGAGTTGAACAACTA (SEQ ID NO: 194) | 400 |
| 9-b | ATCATTGCACTTGTTGTTCGCAGCAGCAAAGGTGCCATGTGTGGCTCTTCTATCATCTTTACTAGCGGCA CTTCTGGCAAACCGAAAGGCGTTCTGGTAGAGCAAAAAGCCGTTCTGCTGCTGCGCGACGCCCTGCGTGA GCGTTACTTCGGTCGTGATTGTACCAAACATCACGGTGTTCTGTTCCTGAGCAACTACGTTTTCGACTTC TCCGTAGAACAGCTGGTTCTGTCTGTACTCTCAGGCCACAAACTGATTGTCCCGCCGGCGGAGTTTGTGG CGGATGACGAATTCTATCGTATGGCCTCTACCCACGGTCTTTCTTACCTGTCTGGCACCCCGAGCCTGCT TAGAAGAGCGACCGCTAAGATGCCCTCTGCTGAAATCAGTAAAAAACCTTCC (SEQ ID NO: 195) | 402 |
| 9-c | TTATTCGTGGATTGGTGTTCCAGCAGAGGGCATCTTAGCGGTCGCTCTTCTTTCGACTTCTCCGTAGAAC AGCTGGTTCTGTCTGTACTCTCAGGCCACAAACTGATTGTCCCGCCGGCGGAGTTTGTGGCGGATGACGA ATTCTATCGTATGGCCTCTACCCACGGTCTTTCTTACCTGTCTGGCACCCCGAGCCTGCTTCAAAAAATC GATCTGGCACGTCTGGATCACCTGCAGGTTGTAACCGCGGCGGGTGAGGAACTCCACGCGACCCAGTACG AAAAAATGCGTCGTCGTTTTAACGGTCCAATCTACAACGCTTATGGTGTTACCGAGACAACGGTGTACAA CAGAAGAACCACACATGGCACCTTTGCTGCTGTAATCAGAACCTAGAAAAAT (SEQ ID NO: 196) | 402 |

TABLE 2-continued

Sequences of daughter fragments obtained after PCR recovery

| Fragment (Daughter fragment) | Sequence(5'→3') | Expected length (bp) |
|---|---|---|
| 9-d | TGATTTCACCACTAAGTCTCAGCAGGTCGCAGGGTCATGTGTTCGCAGTGACGGTCCAATCTACAACGCT<br>TATGGTGTTACCGAGACAACGGTGTACAACATCATCGCTGAATTCACCACCAACTCCATCTTCGAAAACG<br>CATTACGCGAAGTCCTGCCGGGCACCCGTGCGTACGTTCTGAACGCGGCGCTGCAGCCGGTTCCATTCGA<br>CGCTGTGGGTGAACTGTATCTGGCCGGCGATAGCGTAACCCGTGGTTACCTGAACCAGCCGTTGCTGACC<br>GATCAGCGTTTCATCCCTAACCCGTTCTGCAAGGAAGAAGACATCGCGATGGGTCGTTTCGCTCGTCTGT<br>CACGCCAGCCTGCATTAGTCGGTGCTGCTGGCACGAGAAATAAAGGAGG (SEQ ID NO: 197) | 399 |
| 9-e | TAAAGTTATCATGTGCTACCCAGCAGCAAAGGTGCCATGTGTGGCTCTTCTACAAAACCGGCGACCTGGT<br>TCGCTCTCGCTTCAACCGCCAGCAGCAGCCGCAGCTGGAATACCTGGGCCGTGGCGACCTGCAGATTAAA<br>ATGCGTGGTTACCGCATTGAAATTAGCGAAGTACAGAACGTGCTGACCTCCTCCCCGGGCGTACGCGAAG<br>GTGCGGTTGTGGCTAAATATGAAAACAACGACACGTATAGCCGTACTGCACATTCCTTAGTCGGTTATTA<br>TACCACTGATAACGAAACAGTTTCAGAAGCTGATATCCTCACCTTCATGAAAGCGCGTCTGCCGACCTAT<br>AAGAAGAGGACCGCTAAGATGCCCTCTGCTGGAGATGAATATAGGTTTACA (SEQ ID NO: 198) | 401 |
| 9-f | GTTCATTGCATAATGCTTCTCAGCAGCACCGACTAATGCAGGCTGGAGTGTTCCATTCGACGCTGTGGGT<br>GAACTGTATCTGGCCGGCGATAGCGTAACCCGTGGTTACCTGAACCAGCCGTTGCTGACCGATCAGCGTT<br>TCATAACTAACCCGTTCTGCAAGGAAGAAGACATCGCGATGGGTCGTTTCGCTCGTCTGTACAAAACCGG<br>CGACCTGGTTCGCTCTCGCTTCAACCGCCAGCAGCAGCCGCAGCTGGAATACCTGGGCCGTGGCGACCTG<br>CAGATTAAAATGCGTGGTTACCGCATTGAAATTAGCGAAGTACAGAACGTGCTGACCTCCTCCCGGGCGC<br>ATGCGAACACATGACCCTGCGACCTGCTGCTGGATGTAAAGGGNTTTAA (SEQ ID NO: 199) | 399 |
| 9-g | ATTGATATGTAAGAGATTTCCAGCAGCAAAGGTGCCATGTGTGGCTCTTATCGTACTGCACATTCCTTAG<br>TCGGTTATTATACCACTGATAACGAAACAGTTTCAGAAGCTGATATCCTCACCTTCATGAAAGCGCGTCT<br>GCCGACCTATATGGTGCCTTCTCACCTGTGCTGCCTGGAAGGTGCTCTGCCAGTCACTATTAACGGTAAA<br>CTGGACGTTCGTCGTCTGCCTGAAATTATCAACGACAGTGCGCAATCCTCATATTCCCCGCCGCGCAACA<br>TTATCGAAGCGAAAATGTGCCGTTTATGGGAAAGCGCGCTGGGTATGGAACGCTGCGGTATTGACGATGA<br>CAGAAGAGCGACCGCTAAGATGCCCTCTGCTGAACGAAAATGGTACCTATT (SEQ ID NO: 200) | 401 |
| 10-a | GATTACTACATTTTTCTCAACAGCAGCACCGACTAATGCAGGCTGGCAGTGAACGGTAAACTGGACGTTC<br>GTCGTCTGCCTGAAATTATCAACGACAGTGCGAATCCTCATATTCCCCGCCGCGCAACATTATCGAAGCG<br>AAAATGTGCGTTTATGGGAAAGCGCGCTGGGTATGGAACGCTGCGGTATTGACGATGACCTCTTCAAGCT<br>GGGGGGGGATTCTATCACCAGTCTGCACCTCGTCGCACAGATTCACAATCAGGTGGGCTGTAAGATTACC<br>GTGCGCGATATTTTCGAACACCGTACCGCGCGTGCTCTCCACGATCACGTTTTCATGAAGGATAGCGATC<br>ATGCGAACACATGACCCTGCGACCTGCTGGCCCAACCCCCCCCAAAAG (SEQ ID NO: 201) | 398 |
| 10-b | AATTGGTTACCTCTATCCCCCAGCAGCAAAGGTGCCATGTGTGGCTCTTCTACCGTACCGCGCGTGCTCT<br>CCACGATCACGTTTTCATGAAGGATAGCGATCGCTCTAACGTCACCCAGTTCCGTACCGAGCAGGGGCCG<br>GTCATTGGCGAAGCTCCGCTGCTGCCGATCCAGGATTGGTTCTTGAGCAAAGCTCTGCAGCACCCTATGT<br>ACTGGAACCACACGTTCTACGTACGTACCCCGGAACTGGACGTTGATTCCCTGAGTGCGGCCGTTCGTGA<br>CCTGCAGCAGTACCACGACGTTTTCCGCATGCGCCTGAAACGCGAAGAAGTTGGCTTTGTACAGTCCTTT<br>GAGAAGAGCGACCGCTAAGATGCCCTCTGCTGAAATCGGATCCCAGTATGAG (SEQ ID NO: 202) | 402 |
| 10-c | GCATAAAGCGGGAGGCTTCTCAGCAGAGGGCATCTTAGCGGTCGCTCTTCTTTTCCGCATGCGCCTGAAA<br>CGCGAAGAAGTTGGCTTTGTACAGTCCTTTGCCGAAGACTTTTCCCCGGCGCAGCTGCGTGTACTGAACG<br>TGAAGGACGTGGATGGTAGCGCGGCGGTTAACGAAATCCTGGACGGTTGGCAAAGCGGCTTCAACCTGGA<br>AAACGGTCCGATCGGCTCGATCGGTTATCTGCATGGCTATGAAGACCGCTCCGCACGTGTGTGGTTTTCT<br>GTACACCACATGGCCATTGACACTGTTTCCTGGCAGATCCTGGTTCGTGATCTGCAGACTCTGTACCGTA<br>AAGAAGAACCACACATGGCACCTTTGCTGCTGGCACTATTCTATGACACAG (SEQ ID NO: 203) | 401 |
| 10-d | TTTCGACCGATTTCAGTCTGCAGCAGGTCGCAGGGTTATGTGTTCGCAGTGCAACCTGGAAAACGGTCCG<br>ATCGGCTCGATCGGTTATCTGCATGGCTATGAAGACCGCTCCGCACGTGTGTGGTTTTCTGTACACCACA<br>TGGCCATTGACACTGTTTCCTGGCAGATCCTGGTTCGTGATCTGCAGACTCTGTACCGTAACGGTTCCCT<br>GGGTTCCAAAGGTTCTTCATTTCGCCAATGGGCCGAGGCAATCCAAAACTACAAAGCGAGCGACTCGGAA<br>CGTAACCATTGGAACAAGCTGGTTATGGAAACTGCATCGTCGATCAGCGCGCTGCCGACCTCCACTGGTT<br>CCACTACCAGCCTGCATTAGTCGGTGCTGCTGTAATTACCGTCAAAAAA (SEQ ID NO: 204) | 399 |
| 10-e | CTTCCTGTGGGTTTTCTACAGCAGCAAAGGTGCCATGTGTGGCTCTTCTTCCAAAACTACAAAGCGAGCG<br>ACTCGGAACGTAACCATTGGAACAAGCTGGTTATGGAAACTGCATCGTCGATCAGCGCGCTGCCGACCTC<br>CACTGGTTCTCGCGTACGTCTCTCCCGTTCTCTGTCTCCTGAAAAAACTGCTTCTCTGATCCAGGGTGGC<br>ATCGATCGTCAGGATGTAAGCGTATACGATTCTCTGCTGACTTCTGTTGGCCTGGCTTTGCAACACATCG<br>CGCCGACTGGCCCGTCTATGGTTACAATCGAGGGTCACGGCCGCGAAGAAGTTGACCAGACCCTGGATGA<br>GAAGAGCGACCGCTAAGATGCCCTCTGCTGAATACGCGAATGATGTAAAA (SEQ ID NO: 205) | 400 |
| 10-1 | TTTTTGAGCTACGCTTTCGGCAGCAGCAAAGGTGCCATGTGTGGCTCTTCTACTTCTGTTGGCCTGGCTT<br>TGCAACACATCGCGCCGACTGGCCCGTCTATGGTTACAATCGAGGGTCACGGCCGCGAAGAAGTTGACCA<br>GACCCTGGATGTTTCTCGTACGATGGGCTGGTTCACTACCATGTATCCGTTCGAAATCCCGCGTCTGTCG<br>ACGGAAAACATCGTGCAGGGTGTTGTTGCTGTAAGTGAACGCTTCCGCCAAGTTCCGGCTCGCGGTGTTG<br>AGTTATGGTACTCTGTACGGTTACACCCAGCACCCTCTGCCGCAGGTTACTGTTAACTACCTGGGCCAGC<br>TGGAAGGACCGCTAAGATGCCCTCTGCTGCTGAAAGTAGAATGTATTGA (SEQ ID NO: 206) | 399 |
| 11-a | GTCAGTAGTATACCGTTCGTCAGCAGAGGGCATCTTAGCGGTCGCTCTTCTACACCCAGCACCCTCTGCC<br>GCAGGTTACTGTTAACTACCTGGGCCAGCTGGCTCGTAAACAGAGCAAGCCGAAAGAATGGGTTCTGGCA<br>GTTGGTGATAACGAGTTCGAGTACGGTCTGATGACCTCCCCGGAGGATAAGGACCGTTCGAGCTCCGCAG<br>TGGATGTTACGGCCGTCTGCATCGACGGGACGATGATCATCGATGTGGACTCGGCTTGGTCTTTGGAAGA | 401 |

TABLE 2-continued

Sequences of daughter fragments obtained after PCR recovery

| Fragment (Daughter fragment) | Sequence (5'→3') | Expected length (bp) |
|---|---|---|
| | ATCTGAACAGTTCATCTCGTCAATTGAAGAAGGTCTGAACAAAATCCTGGACGGTCGTGCATCCCAGCAG AAGAAAGCCACACATGGCACCTTTGCTGCTGAGGAAGGCAATCTTAGATCG (SEQ ID NO: 207) | |
| 11-9 | TTCTGCAGAACGTTTTTGTAACAGCAGCAAAGGTGCCATGTGTGGCTCTTCTGCTCGTAAACAGAGCAAG CCGAAAGAATGGGTTCTGGCAGTTGGTGATAACGAGTTCGAGTACGGTCTGATGACCTCCCCGGAGGATA AGGACCGTTCGAGCTCCGCAGTGGATGTTACGGCCGTCTGCATCGACGGGACGATGATCATCGATGTGGA CTCGGCTTGGTCTTTGGAAGAATCTGAACAGTTCATCTCGTCAATTGAAGAAGGTCTGAACAAAATCCTG GACGGTCGTGCATCCCAGCAGACTAGCCGCTTTCCGGATGTGCCGCAGCCAGCAGAGACCTACACCCCAT ACAGAAGAGTGACCGCTAAGATGCCCTCTGCTGGATGGGCCATAATACCGTCG (SEQ ID NO: 208) | 403 |
| 11-c | ATCTTTTATGTACTTTGTGACAGCAGAGGGCATCTTAGCGGTCGCTCTTCTGATGTGGACTCGGCTTGGT CTTTGGAAGAATCTGAACAGTTCATCTCGTCAATTGAAGAAGGTCTGAACAAAATCCTGGACGGTCGTGC ATCCCAGCAGACTAGCCGCTTTCCGGATGTGCCGCAGCCAGCAGAGACCTACACCCCATACTTCGAATAT CTGGAACCGCCGCGCCAGGGCCCGACCCTGTTTCTGCTGCCACCGGGTGAAGGTGGTGCGGAATCTTACT TCAACAACATCGTCAAACGCTTGCGTCAAACTAACATGGTTGTCTTTAACAACTACTACCTGCACTCCAA AAGAAGAGCCACACATGGCACCTTTGCTGCTGACACTAAAAGTGTTGAAAAA (SEQ ID NO: 209) | 402 |
| 11-d | TAATTTCCTGTGCAACTCAGCAGCAAAGGTGCCATGTGTGGCTCTTCTTTCGAATATCTGGAACCGCCGC GCCAGGGCCCGACCCTGTTTCTGCTGCCACCGGGTGAAGGTGGTGCGGAATCTTACTTCAACAACATCGT CAAACGCTTGCGTCAAACTAACATGGTTGTCTTTAACAACTACTACCTGCACTCCAAACGTCTGCGCACC TTCGAGGAACTGGCTGAAATGTATCTGGACCAGGTACGCGGCATCCAACCGCACGGTCCATACCACTTCA TCGGCTGGAGCTTCGGGGGCATTCTGGCGATGGAGATGTCCCGTCGTCTGGTTGCGAGCGACGAAAAAGA AGAGCGACCGCTAAGATGCCCTCTGCTGACCCAAAGAAATAAACAAGA (SEQ ID NO: 210) | 398 |
| 11-e | ATGTATCCTCGCTCTTTAACCAGCATCACCGACTAATGCAGGCTGGCAGTGGCATTCTGGCGATGGAGAT GTCCCGTCGTCTGGTTGCGAGCGACGAAAAATTGGTTTCTGGGTATTATCGACACCTATTTCAACGTACG TGGTGCCACTCGCACCATTGGCCTTGGTGATACTGAAATCCTGGATCCGATCCACCACATCTATAACCCG GACCCGGCAAACTTTCAGCGTCTGCCGTCTGCCACCGACCGTATCGTCCTGTTTAAGGCCATGCGTCCGA ATAATAAATATGAATCAGAAACCAGCGTCGCCTGTATGAGTACTACGACACTGCGAACACATGACCCTGC GACCTGCTGAGTAATAATCAAACCGGGTG (SEQ ID NO: 211) | 379 |
| 11-1 | CTAACGCATTGTCAGGTTTCCAGCAGCACCGACTAATGCAGGCTGGCAGTGCGTATCGTCCTGTTTAAGG CCATGCGTCCGAATAATAAATATGAATCAGAAAACCAGCGTCGCCCTACGACGCGTTAGATTCCACGGAC TGGACCGCATGTTACCAGGCGATCCCTACCTCCTCATGGTCGCGCCTGCGCACGATCCACACCTTCCCGG GTTCGGAAATCCACAACCGCTGGTCCCGTTGCGTTCGTCTGAGCCGTAACACCAGCCTTGCCATCGACCC GTCTCTGGCAGCTCAGTACATCGGTCGTTGGAAGTAAGCAGAGTAAAGACCGTGCACTTATCACTGGAAC ACATGACCCTGCGACCTGCTGTTCTACACTGGTATCCGGAGT (SEQ ID NO: 212) | 392 |

The desired PCR amplification products were electrophoresed through an agarose gel to excise bands of the desired size, and DNA was purified using a gel purification kit (AccuPrep™, Bioneer, Korea). For the construction of ~1,000 bp DNA sequence, 3-8 gel-purified gene fragments were pooled. For each pool, restriction enzyme digestion was carried out as follows: when EarI or EcoP15I was used, 2 μl EarI or EcoP15I, 5 μl NEB buffer, 0.5 μl 100×BSA, 10 μl water, and 30 μl purified (and pooled) DNA fragments were mixed, followed by digestion at 37° C. for 3 h (for EcoP15I, 10 ATP was further added); and when BtsI was used, 2 μl BtsI, 5 μl NEB buffer, 0.5 μl 100×BSA, 10 μl water, and 30 μl PCR products were mixed, followed by digestion at 55° C. for 3 h. The restriction digest products were electrophoresed through 1.5% agarose gels to obtain expected bands (daughter fragments, 300 bp; FIG. 8*h*). The expected DNA fragment sequences after digestion (products obtained after Type IIS restriction enzyme digestion or error-correction PCR) are listed in Table 3.

TABLE 3

Sequences of daughter fragments obtained after Type IIS restriction enzyme digestion or nested PCR

| Fragment (Daughter fragment) | Sequence (5'→3') | Expected Length (Bp) |
|---|---|---|
| 1-a | ATGACCCAATTGAAGCCGCCTAACGGGACCACTCCGATCGGCTTCAGCGCCACTACTAGCCTGAACGCTAGCG GCTCTTCCTCGGTTAAGAATGGTACCATCAAGCCTTCGAATGGTATCTTCAAACCTTCTACTCGTGACACCAT GGACCCGTGCTCGGGCAACGCCGCTGACGGCTCCATTCGCGTACGTTTTCGCGGTGGCATCGAACGTTGGAAA GAGTGTGTAAACCAAGTGCCGGAGCGTTGCGACCTGTCTGGTCTGACCACGGACAGCACCCGCTACCAGCTGG CTTCGA (SEQ ID NO: 213) | 298 |
| 1-b | CTGTCTGGTCTGACCACGGACAGCACCCGCTACCAGCTGGCTTCGACCGGCTTCGGCGACGCGAGCGCGGCTT ACCAGGAACGTCTGATGACTGTGCCGGTAGATGTTCATGCTGCGCTCCAGGAGCTGTGCCTGGAACGCCGCGT CTCTGTGGGTTCTGTGATCAACTTCAGCGTTCACCAGATGCTGAAGGGTTTTGGCAACGGTACTCACACTATC ACCGCGAGCCTGCACCGCGAACAGAATCTGCAGAACTCCTCTCCGTCTTGGGTCGTTTCCCCTACTATCGTGA CCCATG (SEQ ID NO: 219) | 298 |

TABLE 3-continued

Sequences of daughter fragments obtained after Type IIS restriction enzyme digestion or nested PCR

| Fragment (Daughter fragment) | Sequence(5'→3') | Expected Length (Bp) |
|---|---|---|
| 1-c | AACGGTACTCACACTATCACCGCGAGCCTGCACCGCGAACAGAATCTGCAGAACTCCTCTCCGTCTTGGGTCG<br>TTTCCCCTACTATCGTGACCCATGAAAACCGCGATGGCTGGTCAGTGGCGCAGGCAGTGGAGTCTATCGAGGC<br>TGGTCGTGGCTCCGAAAAGGAATCTGTGACCGCGATTGATTCCGGCTCCTCCCTGGTCAAAATGGGTCTGTTC<br>GATCTGCTGGTTTCCTTCGTCGATGCGGATGACGCGCGTATCCCTTGCTTCGACTTTCCGCTGGCTGTTATTG<br>TGCGC (SEQ ID NO: 215) | 297 |
| 1-d | TGACGCGCGTATCCCTTGCTTCGACTTTCCGCTGGCTGTTATTGTGCGCGAGTGCGATGCAAACCTGTCTCTC<br>ACCCTTCGCTTCTCGGACTGCCTGTTCAACGAGGAAACCATTTGTAATTTCACGGATGCCCTCAATATCCTGT<br>TGGCTGAGGCAGTTATCGGT (SEQ ID NO: 216) | 166 |
| 1-e | ACGAGGAAACCATTTGTAATTTCACGGATGCCCTCAATATCCTGTTGGCTGAGGCAGTTATCGGTCGTGTAAC<br>TCCGGTAGCCGATATCGAGCTGCTGTCTGCAGAGCAGAAACAACAGCTGGAGGAATGGAACAACACCGATGGT<br>GAATATCCGTCTAGCAAGCGTCTGCACCACCT (SEQ ID NO: 217) | 178 |
| 2-a | GTGAATATCCGTCTAGCAAGCGTCTGCACCACCTGATTGAAGAGGTGGTGGAACGTCACGAAGACAAAATCGC<br>TGTGGTGTGCGACGAACGTGAACTG (SEQ ID NO: 218) | 98 |
| 2-b | TCACGAAGACAAAATCGCTGTGGTGTGCGACGAACGTGAACTGACTTACGGTGAACTCAATGCCCAGGGCAAC<br>TCCCTGGCGCGTTACCTGCGCAGCATTGGTATTCTGCCTGAACAGCTGGTTGCGCTGTTTCTGGACAAATCCG<br>AAAAATTGATCGTAACCATCCTGGGCGTCTGGAAATCCGGTGCTGCTTACGTGCCAATTGACCCGACCTACCC<br>TGACGAACGTGTTCGTTTCGTTCTGGACGACACGAAAGCCCGTGCGATTATCGCTTCCAATCAGCATGTTGAA<br>CGCCT (SEQ ID NO: 219) | 297 |
| 2-c | TGATCGTAACCATCCTGGGCGTCTGGAAATCCGGTGCTGCTTACGTGCCAATTGACCCGACCTACCCTGACGA<br>ACGTGTTCGTTTCGTTCTGGACGACACGAAAGCCCGTGCGATTATCGCTTCCAATCAGCATGTTGAACGCCTC<br>CAGCGTGAAGTAATCGGTGATCGCAACCTGTGCATCATCCGTCTCGAACCACTGCTGGCGAGCCTTGCGCAGG<br>ATTCTTCTAAATTCCCTGCCCACAACCTGGATGATTTGCCGCTGACCAGCCAGCAGCTGGCGTACGTTACTTA<br>TACCA (SEQ ID NO: 220) | 297 |
| 2-d | AGCGTGAAGTAATCGGTGATCGCAACCTGTGCATCATCCGTCTCGAACCACTGCTGGCGAGCCTTGCGCAGGA<br>TTCTTCTAAATTCCCTGCCCACAACCTGGATGATTTGCCGCTGACCAGCCAGCAGCTGGCGTACGTTACTTAT<br>ACCAGCGGTACCACCGGCTTTCCGAAAGGCATTTTCAAACAGCACACTAACGTTGTTAACTCCATCACAGACC<br>TGTCCGCTCGTTACGGTGTTGCAGGTCAACACCATGAAGCTATCCTGCTCTTCAGTGCTTGCGTTTTCGAACC<br>GTTCG (SEQ ID NO: 221) | 297 |
| 2-e | GTTAACTCCATCACAGACCTGTCCGCTCGTTACGGTGTTGCAGGTCAACACCATGAAGCTATCCTGCTCTTCA<br>GTGCTTGCGTTTTCGAACCGTTCGTTCGTCAGACTCTGATGGCCCTGGTGAACGGTCACCTGCTCGCCGTGAT<br>TAACGATGTAGAAAAAATATGACGCTGACACCCTCCTCCCATTTATCCGCCGTCACTCTATCACCTATCTGAAC<br>GGTACTGCGTCGGTTCTCCAAGAGTATGACTTCTCTGACTGTCCGAGCCTGAACCGTATCAT<br>(SEQ ID NO: 222) | 281 |
| 2-f | CTATCACCTATCTGAACGGTACTGCGTCGGTTCTCCAAGAGTATGACTTCTCTGACTGTCCGAGCCTGAACCG<br>TATCATCCTGGTGGGCGAGAACCTGACCGAAGCACGTTACCTGGCACTGCGTCAGCGTTTCAAAAATCGTATT<br>CTGAACGAGTACGGTTTCACCGAGTCTGCGTTCGTGACTGCGCTGAAAATTTTCGATCCGGAAAGCACCCGCA<br>AAGATACCTCCCTGGGGCGTCCGGTGCGCAATGTTAAATGCTATATCTTGAACCCTAGCCTGAAACGCGTGCC<br>AAT (SEQ ID NO: 223) | 295 |
| 2-g | ACGAGTACGGTTTCACCGAGTCTGCGTTCGTGACTGCGCTGAAAATTTTCGATCCGGAAAGCACCCGCAAAGA<br>TACCTCCCTGGGGCGTCCGGTGCGCAATGTTAAATGCTATATCTTGAACCCTAGCCTGAAACGCGTGCCAATT<br>GGTGCTACAGGTGAGCTGCATATTGGCGGCCTGGGTATCTCCAAGGGTTACTTGAATCGTCCGGAACTGACGC<br>CGCACCGCTTCATCCCGAACCCGTTTCAGACCGATTGCGAAAAACAGCTGGGTATCAACTCTCTGATGTACAA<br>AACCG (SEQ ID NO: 224) | 297 |
| 3-a | ATCGTCCGGAACTGACGCCGCACCGCTTCATCCCGAACCCGTTTCAGACCGATTGCGAAAAACAGCTGGGTAT<br>CAACTCTCTGATGTACAAAACCGGTGATCTGGCTCGCTGGCTCCCGAACGGTGAAGTTGAATACCTGGGCCGT<br>GCGGATTTCCAGATCAAACTGCGCGGTATTCGTATTGAGCCGGGCGAAATCGAGACTATGCTGGCGATGTATC<br>CGCGCGTTCGTACCTCCCTGGTGGTTTCCAAGAAATTACGTAACGGTCCTGAAGAAACAACGAACGAACACCT<br>GGTAG (SEQ ID NO: 225) | 297 |
| 3-b | CGGATTTCCAGATCAAACTGCGCGGTATTCGTATTGAGCCGGGCGAAATCGAGACTATGCTGGCGATGTATCC<br>GCGCGTTCGTACCTCCCTGGTGGTTTCCAAGAAATTACGTAACGGTCCTGAAGAAACAACGAACGAACACCTG<br>GTAGGCTACTACGTATGCGACTCCGCATCTGTTTCCGAAGCGGATCTGCTGTCCTTCCTGGAGAAGAAGCTGC<br>CGCGTTATATGATTCCGACTCGTCTGGTACAGCTGAGCCAGATCCCGGTTAACGTCAACGGTAAAGCCGATCT<br>GCGTG (SEQ ID NO: 226) | 297 |
| 3-c | TTCCTGGAGAAGAAGCTGCCGCGTTATATGATTCCGACTCGTCTGGTACAGCTGAGCCAGATCCCGGTTAACG<br>TCAACGGTAAAGCCGATCTGCGTGCTCTGCCGGCGGTTGATATCTCCAACAGCACCGAAGTTCGTTCTGATCT<br>GCGTGGTGATACCGAAATTGCCCTCGGCGAAATCTGGGCGGACGTGCTGGGCGCGCGTCAGCGTTCGGTTAGC<br>CGTAACGATAACTTTTTCCGCCTCGGTGGCCACTCTATCACCTGCATCCAGCTGATTGCGCGTATCCGTCAGC<br>GTCAGC (SEQ ID NO: 227) | 298 |
| 4-a | ACCTGCATCCAGCTGATTGCGCGTATCCGTCAGCGTCAGCGTTTGTCTGTGTCTATCTCTGTGGAAGACGTGT<br>TTGCTACACGCACTCTTGAGCGTATGGCCGACCTGTTGCAAAACAAACAGCAAGAGAAATGCGACAAACCACA | 307 |

TABLE 3-continued

Sequences of daughter fragments obtained after Type IIS restriction enzyme digestion or nested PCR

| Fragment (Daughter fragment) | Sequence(5'→3') | Expected Length (Bp) |
|---|---|---|
| | CGAAGCACCGACTGAACTGCTTGAAGAAAACGCTGCGACTGATAACATCTACCTGGCGAACAGCCTGCAGCAA<br>GGTTTCGTCTACCATTACCTGAAAAGCATGGAACAAAGTGATGCTTATGTAATGCAGAGCGTTCTGCGTTACA<br>ACACCACCCTTTCCC (SEQ ID NO: 228) | |
| 4-b | CATGGAACAAAGTGATGCTTATGTAATGCAGAGCGTTCTGCGTTACAACACCACCCTTTCCCCGGATCTGTTC<br>CAGCGTGCCTGGAAACACGCGCAGCAAAGCTTCCCGGCTCTGCGTCTGCGCTTCTCTTGGGAAAAAGAAGTCT<br>TCCAGCTGCTGGA (SEQ ID NO: 229) | 159 |
| 4-c | AAAGCTTCCCGGCTCTGCGTCTGCGCTTCTCTTGGGAAAAAGAAGTCTTCCAGCTGCTGGATCAGGACCCGCC<br>TCTGGACTGGCGTTTCCTCTACTTCACTGATGTGGCGGCTGGTGCAGTAGAAGACCGTAAACTGGAAGATTTA<br>CGCC (SEQ ID NO: 230) | 150 |
| 4-d | CTGGTGCAGTAGAAGACCGTAAACTGGAAGATTTACGCCGCCAGGACCTCACCGAGCGTTTTAAACTGGATGT<br>GGGCCGTCTGTTTCGCGTTTACCTGATCAAACACAGCGAAAACCGTTTCACTTGTCTGTTCTCTTGTCACCAC<br>GCTATCCTGGACGGCTGGTCCTTACCGCTTCTGTTCGAAAAA (SEQ ID NO: 231) | 188 |
| 4-e | CGTTTACCTGATCAAACACAGCGAAAACCGTTTCACTTGTCTGTTCTCTTGTCACCACGCTATCCTGGACGGC<br>TGGTCCTTACCGCTTCTGTTCGAAAAAGTACACGAAACATACCTGCAACTGCTGCACGGCGATAACCTGACCT<br>CCTCTATGGATGATCCATACACCCGTACCCAACGCTACCTGCATGCGCACCGCGAAGATCACCTCGACTTTTG<br>GGCTGGCGTGGTGCAGAAAATCAACGAACGTTGCGATATGAATGCTCTGTTAAACGAACGCAGCCGCTATAAA<br>GTGCAGCT (SEQ ID NO: 232) | 300 |
| 4-f | TGCTCTGTTAAACGAACGCAGCCGCTATAAAGTGCAGCTGGCCGACTACGATCAGGTACAGGAACAGCGTCAG<br>CTGACGATCGCTCTGAGCGGTGACGCGTGGCTGGCGGATCTGCGCCAGACATGCAGTGCGCAGGGCATCACGC<br>TGCACTCTATCCTGCAATTTGTATGGCATGCAGTTCTGCATGCCTACGGTGGCGGTACTCACACTATCACTGG<br>CACCACTATTTCTGGTCGCAA (SEQ ID NO: 233) | 240 |
| 5-a | ACGGTGGCGGTACTCACACTATCACTGGCACCACTATTTCTGGTCGCAACCTCCCGATCCTGGGTATCGAGCG<br>TGCGGTAGGCCCGTACATTAACACCCTGCCGTTAGTGTTGGACCATTCTACTTTTAAAGACAAGACGATCATG<br>GAAGCTATTGAAGACGTCCAAGCGAAGGTGAATGTTATGAACTCCCGTGGTAATGTAGAACTGGGTCGCCTGC<br>ACAAAACCGACCTGAAACATGGCCTGTTCGATTCTCTGTTTGTGCTGGAAAACTATCCAAACC<br>(SEQ ID NO: 234) | 282 |
| 5-b | GCTATTGAAGACGTCCAAGCGAAGGTGAATGTTATGAACTCCCGTGGTAATGTAGAACTGGGTCGCCTGCACA<br>AAACCGACCTGAAACATGGCCTGTTCGATTCTCTGTTTGTGCTGGAAAACTATCCAAACCTGGATAAATCCCG<br>TACTCTGGAGCACCAAACTGAACTGGGTTACTCCATCGAGGGTGGTACCGAAAAACTGAACTATCCGCTGGCG<br>GTGATTGCTCGTGAGGTTGAGACCACTGGCGGCTTTACTGTTAGCATCTGCTATGCGAGCGAACTGTTTGAAG<br>AGGTGA (SEQ ID NO: 235) | 298 |
| 5-c | AACTGAACTATCCGCTGGCGGTGATTGCTCGTGAGGTTGAGACCACTGGCGGCTTTACTGTTAGCATCTGCTA<br>TGCGAGCGAACTGTTTGAAGAGGTGATGATCAGCGAGCTTCTCCATATGGTACAGGATACCCTGATGCAGGTT<br>GCACGCGGGCTCAACGAACCTGTGGGCTCCCTGGAATACCTGTCTTCCATCCAGTTAGAGCAGCTGGCAGCGT<br>GGAACGCCACCGAAGCGGAGTTCCCGGACACGACCCTGCATGAAATGTTCGAGAACGAAGCATCTCAAAAGCC<br>GGATAA (SEQ ID NO: 236) | 298 |
| 5-d | TTAGAGCAGCTGGCAGCGTGGAACGCCACCGAAGCGGAGTTCCCGGACACGACCCTGCATGAAATGTTCGAGA<br>ACGAAGCATCTCAAAAGCCGGATAAAATTGCAGTCGTGTACGAAGAAACCTCTCTGACCTATCGCGAGCTGAA<br>CGAACGTGCCAATCGCATGGCGCACCAGCTGCGTTCCGACGTTTCTCCGAACCCGAACGAAGTGATCGCGCTG<br>GTTATGGACAAGAGTGAACACATGATCGTAAATATCTTGGCTGTGTGGAAATCTGGTGGCGCATACGTGCCGA<br>TCGATC (SEQ ID NO: 237) | 298 |
| 5-e | GAGTGAACACATGATCGTAAATATCTTGGCTGTGTGGAAATCTGGTGGCGCATACGTGCCGATCGATCCGGGC<br>TACCCGAATGACCGTATTCAGTATATCCTCGAGGACACTCAGGCGTTGGCTGTTATCGCAGATTCTTGTTACC<br>TGCCTCGTATCAAAGGTATGGCCGCGTCTGGTACGCTGCTCTACCCGTCTGTCCTGCCGGCAAACCCAGACAG<br>CAAATGGTCTGTGTCAAACCCGTCGCCGCTGTCTCGTAGCACCGACCTG (SEQ ID NO: 238) | 268 |
| 5-f | CGTCTGGTACGCTGCTCTACCCGTCTGTCCTGCCGGCAAACCCAGACAGCAAATGGTCTGTGTCAAACCCGTC<br>GCCGCTGTCTCGTAGCACCGACCTGGCATACATCATCTACACCTCTGGCACCACCGGCCGCCCGAAAGGCGTG<br>ACTGTGGAGCATCACGGTGTGGTGAACCTGCAGGTATCCCTGAGCAAAGTTTTTGGTCTGCGTGACACCGACG<br>ACGAAGTCATCCTGTCTTTTTCTAACTACGTTTTCGATCACTTCGTAGAACAGATGACTGATGCTATCCTGAA<br>CGGGC (SEQ ID NO: 239) | 297 |
| 6-a | CTAACTACGTTTTCGATCACTTCGTAGAACAGATGACTGATGCTATCCTGAACGGGCAGACGCTGCTGGTTCT<br>GAACGATGGTATGCGTGGTGACAAAGAACGCCTGTACCGCTACATCGAAAAGAACCGTGTAACTTATCTGTCT<br>GGTACTCCATCTGTGGTGTCTATGTATGAGTTCAGCCGTTTCAAAGACCACCTGCGCCGCGTCGATTGCGTCG<br>GTGAAGCTTTCAGCGAGCCGGTCTTCGACAAAATCCGTGAA (SEQ ID NO: 240) | 260 |
| 6-b | ACCTTCCACGGTTTGGTTATCAATGGTTATGGCCCAACTGAAGTTAGCATCACTACCCATAAGCGTTTATACC<br>CTTTCCCAGAGCGCCGCATGGATAAGTCGATCGGCCAGCAGGTCCACAACTCTACTAGCTACGTACTGAATGA<br>AGATATGAAGCGTACCCCGATCGGTGCTGTGGGTGAGCTGTACCTG (SEQ ID NO: 241) | 192 |
| 6-c | TGAATGAAGATATGAAGCGTACCCCGATCGGTGCTGTGGGTGAGCTGTACCTGGGCGGTGAAGGTGTTGTCCG<br>CGGTTATCATAATCGTGCGGATGTTACCGCCGAGCGCTTCATCCCGAACCCGTTCCAGTCTGAGGAAGATAAA | 259 |

TABLE 3-continued

Sequences of daughter fragments obtained after Type IIS restriction enzyme digestion or nested PCR

| Fragment (Daughter fragment) | Sequence(5'→3') | Expected Length (Bp) |
|---|---|---|
| | CGTGAAGGCCGTAACAGTCGCCTGTACAAGACGGGTGATCTGGTTCGCTGGATCCCGGGTAGCTCCGGCGAAGTCGAATACCTGGGTCGCAATGACTTCCAGGTTAAGATTCG (SEQ ID NO: 242) | |
| 6-d | CGAAGTCGAATACCTGGGTCGCAATGACTTCCAGGTTAAGATTCGCGGCCTCCGTATCGAGCTGGGTGAAATCGAAGCGATCCTGAGCAGCTACCACGGCATTAAACAGAGCGTAGTGATCGCAAAAGACTGCCGTGAGGGGGCACAGAAATTCCTGGTCGGCTATTACGTTGCAGACGCTGCCCTGCCGTCCGCAGCGATCCGTCGTTTCATGCAGTCGCGCCTCCCGGGTTACATGGTTCCGTCCCGTCTGATCCTGGTTTCTAAATTCCCTGTTACTCCGTCCGGGAAGCTGGA (SEQ ID NO: 243) | 297 |
| 6-e | CGTCTGATCCTGGTTTCTAAATTCCCTGTTACTCCGTCCGGGAAGCTGGACACCAAAGCACTGCCGCCGGCGGAGGAAGAAAGCGAAATCGACGTTGTTCCACCGCGCTCCGAAATTGAGCGTTCTCTCTGCGACATCTGGGCTGAACTGCTGGAAATGCACCCGGAAGAAATCGGCATTTACTCTGACTTCTTCTCCTTGGGCGGCGACAGCCTGAAATCTACTAAGTTATCCTTCATGATCCATGAGTCCTTTAACCGTGCTGTGAGCGTTAGCGCGTTATTCTGCCATCGCACA (SEQ ID NO: 244) | 297 |
| 7-a | TCCTTCATGATCCATGAGTCCTTTAACCGTGCTGTGAGCGTTAGCGCGTTATTCTGCCATCGCACAGTTGAAGCTCAAACTCACCTGATCTTGAACGACGCAGCAGATGTACACGAAATTACCCCGATCGATTGCAACGACACCCAGATG (SEQ ID NO: 245) | 150 |
| 7-b | GAAGCTCAAACTCACCTGATCTTGAACGACGCAGCAGATGTACACGAAATTACCCCGATCGATTGCAACGACACCCAGATGATCCCGGTTTCCCGTGCACAGGAACGTCTGCTGTTCATTCATGAATTCGAAAACGGTTCTAACGCTTACAACATTGACGCGGCTTTCGAACTGCCAGGTTCTGTGGACGCGAGCCTGCTGGAACAGGCCCTTCGTGGCAACCTGGCACGTCACGAAGCACTGCGCACCCTGCTGGTTAAAGATCACGCCACTGGTATTTACCTGCAGAAAGTACTG (SEQ ID NO: 246) | 297 |
| 7-c | AGGAACGTCTGCTGTTCATTCATGAATTCGAAAACGGTTCTAACGCTTACAACATTGACGCGGCTTTCGAACTGCCAGGTTCTGTGGACGCGAGCCTGCTGGAACAGGCCCTTCGTGGCAACCTGGCACGTCACGAAGCACTGCGCACCCTGCTGGTTAAAGATCACGCCACTGGTATTTACCTGCAGAAAGTACTGAGTCCGGACGAAGCGCAAGGTATGTTTTCTGTTAATGTAGATACTGCTAAACAGGTTGAACGTCTGGATCAGGAAATTGCTTCTCTGTCTCAGCACGTCT (SEQ ID NO: 247) | 297 |
| 7-d | TTGAACGTCTGGATCAGGAAATTGCTTCTCTGTCTCAGCACGTCTTCCGCCTGGACGACGAACTGCCGTGGGAGGCGCGCATCCTGAAACTGGAATCTGGCGGTCTGTACCTGATCTTGGCCTTCCACCACACCTGCTTCGATGCATGGAGCCTGAAAGTTTTCGAACAGGAGCTGCGCGCGCTGTACGCAGCGCTTCAGAAAACGAAATCTGCAGCGAACTTACCGGCATTAAAAGCACAGTATAAGGAATACGCTCTGTACCACCGCCGCCAGCTTAGCGGCGACCGCATGCGTAA (SEQ ID NO: 248) | 298 |
| 7-e | AATACGCTCTGTACCACCGCCGCCAGCTTAGCGGCGACCGCATGCGTAACCTGTCCGATTTCTGGTTACGTAAACTGATCGGTCTGGAACCACTGCAGCTGATCACCGATCGTCCGCGTCCGGTTCAGTTCAAATACGACGGTGACGATCTGAGCATCGAACTGTCCAAGAAAGAGACCGAAAACCTGCGCGGCGTTGCAAAACGTTGTAAGTCTTCCTTATATGTTGTACTGGTATCTGTTTACTGTGTCATGCTGGCAAGCTACGCCAACCAGAGCGATGTTAGCGTGGGCAT (SEQ ID NO: 249) | 295 |
| 7-f | TGATCACCGATCGTCCGCGTCCGGTTCAGTTCAAATACGACGGTGACGATCTGAGCATCGAACTGTCCAAGAAAGAGACCGAAAACCTGCGCGGCGTTGCAAAACGTTGTAAGTCTTCCTTATATGTTGTACTGGTATCTGTTTACTGTGTCATGCTGGCAAGCTACGCCAACCAGAGCGATGTTAGCGTGGGCATCCCAGTATCACACCGTACGCACCCGCAGTTCCAGTCTGTTATCGGCTTTTTCGTTAACCTGGTCGTTCTGCGTGTAGATATCAGCCAGTCCGCTATTTGCG (SEQ ID NO: 250) | 297 |
| 8-a | GGTCGTTCTGCGTGTAGATATCAGCCAGTCCGCTATTTGCGGTTTAATCCGTCGCGTCATGAAAGAACTGGTTGACGCGCAGCTGCACCAGGATATGCCGTTCCAGGAAGTTACGAAACTGCTGCAG (SEQ ID NO: 251) | 127 |
| 8-b | GCCGTTCCAGGAAGTTACGAAACTGCTGCAGGTGGATAACGATCCTAGCCGTCACCCGTTGGTTCAGAACGTATTTAACTTTGAGTCTCGCGCGAACGGTGAACACGATGCCCGCTCTGAAGACGAGGGCTCTCTTGCATTCAATCAGTACCGTCCGGTTCAGCCGGTTGACAGCGTGGCCAAATTCGATCTGAACGCCACCGTCACCGAACTGGAATCCGGTCTGCGTGTTAATTTCAACTACGCGACCAGCTTATTCAATAAATCCACCATCCAGGGCTTCCTGCACACATATGAA (SEQ ID NO: 252) | 298 |
| 8-c | CCAGCTTATTCAATAAATCCACCATCCAGGGCTTCCTGCACACATATGAATACCTTCTGCGTCAGCTGTCCGAACTGAGCGCTGAAGGCATCAACGAAGATACCCAGCTGTCACTGGTTCGCCCGACTGAGAACGGGGATCTGCACCTGCCACTGGCCCAGTCTCCGCTCGCGACCACTGCAGAAGAACAGAAAGTTGCTTCCCTGAACCAGGCTTTCGAACGTGAAGCCTTCCTGGCGGCGGAAAAAATCGCCGTTGTTCAAGGGGACCGCGCTCTGTCGTATGCCGACCTGAAC (SEQ ID NO: 253) | 296 |
| 8-d | GCCGTTGTTCAAGGGGACCGCGCTCTGTCGTATGCCGACCTGAACGGTCAGGCTAATCAACTGGCGCGTTATATCCAGTCCGTCTCCTGCATCGGTGCCGACGACGGCATCGCCCTGATGCTGGAAAAGAGCATCGATACTATCATCTGCATTCTGGCAATCTGGAAAGCAGGCGCCGCGTATGTGCCGCTGGATCCGACCTACCCACCAGGCCGTGTACAACTGATCCTGGAGGAAATCAAAGCGAAAGCTGTGCTGGTACACTCTTCCCACGCCTCTAAATGTGAACGTCACGGTGC (SEQ ID NO: 254) | 299 |
| 9-a | CCTCTAAATGTGAACGTCACGGTGCCAAAGTCATTGCAGTAGACTCTCCGGCTATTGAAACGGCAGTGAGCCAGCAGTCTGCAGCTGATCTGCCGACCATTGCTAGCCTGGGTAATCTGGCATATATCATCTTTACTAGCGGCACT | 225 |

TABLE 3-continued

Sequences of daughter fragments obtained after Type IIS restriction enzyme digestion or nested PCR

| Fragment (Daughter fragment) | Sequence(5'→3') | Expected Length (Bp) |
|---|---|---|
| | TCTGGCAAACCGAAAGGCGTTCTGGTAGAGCAAAAAGCCGTTCTGCTGCTGCGCGACGCCCTGCGTGAGCGTT<br>ACTTCG (SEQ ID NO: 255) | |
| 9-b | ATCTTTACTAGCGGCACTTCTGGCAAACCGAAAGGCGTTCTGGTAGAGCAAAAAGCCGTTCTGCTGCTGCGCG<br>ACGCCCTGCGTGAGCGTTACTTCGGTCGTGATTGTACCAAACATCACGGTGTTCTGTTCCTGAGCAACTACGT<br>TTTCGACTTCTCCGTAGAACAGCTGGTTCTGTCTGTACTCTCAGGCCACAAACTGATTGTCCCGCCGGCGGAG<br>TTTGTGGCGGATGACGAATTCTATCGTATGGCCTCTACCCACGGTCTTTCTTACCTGTCTGGCACCCCGAGCC<br>TGCTT (SEQ ID NO: 256) | 297 |
| 9-c | TTCGACTTCTCCGTAGAACAGCTGGTTCTGTCTGTACTCTCAGGCCACAAACTGATTGTCCCGCCGGCGGAGT<br>TTGTGGCGGATGACGAATTCTATCGTATGGCCTCTACCCACGGTCTTTCTTACCTGTCTGGCACCCCGAGCCT<br>GCTTCAAAAAATCGATCTGGCACGTCTGGATCACCTGCAGGTTGTAACCGCGGCGGGTGAGGAACTCCACGCG<br>ACCCAGTACGAAAAAATGCGTCGTCGTTTTAACGGTCCAATCTACAACGCTTATGGTGTTACCGAGACAACGG<br>TGTAC (SEQ ID NO: 257) | 297 |
| 9-d | GGTCCAATCTACAACGCTTATGGTGTTACCGAGACAACGGTGTACAACATCATCGCTGAATTCACCACCAACT<br>CCATCTTCGAAAACGCATTACGCGAAGTCCTGCCGGGCACCCGTGCGTACGTTCTGAACGCGGCGCTGCAGCC<br>GGTTCCATTCGACGCTGTGGGTGAACTGTATCTGGCCGGCGATAGCGTAACCCGTGGTTACCTGAACCAGCCG<br>TTGCTGACCGATCAGCGTTTCATCCCTAACCCGTTCTGCAAGGAAGAAGACATCGCGATGGGTCGTTTCGCTC<br>GTCTGT (SEQ ID NO: 258) | 298 |
| 9-e | AAACCGGCGACCTGGTTCGCTCTCGCTTCAACCGCCAGCAGCAGCCGCAGCTGGAATACCTGGGCCGTGGCGA<br>CCTGCAGATTAAAATGCGTGGTTACCGCATTGAAATTAGCGAAGTACAGAACGTGCTGACCTCCTCCCCGGGC<br>GTACGCGAAGGTGCGGTTGTGGCTAAATATGAAAACAACGACACGTATAGCCGTACTGCACATTCCTTAGTCG<br>GTTATTATACCACTGATAACGAAACAGTTTCAGAAGCTGATATCCTCACCTTCATGAAAGCGCGTCTGCCGAC<br>CTATA (SEQ ID NO: 259) | 297 |
| 9-f | CTAACCCGTTCTGCAAGGAAGAAGACATCGCGATGGGTCGTTTCGCTCGTCTGTACAAAACCGGCGACCTGGT<br>TCGCTCTCGCTTCAACCGCCAGCAGCAGCCG (SEQ ID NO: 260) | 104 |
| 9-g | TACTGCACATTCCTTAGTCGGTTATTATACCACTGATAACGAAACAGTTTCAGAAGCTGATATCCTCACCTTC<br>ATGAAAGCGCGTCTGCCGACCTATATGGTGCCTTCTCACCTGTGCTGCCTGGAAGGTGCTCTGCCAGTCACTA<br>TTAACGGTAAACTGGACGTTCGTCGTCTGCCTGAAATTATCAACGACAGTGCGCAATCCTCATATTCCCCGCC<br>GCGCAACATTATCGAAGCGAAAATGTGCCGTTTATGGGAAAGCGCGCTGGGTATGGAACGCTGCGGTATTGAC<br>GATGAC (SEQ ID NO: 261) | 298 |
| 10-a | CGTTTATGGGAAAGCGCGCTGGGTATGGAACGCTGCGGTATTGACGATGACCTCTTCAAGCTGGGGGGGGATT<br>CTATCACCAGTCTGCACCTCGTCGCACAGATTCACAATCAGGTGGGCTGTAAGATTACCGTGCGCGATATTTT<br>CGAACACCGTACCGCGCGTGCTCTCCACGATCACGTTTTCATGAAGGATAGC (SEQ ID NO: 262) | 198 |
| 10-b | GTACCGCGCGTGCTCTCCACGATCACGTTTTCATGAAGGATAGCGATCGCTCTAACGTCACCCAGTTCCGTAC<br>CGAGCAGGGGCCGGTCATTGGCGAAGCTCCGCTGCTGCCGATCCAGGATTGGTTCTTGAGCAAAGCTCTGCAG<br>CACCCTATGTACTGGAACCACACGTTCTACGTACGTACCCCGGAACTGGACGTTGATTCCCTGAGTGCGGCCG<br>TTCGTGACCTGCAGCAGTACCACGACGTTTTCCGCATGCGCCTGAAACGCGAAGAAGTTGGCTTTGTACAGTC<br>CTTTG (SEQ ID NO: 263) | 297 |
| 10-c | TTTCCGCATGCGCCTGAAACGCGAAGAAGTTGGCTTTGTACAGTCCTTTGCCGAAGACTTTTCCCCGGCGCAG<br>CTGCGTGTACTGAACGTGAAGGACGTGGATGGTAGCGCGGCGGTTAACGAAATCCTGGACGGTTGGCAAAGCG<br>GCTTCAACCTGGAAAACGGTCCGATCGGCTCGATCGGTTATCTGCATGGCTATGAAGACCGCTCCGCACGTGT<br>GTGGTTTTCTGTACACCACATGGCCATTGACACTGTTTCCTGGCAGATCCTGGTTCGTGATCTGCAGACTCTG<br>TACCGT (SEQ ID NO: 264) | 298 |
| 10-d | ACCTGGAAAACGGTCCGATCGGCTCGATCGGTTATCTGCATGGCTATGAAGACCGCTCCGCACGTGTGTGGTT<br>TTCTGTACACCACATGGCCATTGACACTGTTTCCTGGCAGATCCTGGTTCGTGATCTGCAGACTCTGTACCGT<br>AACGGTTCCCTGGGTTCCAAAGGTTCTTCATTTCGCCAATGGGCCGAGGCAATCCAAAACTACAAAGCGAGCG<br>ACTCGGAACGTAACCATTGGAACAAGCTGGTTATGGAAACTGCATCGTCGATCAGCGCGCTGCCGACCTCCAC<br>TGGTTC (SEQ ID NO: 265) | 298 |
| 10-e | AAAACTACAAAGCGAGCGACTCGGAACGTAACCATTGGAACAAGCTGGTTATGGAAACTGCATCGTCGATCAG<br>CGCGCTGCCGACCTCCACTGGTTCTCGCGTACGTCTCTCCCGTTCTCTGTCTCCTGAAAAAACTGCTTCTCTG<br>ATCCAGGGTGGCATCGATCGTCAGGATGTAAGCGTATACGATTCTCTGCTGACTTCTGTTGGCCTGGCTTTGC<br>AACACATCGCGCCGACTGGCCCGTCTATGGTTACAATCGAGGGTCACGGCCGCGAAGAAGTTGACCAGACCCT<br>GGATG (SEQ ID NO: 266) | 297 |
| 10-f | TTCTGTTGGCCTGGCTTTGCAACACATCGCGCCGACTGGCCCGTCTATGGTTACAATCGAGGGTCACGGCCGC<br>GAAGAAGTTGACCAGACCCTGGATGTTTCTCGTACGATGGGCTGGTTCACTACCATGTATCCGTTCGAAATCC<br>CGCGTCTGTCGACGGAAAACATCGTGCAGGGTGTTGTTGCTGTAAGTGAACGCTTCCGCCAAGTTCCGGCTCG<br>CGGTGTTGGTTATGGTACTCTGTACGGTTACACCCAGCACCCTCTGCCGCAGGTTACTGTTAACTACCTGGGC<br>CAGCTG (SEQ ID NO: 267) | 298 |
| 11-a | ACACCCAGCACCCTCTGCCGCAGGTTACTGTTAACTACCTGGGCCAGCTGGCTCGTAAACAGAGCAAGCCGAA<br>AGAATGGGTTCTGGCAGTTGGTGATAACGAGTTCGAGTACGGTCTGATGACCTCCCCGGAGGATAAGGACCGT<br>TCGAGCTCCGCAGTGGATGTTACGGCCGTCTGCATCGACGGGACGATGATCATCGATGTGGACTCGGCTTGGT | 297 |

TABLE 3-continued

Sequences of daughter fragments obtained after Type IIS restriction enzyme digestion or nested PCR

| Fragment (Daughter fragment) | Sequence(5'→3') | Expected Length (Bp) |
|---|---|---|
| | CTTTGGAAGAATCTGAACAGTTCATCTCGTCAATTGAAGAAGGTCTGAACAAAATCCTGGACGGTCGTGCATC<br>CCAGC (SEQ ID NO: 268) | |
| 11-b | CGTAAACAGAGCAAGCCGAAAGAATGGGTTCTGGCAGTTGGTGATAACGAGTTCGAGTACGGTCTGATGACCT<br>CCCCGGAGGATAAGGACCGTTCGAGCTCCGCAGTGGATGTTACGGCCGTCTGCATCGACGGGACGATGATCAT<br>CGATGTGGACTCGGCTTGGTCTTTGGAAGAATCTGAACAGTTCATCTCGTCAATTGAAGAAGGTCTGAACAAA<br>ATCCTGGACGGTCGTGCATCCCAGCAGACTAGCCGCTTTCCGGATGTGCCGCAGCCAGCAGAGACCTACACCC<br>CATAC (SEQ ID NO: 269) | 297 |
| 11-c | GATGTGGACTCGGCTTGGTCTTTGGAAGAATCTGAACAGTTCATCTCGTCAATTGAAGAAGGTCTGAACAAAA<br>TCCTGGACGGTCGTGCATCCCAGCAGACTAGCCGCTTTCCGGATGTGCCGCAGCCAGCAGAGACCTACACCCC<br>ATACTTCGAATATCTGGAACCGCCGCGCCAGGGCCCGACCCTGTTTCTGCTGCCACCGGGTGAAGGTGGTGCG<br>GAATCTTACTTCAACAACATCGTCAAACGCTTGCGTCAAACTAACATGGTTGTCTTTAACAACTACTACCTGC<br>ACTCC (SEQ ID NO: 270) | 297 |
| 11-d | GAATATCTGGAACCGCCGCGCCAGGGCCCGACCCTGTTTCTGCTGCCACCGGGTGAAGGTGGTGCGGAATCTT<br>ACTTCAACAACATCGTCAAACGCTTGCGTCAAACTAACATGGTTGTCTTTAACAACTACTACCTGCACTCCAA<br>ACGTCTGCGCACCTTCGAGGAACTGGCTGAAATGTATCTGGACCAGGTACGCGGCATCCAACCGCACGGTCCA<br>TACCACTTCATCGGCTGGAGCTTCGGGGGCATTCTGGCGATGGAGATGTCCCGTCGTCTGGTTGCGAGCGACG<br>AAAA (SEQ ID NO: 271) | 296 |
| 11-e | GGCATTCTGGCGATGGAGATGTCCCGTCGTCTGGTTGCGAGCGACGAAAAAATTGGTTTTCTGGGTATTATCG<br>ACACCTATTTCAACGTACGTGGTGCCACTCGCACCATTGGCCTTGGTGATACTGAAATCCTGGATCCGATCCA<br>CCACATCTATAACCCGGACCCGGCAAACTTTCAGCGTCTGCCGTCTGCCACCGACCGTATCGTCCTGTTTAAG<br>GCCATGCGTCCGAATAATAAATATGAATCAGAAAACCAGCGTCGCCTGTATGAGTACTACGAC<br>(SEQ ID NO: 272) | 282 |
| 11-f | CTACGACGCGTTAGATTCCACGGACTGGACCGCATGTTACCAGGCGATCCCTACCTCCTCATGGTCGCGCCTG<br>CGCACGATCCACACCTTCCCGGGTTCGGAAATCCACAACCGCTGGTCCCGTTGCGTTCGTCTGAGCCGTAACA<br>CCAGCCTTGCCATCGACCCGTCTCTGGCGGCTCAGTACATCGGTCGTTGGAAGTAA (SEQ ID NO. 273) | 202 |

Nested PCR for 1 Kb DNA Synthesis Using Flanking Sequence Removed Shotgun Assembly Products The flanking sequence removed shotgun assembly products were assembled to make 11 gene cluster fragments (645-1,325 bp). The target DNA sequences are listed in Table 4.

TABLE 4

Sequences of 11 gene cluster fragments prepared by the methods of the present disclosure

| Fragment | Targeted sequence after restriction enzyme or nested PCR (5'→3') | Expected length (bp) |
|---|---|---|
| 1 | ATGACCCAATTGAAGCCGCCTAACGGGACCACTCCGATCGGCTTCAGCGCCACTACTAGCCTGAACGCTAGCG<br>GCTCTTCCTCGGTTAAGAATGGTACCATCAAGCCTTCGAATGGTATCTTCAAACCTTCTACTCGTGACACCAT<br>GGACCCGTGCTCGGGCAACGCCGCTGACGGCTCCATTCGCGTACGTTTTCGCGGTGGCATCGAACGTTGGAAA<br>GAGTGTGTAAACCAAGTGCCGGAGCGTTGCGACCTGTCTGGTCTGACCACGGACAGCACCCGCTACCAGCTGG<br>CTTCGACCGGCTTCGGCGACGCGAGCGCGGCTTACCAGGAACGTCTGATGACTGTGCCGGTAGATGTTCATGC<br>TGCGCTCCAGGAGCTGTGCCTGGAACGCCGCGTCTCTGTGGGTTCTGTGATCAACTTCAGCGTTCACCAGATG<br>CTGAAGGGTTTTGGCAACGGTACTCACACTATCACCGCGAGCCTGCACCGCGAACAGAATCTGCAGAACTCCT<br>CTCCGTCTTGGGTCGTTTCCCCTACTATCGTGACCCATGAAAACCGCGATGGCTGGTCAGTGGCGCAGGCAGT<br>GGAGTCTATCGAGGCTGGTCGTGGCTCCGAAAAGGAATCTGTGACCGCGATTGATTCCGGCTCCTCCCTGGTC<br>AAAATGGGTCTGTTCGATCTGCTGGTTTCCTTCGTCGATGCGGATGACGCGCGTATCCCTTGCTTCGACTTTC<br>CGCTGGCTGTTATTGTGCGCGAGTGCGATGCAAACCTGTCTCTCACCCTTCGCTTCTCGGACTGCCTGTTCAA<br>CGAGGAAACCATTTGTAATTTCACGGATGCCCTCAATATCCTGTTGGCTGAGGCAGTTATCGGTCGTGTAACT<br>CCGGTAGCCGATATCGAGCTGCTGTCTGCAGAGCAGAAACAACAGCTGGAGGAATGGAACAACACCGATGGTG<br>AATATCCGTCTAGCAAGCGTCTGCACCACCT (SEQ ID NO: 274) | 980 |
| 2 | GTGAATATCCGTCTAGCAAGCGTCTGCACCACCTGATTGAAGAGGTGGTGGAACGTCACGAAGACAAAATCGC<br>TGTGGTGTGCGACGAACGTGAACTGACTTACGGTGAACTCAATGCCCAGGGCAACTCCCTGGCGCGTTACCTG<br>CGTTCTGGACGACACGAAAGCCCGTGCGATTATCGCTTCCAATCAGCATGTTGAACGCCTCCAGCGTGAAGTA<br>ATCGGTGATCGCAACCTGTGCATCATCCGTCTCGAACCACTGCTGGCGAGCCTTGCGCAGGATTCTTCTAAAT<br>TCCCTGCCCACAACCTGGATGATTTGCCGCTGACCAGCCAGCAGCTGGCGTACGTTACTTATACCAGCGGTAC<br>CACCGGCTTTCCGAAAGGCATTTTCAAACAGCACACTAACGTTGTTAACTCCATCACAGACCTGTCCGCTCGT<br>TACGGTGTTGCAGGTCAACACCATGAAGCTATCCTGCTCTTCAGTGCTTGCGTTTTCGAACCGTTCGTTCGTC<br>AGACTCTGATGGCCCTGGTGAACGGTCACCTGCTCGCCGTGATTAACGATGTAGAAAAATATGACGCTGACAC<br>CCTCCTCCCATTTATCCGCCGTCACTCTATCACCTATCTGAACGGTACTGCGTCGGTTCTCCAAGAGTATGAC | 1203 |

TABLE 4-continued

Sequences of 11 gene cluster fragments prepared by the methods of the present disclosure

| Fragment | Targeted sequence after restriction enzyme or nested PCR (5'→3') | Expected length (bp) |
|---|---|---|
| | TTCTCTGACTGTCCGAGCCTGAACCGTATCATCCTGGTGGGCGAGAACCTGACCGAAGCACGTTACCTGGCAC<br>TGCGTCAGCGTTTCAAAAATCGTATTCTGAACGAGTACGGTTTCACCGAGTCTGCGTTCGTGACTGCGCTGAA<br>AATTTTCGATCCGGAAAGCACCCGCAAAGATACCTCCCTGGGGCGTCCGGTGCGCAATGTTAAATGCTATATC<br>TTGAACCCTAGCCTGAAACGCGTGCCAATTGGTGCTACAGGTGAGCTGCATATTGGCGGCCTGGGTATCTCCA<br>AGGGTTACTTGAATCGTCCGGAACTGACGCCGCACCGCTTCATCCCGAACCCGTTTCAGACCGATTGCGAAAA<br>ACAGCTGGGTATCAACTCTCTGATGTACAAAACCG (SEQ ID NO: 275) | |
| 3 | ATCGTCCGGAACTGACGCCGCACCGCTTCATCCCGAACCCGTTTCAGACCGATTGCGAAAAACAGCTGGGTAT<br>CAACTCTCTGATGTACAAAACCGGTGATCTGGCTCGCTGGCTCCCGAACGGTGAAGTTGAATACCTGGGCCGT<br>GCGGATTTCCAGATCAAACTGCGCGGTATTCGTATTGAGCCGGGCGAAATCGAGACTATGCTGGCGATGTATC<br>CGCGCGTTCGTACCTCCCTGGTGGTTTCCAAGAAATTACGTAACGGTCCTGAAGAAACAACGAACGAACACCT<br>GGTAGGCTACTACGTATGCGACTCCGCATCTGTTTCCGAAGCGGATCTGCTGTCCTTCCTGGAGAAGAAGCTG<br>CCGCGTTATATGATTCCGACTCGTCTGGTACAGCTGAGCCAGATCCCGGTTAACGTCAACGGTAAAGCCGATC<br>TGCGTGCTCTGCCGGCGGTTGATATCTCCAACAGCACCGAAGTTCGTTCTGATCTGCGTGGTGATACCGAAAT<br>TGCCCTCGGCGAAATCTGGGCGGACGTGCTGGGCGCGCGTCAGCGTTCGGTTAGCCGTAACGATAACTTTTTC<br>CGCCTCGGTGGCCACTCTATCACCTGCATCCAGCTGATTGCGCGTATCCGTCAGCGTCAGC<br>(SEQ ID NO: 276) | 645 |
| 4 | ACCTGCATCCAGCTGATTGCGCGTATCCGTCAGCGTCAGCGTTTGTCTGTGTCTATCTCTGTGGAAGACGTGT<br>TTGCTACACGCACTCTTGAGCGTATGGCCGACCTGTTGCAAAACAAACAGCAAGAGAAATGCGACAAACCACA<br>CGAAGCACCGACTGAACTGCTTGAAGAAAACGCTGCGACTGATAACATCTACCTGGCGAACAGCCTGCAGCAA<br>GGTTTCGTCTACCATTACCTGAAAAGCATGGAACAAAGTGATGCTTATGTAATGCAGAGCGTTCTGCGTTACA<br>ACACCACCCTTTCCCCGGATCTGTTCCAGCGTGCCTGGAAACACGCGCAGCAAAGCTTCCCGGCTCTGCGTCT<br>GCGCTTCTCTTGGGAAAAAGAAGTCTTCCAGCTGCTGGATCAGGACCCGCCTCTGGACTGGCGTTTCCTCTAC<br>TTCACTGATGTGGCGGCTGGTGCAGTAGAAGACCGTAAACTGGAAGATTTACGCCGCCAGGACCTCACCGAGC<br>GTTTTAAACTGGATGTGGGCCCGTCTGTTTCGCGTTTACCTGATCAAACACAGCGAAAACCGTTTCACTTGTCT<br>GTTCTCTTGTCACCACGCTATCCTGGACGGCTGGTCCTTACCGCTTCTGTTCGAAAAAGTACACGAAACATAC<br>CTGCAACTGCTGCACGGCGATAACCTGACCTCCTCTATGGATGATCCATACACCCGTACCCAACGCTACCTGC<br>ATGCGCACCGCGAAGATCACCTCGACTTTTGGGCTGGCGTGGTGCAGAAAATCAACGAACGTTGCGATATGAA<br>TGCTCTGTTAAACGAACGCAGCCGCTATAAAGTGCAGCTGGCCGACTACGATCAGGTACAGGAACAGCGTCAG<br>CTGACGATCGCTCTGAGCGGTGACGCGTGGCTGGCGGATCTGCGCCAGACATGCAGTGCGCAGGGCATCACGC<br>TGCACTCTATCCTGCAATTTGTATGGCATGCAGTTCTGCATGCCTACGGTGGCGGTACTCACACTATCACTGG<br>CACCACTATTTCTGGTCGCAA (SEQ ID NO: 277) | 1043 |
| 5 | ACGGTGGCGGTACTCACACTATCACTGGCACCACTATTTCTGGTCGCAACCTCCCGATCCTGGGTATCGAGCG<br>TGCGGTAGGCCCGTACATTAACACCCTGCCGTTAGTGTTGGACCATTCTACTTTTAAAGACAAGACGATCATG<br>GAAGCTATTGAAGACGTCCAAGCGAAGGTGAATGTTATGAACTCCCGTGGTAATGTAGAACTGGGTCGCCTGC<br>ACAAAACCGACCTGAAACATGGCCTGTTCGATTCTCTGTTTGTGCTGGAAAACTATCCAAACCTGGATAAATC<br>CCGTACTCTGGAGCACCAAACTGAACTGGGTTACTCCATCGAGGGTGGTACCGAAAAACTGAACTATCCGCTG<br>GCGGTGATTGCTCGTGAGGTTGAGACCACTGGCGGCTTTACTGTTAGCATCTGCTATGCGAGCGAACTGTTTG<br>AAGAGGTGATGATCAGCGAGCTTCTCCATATGGTACAGGATACCCTGATGCAGGTTGCACGCGGGCTCAACGA<br>ACCTGTGGGCTCCCTGGAATACCTGTCTTCCATCCAGTTAGAGCAGCTGGCAGCGTGGAACGCCACCGAAGCG<br>GAGTTCCCGGACACGACCCTGCATGAAATGTTCGAGAACGAAGCATCTCAAAAGCCGGATAAAATTGCAGTCG<br>TGTACGAAGAAACCTCTCTGACCTATCGCGAGCTGAACGAACGTGCCAATCGCATGGCGCACCAGCTGCGTTC<br>CGACGTTTCTCCGAACCCGAACGAAGTGATCGCGCTGGTTATGGACAAGAGTGAACACATGATCGTAAATATC<br>TTGGCTGTGTGGAAATCTGGTGGCGCATACGTGCCGATCGATCCGGGCTACCCGAATGACCGTATTCAGTATA<br>TCCTCGAGGACACTCAGGCGTTGGCTGTTATCGCAGATTCTTGTTACCTGCCTCGTATCAAAGGTATGGCCGC<br>GTCTGGTACGCTGCTCTACCCGTCTGTCCTGCCGGCAAACCCAGACAGCAAATGGTCTGTGTCAAACCCGTCG<br>CCGCTGTCTCGTAGCACCGACCTGGCATACATCATCTACACCTCTGGCACCACCGGCCGCCCGAAAGGCGTGA<br>CTGTGGAGCATCACGGTGTGGTGAACCTGCAGGTATCCCTGAGCAAAGTTTTTGGTCTGCGTGACACCGACGA<br>CGAAGTCATCCTGTCTTTTTCTAACTACGTTTTCGATCACTTCGTAGAACAGATGACTGATGCTATCCTGAAC<br>GGGC (SEQ ID NO: 278) | 1245 |
| 6 | CTAACTACGTTTTCGATCACTTCGTAGAACAGATGACTGATGCTATCCTGAACGGGCAGACGCTGCTGGTTCT<br>GAACGATGGTATGCGTGGTGACAAAGAACGCCTGTACCGCTACATCGAAAAGAACCGTGTAACTTATCTGTCT<br>GGTACTCCATCTGTGGTGTCTATGTATGAGTTCAGCCGTTTCAAAGACCACCTGCGCCGCGTCGATTGCGTCG<br>GTGAAGCTTTCAGCGAGCCGGTCTTCGACAAAATCCGTGAAACCTTCCACGGTTTGGTTATCAATGGTTATGG<br>CCCAACTGAAGTTAGCATCACTACCCATAAGCGTTTATACCCTTTCCCAGAGCGCCGCATGGATAAGTCGATC<br>GGCCAGCAGGTCCACAACTCTACTAGCTACGTACTGAATGAAGATATGAAGCGTACCCCGATCGGTGCTGTGG<br>GTGAGCTGTACCTGGGCGGTGAAGGTGTTGTCCGCGGTTATCATAATCGTGCGGATGTTACCGCCGAGCGCTT<br>CATCCCGAACCCGTTCCAGTCTGAGGAAGATAAACGTGAAGGCCGTAACAGTCGCCTGTACAAGACGGGTGAT<br>CTGGTTCGCTGGATCCCGGGTAGCTCCGGCGAAGTCGAATACCTGGGTCGCAATGACTTCCAGGTTAAGATTC<br>GCGGCCTCCGTATCGAGCTGGGTGAAATCGAAGCGATCCTGAGCAGCTACCACGGCATTAAACAGAGCGTAGT<br>GATCGCAAAAGACTGCCGTGAGGGGGCACAGAAATTCCTGGTCGGCTATTACGTTGCAGACGCTGCCCTGCCG<br>TCCGCAGCGATCCGTCGTTTCATGCAGTCGCGCCTCCCGGGTTACATGGTTCCGTCCCGTCTGATCCTGGTTT<br>CTAAATTCCCTGTTACTCCGTCCGGGAAGCTGGACACCAAAGCACTGCCGCCGGCGGAGGAAGAAAGCGAAAT<br>CGACGTTGTTCCACCGCGCTCCGAAATTGAGCGTTCTCTCTGCGACATCTGGGCTGAACTGCTGGAAATGCAC<br>CCGGAAGAAATCGGCATTTACTCTGACTTCTTCTCCTTGGGCGGCGACAGCCTGAAATCTACTAAGTTATCCT<br>TCATGATCCATGAGTCCTTTAACCGTGCTGTGAGCGTTAGCGCGTTATTCTGCCATCGCACA<br>(SEQ ID NO: 279) | 1157 |
| 7 | TCCTTCATGATCCATGAGTCCTTTAACCGTGCTGTGAGCGTTAGCGCGTTATTCTGCCATCGCACAGTTGAAG<br>CTCAAACTCACCTGATCTTGAACGACGCAGCAGATGTACACGAAATTACCCCGATCGATTGCAACGACACCCA | 1066 |

TABLE 4-continued

Sequences of 11 gene cluster fragments prepared by the methods of the present disclosure

| Fragment | Targeted sequence after restriction enzyme or nested PCR (5'→3') | Expected length (bp) |
|---|---|---|
| | GATGATCCCGGTTTCCCGTGCACAGGAACGTCTGCTGTTCATTCATGAATTCGAAAACGGTTCTAACGCTTAC<br>AACATTGACGCGGCTTTCGAACTGCCAGGTTCTGTGGACGCGAGCCTGCTGGAACAGGCCCTTCGTGGCAACC<br>TGGCACGTCACGAAGCACTGCGCACCCTGCTGGTTAAAGATCACGCCACTGGTATTTACCTGCAGAAAGTACT<br>GAGTCCGGACGAAGCGCAAGGTATGTTTTCTGTTAATGTAGATACTGCTAAACAGGTTGAACGTCTGGATCAG<br>GAAATTGCTTCTCTGTCTCAGCACGTCTTCCGCCTGGACGACGAACTGCCGTGGGAGGCGCGCATCCTGAAAC<br>TGGAATCTGGCGGTCTGTACCTGATCTTGGCCTTCCACCACACCTGCTTCGATGCATGGAGCCTGAAAGTTTT<br>CGAACAGGAGCTGCGCGCGCTGTACGCAGCGCTTCAGAAAACGAAATCTGCAGCGAACTTACCGGCATTAAAA<br>GCACAGTATAAGGAATACGCTCTGTACCACCGCCGCCAGCTTAGCGGCGACCGCATGCGTAACCTGTCCGATT<br>TCTGGTTACGTAAACTGATCGGTCTGGAACCACTGCAGCTGATCACCGATCGTCCGCGTCCGGTTCAGTTCAA<br>ATACGACGGTGACGATCTGAGCATCGAACTGTCCAAGAAAGAGACCGAAAACCTGCGCGGCGTTGCAAAACGT<br>TGTAAGTCTTCCTTATATGTTGTACTGGTATCTGTTTACTGTGTCATGCTGGCAAGCTACGCCAACCAGAGCG<br>ATGTTAGCGTGGGCATCCCAGTATCACACCGTACGCACCCGCAGTTCCAGTCTGTTATCGGCTTTTTCGTTAA<br>CCTGGTCGTTCTGCGTGTAGATATCAGCCAGTCCGCTATTTGCG (SEQ ID NO: 280) | |
| 8 | GGTCGTTCTGCGTGTAGATATCAGCCAGTCCGCTATTTGCGGTTTAATCCGTCGCGTCATGAAAGAACTGGTT<br>GACGCGCAGCTGCACCAGGATATGCCGTTCCAGGAAGTTACGAAACTGCTGCAGGTGGATAACGATCCTAGCC<br>GTCACCCGTTGGTTCAGAACGTATTTAACTTTGAGTCTCGCGCGAACGGTGAACACGATGCCCGCTCTGAAGA<br>CGAGGGCTCTCTTGCATTCAATCAGTACCGTCCGGTTCAGCCGGTTGACAGCGTGGCCAAATTCGATCTGAAC<br>GCCACCGTCACCGAACTGGAATCCGGTCTGCGTGTTAATTTCAACTACGCGACCAGCTTATTCAATAAATCCA<br>CCATCCAGGGCTTCCTGCACACATATGAATACCTTCTGCGTCAGCTGTCCGAACTGAGCGCTGAAGGCATCAA<br>CGAAGATACCCAGCTGTCACTGGTTCGCCCGACTGAGAACGGGGATCTGCACCTGCCACTGGCCCAGTCTCCG<br>CTCGCGACCACTGCAGAAGAACAGAAAGTTGCTTCCCTGAACCAGGCTTTCGAACGTGAAGCCTTCCTGGCGG<br>CGGAAAAAATCGCCGTTGTTCAAGGGGACCGCGCTCTGTCGTATGCCGACCTGAACGGTCAGGCTAATCAACT<br>GGCGCGTTATATCCAGTCCGTCTCCTGCATCGGTGCCGACGACGGCATCGCCCTGATGCTGGAAAAGAGCATC<br>GATACTATCATCTGCATTCTGGCAATCTGGAAAGCAGGCGCCGCGTATGTGCCGCTGGATCCGACCTACCCAC<br>CAGGCCGTGTACAACTGATCCTGGAGGAAATCAAAGCGAAAGCTGTGCTGGTACACTCTTCCCACGCCTCTAA<br>ATGTGAACGTCACGGTGC (SEQ ID NO: 281) | 894 |
| 9 | CCTCTAAATGTGAACGTCACGGTGCCAAAGTCATTGCAGTAGACTCTCCGGCTATTGAAACGGCAGTGAGCCA<br>GCAGTCTGCAGCTGATCTGCCGACCATTGCTAGCCTGGGTAATCTGGCATATATCATCTTTACTAGCGGCACT<br>TCTGGCAAACCGAAAGGCGTTCTGGTAGAGCAAAAAGCCGTTCTGCTGCTGCGCGACGCCCTGCGTGAGCGTT<br>ACTTCGGTCGTGATTGTACCAAACATCACGGTGTTCTGTTCCTGAGCAACTACGTTTTCGACTTCTCCGTAGA<br>ACAGCTGGTTCTGTCTGTACTCTCAGGCCACAAACTGATTGTCCCGCCGGCGGAGTTTGTGGCGGATGACGAA<br>TTCTATCGTATGGCCTCTACCCACGGTCTTTCTTACCTGTCTGGCACCCCGAGCCTGCTTCAAAAAATCGATC<br>TGGCACGTCTGGATCACCTGCAGGTTGTAACCGCGGCGGGTGAGGAACTCCACGCGACCCAGTACGAAAAAAT<br>GCGTCGTCGTTTTAACGGTCCAATCTACAACGCTTATGGTGTTACCGAGACAACGGTGTACAACATCATCGCT<br>GAATTCACCACCAACTCCATCTTCGAAAACGCATTACGCGAAGTCCTGCCGGGCACCCGTGCGTACGTTCTGA<br>ACGCGGCGCTGCAGCCGGTTCCATTCGACGCTGTGGGTGAACTGTATCTGGCCGGCGATAGCGTAACCCGTGG<br>TTACCTGAACCAGCCGTTGCTGACCGATCAGCGTTTCATCCCTAACCCGTTCTGCAAGGAAGAAGACATCGCG<br>ATGGGTCGTTTCGCTCGTCTGTACAAAACCGGCGACCTGGTTCGCTCTCGCTTCAACCGCCAGCAGCAGCCGC<br>AGCTGGAATACCTGGGCCGTGGCGACCTGCAGATTAAAATGCGTGGTTACCGCATTGAAATTAGCGAAGTACA<br>GAACGTGCTGACCTCCTCCCCGGGCGTACGCGAAGGTGCGGTTGTGGCTAAATATGAAAACAACGACACGTAT<br>AGCCGTACTGCACATTCCTTAGTCGGTTATTATACCACTGATAACGAAACAGTTTCAGAAGCTGATATCCTCA<br>CCTTCATGAAAGCGCGTCTGCCGACCTATATGGTGCCTTCTCACCTGTGCTGCCTGGAAGGTGCTCTGCCAGT<br>CACTATTAACGGTAAACTGGACGTTCGTCGTCTGCCTGAAATTATCAACGACAGTGCGCAATCCTCATATTCC<br>CCGCCGCGCAACATTATCGAAGCGAAAATGTGCCGTTTATGGGAAAGCGCGCTGGGTATGGAACGCTGCGGTA<br>CCCACGATGAC (SEQ ID NO: 282) | 1325 |
| 10 | CGTTTATGGGAAAGCGCGCTGGGTATGGAACGCTGCGGTATTGACGATGACCTCTTCAAGCTGGGGGGGGATT<br>CTATCACCAGTCTGCACCTCGTCGCACAGATTCACAATCAGGTGGGCTGTAAGATTACCGTGCGCGATATTTT<br>CGAACACCGTACCGCGCGTGCTCTCCACGATCACGTTTTCATGAAGGATAGCGATCGCTCTAACGTCACCCAG<br>TTCCGTACCGAGCAGGGGCCGGTCATTGGCGAAGCTCCGCTGCTGCCGATCCAGGATTGGTTCTTGAGCAAAG<br>CTCTGCAGCACCCTATGTACTGGAACCACACGTTCTACGTACGTACCCCGGAACTGGACGTTGATTCCCTGAG<br>TGCGGCCGTTCGTGACCTGCAGCAGTACCACGACGTTTTCCGCATGCGCCTGAAACGCGAAGAAGTTGGCTTT<br>GTACAGTCCTTTGCCGAAGACTTTTCCCCGGCGCAGCTGCGTGTACTGAACGTGAAGGACGTGGATGGTAGCG<br>CGGCGGTTAACGAAATCCTGGACGGTTGGCAAAGCGGCTTCAACCTGGAAAACGGTCCGATCGGCTCGATCGG<br>TTATCTGCATGGCTATGAAGACCGCTCCGCACGTGTGTGGTTTTCTGTACACCACATGGCCATTGACACTGTT<br>TCCTGGCAGATCCTGGTTCGTGATCTGCAGACTCTGTACCGTAACGGTTCCCTGGGTTCCAAAGGTTCTTCAT<br>TTCGCCAATGGGCCGAGGCAATCCAAAACTACAAAGCGAGCGACTCGGAACGTAACCATTGGAACAAGCTGGT<br>TATGGAAACTGCATCGTCGATCAGCGCGCTGCCGACCTCCACTGGTTCTCGCGTACGTCTCTCCCGTTCTCTG<br>TCTCCTGAAAAAACTGCTTCTCTGATCCAGGGTGGCATCGATCGTCAGGATGTAAGCGTATACGATTCTCTGC<br>TGACTTCTGTTGGCCTGGCTTTGCAACACATCGCGCCGACTGGCCCGTCTATGGTTACAATCGAGGGTCACGG<br>CCGCGAAGAAGTTGACCAGACCCTGGATGTTTCTCGTACGATGGGCTGGTTCACTACCATGTATCCGTTCGAA<br>ATCCCGCGTCTGTCGACGGAAAACATCGTGCAGGGTGTTGTTGCTGTAAGTGAACGCTTCCGCCAAGTTCCGG<br>CTCGCGGTGTTGGTTATGGTACTCTGTACGGTTACACCCAGCACCCTCTGCCGCAGGTTACTGTTAACTACCT<br>GGGCCAGCTG (SEQ ID NO: 283) | 1251 |
| 11 | ACACCCAGCACCCTCTGCCGCAGGTTACTGTTAACTACCTGGGCCAGCTGGCTCGTAAACAGAGCAAGCCGAA<br>AGAATGGGTTCTGGCAGTTGGTGATAAACGAGTTCGAGTACGGTCTGATGACCTCCCCGGAGGATAAGGACCGT<br>TCGAGCTCCGCAGTGGATGTTACGGCCGTCTGCATCGACGGGACGATGATCATCGATGTGGACTCGGCTTGGT<br>CTTTGGAAGAATCTGAACAGTTCATCTCGTCAATTGAAGAAGGTCTGAACAAAATCCTGGACGGTCGTGCATC<br>CCAGCAGACTAGCCGCTTTCCGGATGTGCCGCAGCCAGCAGAGACCTACACCCCATACTTCGAATATCTGGAA<br>CCGCCGCGCCAGGGCCCGACCCTGTTTCTGCTGCCACCGGGTGAAGGTGGTGCGGAATCTTACTTCAACAACA | 1076 |

TABLE 4-continued

Sequences of 11 gene cluster fragments prepared by the methods of the present disclosure

| Fragment | Targeted sequence after restriction enzyme or nested PCR (5'→3') | Expected length (bp) |
|---|---|---|
| | TCGTCAAACGCTTGCGTCAAACTAACATGGTTGTCTTTAACAACTACTACCTGCACTCCAAACGTCTGCGCAC<br>CTTCGAGGAACTGGCTGAAATGTATCTGGACCAGGTACGCGGCATCCAACCGCACGGTCCATACCACTTCATC<br>GGCTGGAGCTTCGGGGGCATTCTGGCGATGGAGATGTCCCGTCGTCTGGTTGCGAGCGACGAAAAAATTGGTT<br>TTCTGGGTATTATCGACACCTATTTCAACGTACGTGGTGCCACTCGCACCATTGGCCTTGGTGATACTGAAAT<br>CCTGGATCCGATCCACCACATCTATAACCCGGACCCGGCAAACTTTCAGCGTCTGCCGTCTGCCACCGACCGT<br>ATCGTCCTGTTTAAGGCCATGCGTCCGAATAATAAATATGAATCAGAAAACCAGCGTCGCCTGTATGAGTACT<br>ACGACGCGTTAGATTCCACGGACTGGACCGCATGTTACCAGGCGATCCCTACCTCCTCATGGTCGCGCCTGCG<br>CACGATCCACACCTTCCCGGGTTCGGAAATCCACAACCGCTGGTCCCGTTGCGTTCGTCTGAGCCGTAACACC<br>AGCCTTGCCATCGACCCGTCTCTGGCGGCTCAGTACATCGGTCGTTGGAAGTAA (SEQ ID NO: 284) | |

The 11 gene cluster fragments were constructed using 3 μl water, 10 μl Phusion polymerase pre-mix (NEB, MA), 1 μl forward and reverse primers, and 5 μl of flanking sequence-cleaved shotgun assembly DNA fragments (FIG. 8*i*). The ~1 kb DNA fragments were cloned into the TOPO vector using the TOP Cloner™ Blunt core kit (Enzynomics, Korea) and submitted for Sanger sequencing. A few colonies were chosen for colony PCR using M13 primer pairs (M13F-pUC and M13R-pUC universal primer pair). The Lasergene program (DNAstar, Madison, Wis.) was used to analyze the DNA sequence data.

Nested PCR Assembly of an 11.4 Kb Gene Cluster Using Flanking Sequence Removed Shotgun Assembly Products A nested PCR method was used to assemble eleven ~1 kb fragments into the full-length target penicillin biosynthetic gene cluster.

The PCR was performed using eleven ~1 kb fragments (each 1 μl) and 15 μl of Phusion polymerase pre-mix (NEB, MA) in the absence of primers as follows: (a) a pre-denaturation step at 95° C. for 3 min; (b) a 10-cycle PCR step, each cycle consisting of 95° C. for 30 s, 70° C. for 30 s, and 72° C. for 3 min 30 s; and (c) a final elongation step at 72° C. for 5 min.

1 μl primer pairs containing restriction enzyme sites (BglII or NotI) were added to the mixture (~1 kb fragments (each 1 μl) and 15 μl of Phusion polymerase pre-mix) and 25 more PCR cycles were performed. The PCR products were used for cloning.

After gel-electrophoresis, bands of the desired size were excised and DNA was purified. The products were cloned into a pBK3 vector (Kim, H., et al., 2010) using BglII and NotI restriction enzymes, and C2566 *E. coli* competent cells were transformed with the vector. After overnight growth at 37° C., a few colonies were screened for pBK3 vector containing the desired DNA insert size using colony PCR. Several colonies were grown in LB media for plasmid extraction using an AccuPrep™ plasmid extraction kit (Bioneer, Korea). The extracted plasmid was submitted for sequencing. Sequencing data were analyzed using the Lasergene program (DNAstar, Madison, Wis., USA).

Results and Discussion

The shotgun DNA synthesis technology was developed to overcome the challenges of high-throughput DNA construction. 228 oligonucleotides were designed to construct a penicillin biosynthetic gene cluster [N-(5-amino-5-carboxypentanoyl)-L-cysteinyl-D-valine synthase, 11,376 bp]. Chip oligonucleotides were designed to contain generic flanking sequences and cleaved from a 55K Agilent DNA microchip. Selective amplification was carried out using flanking sequences and amplification primer sequences were removed using the Type IIS restriction enzymes to obtain a sub-pool of chip oligonucleotides (FIGS. 8*a* and 8*b*).

The key point for the success of the method of the present disclosure is based on the hypothesis that a pool of oligonucleotides can be shotgun assembled in one pot to produce heterogeneous assembly products, and that each one of these products can be identified by high-throughput sequencing. Thus, oligonucleotides, at least one end of which had been cleaved, were used for shotgun DNA synthesis. As expected, highly heterogeneous DNA fragments ranging in size from 100 bp to 1,000 bp were produced (FIG. 8*c*). DNA corresponding to the 300-500 bp region were isolated from the highly heterogeneous DNA fragments by agarose gel electrophoresis. The sizes of the DNA fragments were determined taking into consideration the limit (400-500 bp) of current 454 high-throughput sequencing read length.

The present inventors then focused on developing a method to identify random fragment compositions using high-throughput sequencing technology, as well as a method to obtain sequence-validated error-free fragments from the pool of DNA fragments (FIG. 7). In the attainment of the object stated above, DNA fragments tagged with barcodes were gel-purified through amplification with barcode primer sequences (FIG. 8). The present inventors assumed that the DNA fragments would contain generic flanking sequences at both ends of the fragments for the following reasons. The efficiency of the flanking sequence cleavage of the amplified chip oligonucleotides never reaches 100%. As a consequence, flanking sequences remaining uncut at both ends of chip oligonucleotides cause termination of the DNA assembly process. This termination creates intermediates containing generic flanking sequences at both ends. This pre-termination has been considered a critical drawback in developing chip DNA synthesis technology. However, the present inventors expected that the flanking sequences contained in the fragments could be greatly helpful in tagging the randomly assembled products with the sequence containing degenerate barcode sequences by PCR amplification using primers (connecting the flanking sequences contained in the fragments and the degenerate barcode sequences).

The tagging barcode primer sequences consisted of three parts containing the original primer sequences used for the amplification of DNA chip: (a) generic primer sequences used in designing oligonucleotides, (b) 20 bp degenerate-barcode sequences, and (c) 454 primer sequences. The barcode sequence-attached shotgun assembly fragments were further amplified using the 454 primer sequences to increase the concentration of the barcoded assembly products.

It was found that through 454 sequencing analysis of the shotgun assembly fragments, 3% of the DNA fragments (~400 bp) were error-free (FIG. 9*a*). An in-house Python computer program was developed to determine error-free sequences for use in the subsequent assembly process (FIGS. 9*a* and 9*b*). Briefly, the program scans the flanking sequences containing Type IIS enzyme regions in the sequencing data to align the internal sequences to the target reference sequence. When the internal sequences (<300 bp) match perfectly with the reference sequence, the program determines the optimal set of internal sequences that overlap by 20-50 bp with other fragments, which is then applied to the next round of the assembly process (FIG. 8*g*).

This analysis using the Python program resulted in error-free shotgun assembled DNA fragments (~300 bp) covering 88% of the 11,376 bp target sequence. For the remaining ~12% DNA sequences, the error containing sequences were analyzed to determine which sequences could be re-amplified using primers. 61 pairs of PCR barcode primers were selected from a pool of random assembly products.

The desired shotgun assembly fragments were selectively amplified from the DNA mixtures using degenerate-barcode primer sequences. Based on the gel data (~400 bp), 77% (47 out of 61) of selective amplification reactions resulted in the desired sequences. The non-amplified target sequences were re-evaluated through the Python program. As a result, alternative oligonucleotide sequences were ordered. The alternative primer sequences could be utilized to obtain 100% sequences, which could be used for target DNA synthesis. The sequences (~10%) were TOPO cloned for Sanger DNA sequencing to evaluate their effectiveness. About 99.98% of the Sanger sequencing-evaluated sequences matched with the target reference sequence.

Amplicons using selected DNA include flanking sequences containing Type IIS restriction enzyme recognition sequences used in the processing procedure of chip oligonucleotides. Accordingly, prior to assembly of the amplified error-free fragments into the target DNA, the barcode sequences of the amplified fragments were cleaved with Type II restriction enzymes (Type IIS restriction enzyme, EarI, BtsI or EcoP15I) (FIG. 7). For the second round of DNA assembly, 3-7 flanking sequence-cleaved fragments (each ~300 bp) were pooled and 11 fragments (each ~1 kb long) were constructed by nested PCR (FIG. 8*i*). As illustrated in FIG. 7, 5-end and 3-end primer sets of the 11 gene fragments, each of which contained the same base sequence as the target gene fragment, were used for DNA assembly. The chemically synthesized 1 kb DNA fragments were TOPO cloned and submitted for Sanger sequencing to validate their sequences. In summary, 1-3 colonies were chosen from each of the 11 constructs for sequencing, and as a result, nine of the constructs were confirmed to contain at least one desired DNA sequence (16 out of 21 colonies were error-free with an error rate of 0.022% (i.e. 5 errors per 22,903 bp). Final nested PCR assembly was performed using the 11 sequence-validated DNA fragments (FIG. 8*j*) to construct the penicillin biosynthetic gene cluster, and the products were cloned for sequencing. As a result of the sequencing, the desired penicillin gene cluster was successfully obtained (no error per 11,400 bp).

It is worth to further discuss various points in order to illustrate the creative features of the present disclosure. First, the shotgun synthesis of the present disclosure can provide a solution to the intrinsic challenges associated with low DNA assembly efficiency. DNA assembly processes occur less efficiently due to the increased number of oligonucleotides in a sub-pool (causing a low oligonucleotide concentration) and the presence of partially cleaved flanking sequences in the oligonucleotides. For example, highly heterogeneous by-products of ~100-500 bp corresponding to small-sized DNA fragments were observed continuously during assembly of target gene clusters. In contrast, the shotgun DNA synthesis of the present disclosure enables the use of highly heterogeneous by-products in subsequent DNA assembly processes and therefore has advantages over conventional gene synthesis methods.

Second, a method of identifying and isolating error-free DNA fragments from a number of random shotgun assembly products was successfully developed. Barcoded primer sequences of the synthetic DNA sequence were validated by high-throughput sequencing. The barcode sequences could be utilized in selective PCR amplification of desired DNA molecules from a pool of the DNA molecules. After removal of the amplification primer sequences from the selectively amplified target DNA fragments, the fragments were hierarchically used in the assembly of the target sequence. In addition, it is evident that when the size of the target DNA molecules is sufficient to be sequenced at one time by the next-generation sequencing technology, the products obtained in the first round of the shotgun synthesis can be directly used.

Third, a cost estimate for DNA synthesis using Agilent chip-oligonucleotides and high-throughput sequencing is provided below. The two major costs associated with synthesis of large DNA are the costs of oligonucleotides and sequencing. The synthesis cost of chip oligonucleotides is expected to be $0.00085/nt, which is 100 times cheaper than resin-based oligonucleotides (Kim et al., 2011). In addition, 454 sequencing reads were computationally analyzed for sequencing cost-analysis. As a result, it was confirmed that 3% of the 300 bp DNA fragments produced in the first round of shotgun synthesis were error-free. The sequencing reading was performed using ⅛ lane of Roche-454 sequencing, which costs about $1,500. That is, the cost of synthesizing the 10 kb gene cluster was close to $3,000 (the cost of synthesizing oligonucleotides=$ 0.00085/nt*2*228*150 nt=$60; and the cost of various primers=$0.1/nt*200*20 nt=$400; the cost of Sanger sequencing=$3*100 reaction=$300; Roche-454 sequencing cost=$1,500; the cost of various purification kits and enzymes=$800). The cost of DNA synthesis by the synthesis method of the present disclosure is at least five times lower than the current price ($0.5/bp) charged by DNA synthesis companies. The concern that the present inventors have with this approach is the uneven coverage of the DNA assembly fragments. From the repeated assembly experiments, the present inventors found that the coverage of certain regions from the DNA assembly processes was dependent on the DNA sequences. It would be ideal to develop a shotgun assembly process that provides more uniform coverage.

Although the particulars of the present disclosure has been described in detail, it will be obvious to those skilled in the art that such particulars are merely preferred embodiments and are not intended to limit the scope of the present disclosure. Therefore, the true scope of the present disclosure is defined by the appended claims and their equivalents.

REFERENCES

Tian, J., et al., Accurate multiplex gene synthesis from programmable DNA microchips. *Nature,* 432, 1050-1054 (2004).

Kim H., et al., Hierarchical gene synthesis using DNA microchip oligonucleotides. *J. Biotech.,* 151, 319-324 (2011).

Kim, H., et al., A Fluorescence Selection Method for Accurate Large-Gene Synthesis. *Chembiochem,* 11(17): 2448-2452 (2010).

John Eid, et al., Real-Time DNA Sequencing from Single Polymerase Molecules. *Science,* 323, 133(2009).

Puigb, P., et al.: 2007 OPTIMIZER: A web server for optimizing the codon usage of DNA sequences. *Nucleic Acids Research,* 35:W126-W131 (2007)

Ben Yehezkel, T., et al., De novo DNA synthesis using single molecule PCR. *Nucleic Acids Res.,* 36, e107 (2008).

Zhang, K., et al., Sequencing genomes from single cells by polymerase cloning. *Nat. Biotechnol.,* 24, 680-686 (2006).

Hutchison, C. A., et al., Cell-free cloning using phi29 DNA polymerase. *Proc. Natl. Acad. Sci.* USA, 102, 17332-17336 (2005).

Borovkov A. Y., et al., High-quality gene assembly directly from unpurified mixtures of microarray-synthesized oligonucleotides. *Nucleic Acids Research.* 1-10 (2010).

Kosuri S., et al., Scalable gene synthesis by selective amplification of DNA pools from high-fidelity microchips. *Nature biotechnology.* 28, 1295-1299 (2010).

Matzas M., et al., High-fidelity gene synthesis by retrieval of sequence-verified DNA identified using high-throughput pyrosequencing. *Nature biotechnology.* 28, 1291-1294 (2010).

What is claimed is:

1. A method of preparing nucleic acid molecules, comprising (a) providing nucleic acid fragments constituting at least a portion of the complete sequence of a target nucleic acid, wherein step (a) comprises (a-1) providing a pool of oligonucleotides, each containing enzymatic cleavage sites and generic flanking sequences at at least one end, (a-2) cleaving the enzymatic cleavage sites to provide a pool of mixtures comprising the oligonucleotides, wherein at least one cleaved oligonucleotide comprises the generic flanking sequence at at least one end, and (a-3) randomly synthesizing nucleic acid fragments by assembling the oligonucleotides in the mixture using the generic flanking sequences:

(b) tagging the nucleic acid fragments with barcode sequences;

(c) validating the sequences of the nucleic acid fragments tagged with the barcode sequences, wherein the sequences of the tagged nucleic acid fragments are validated by parallel sequencing;

(d) recovering desired nucleic acid fragments among the sequence-validated nucleic acid fragments using the barcode sequences;

(e) forming long nucleic acid molecules by assembling the recovered nucleic acid fragments.

2. The method according to claim 1, wherein each of the nucleic acid fragments randomly synthesized in (a-3) contains the generic flanking sequences at at least one end.

3. The method according to claim 1, further comprising amplifying the nucleic acid fragments provided in step (a) when the nucleic acid fragments are derived from a DNA microarray.

4. The method according to claim 1, wherein the nucleic acid fragments provided in step (a) have a size of 20 to 3,000 bp.

5. The method according to claim 1, wherein the barcode sequences are mixtures of two or more kinds of randomly or intentionally designed oligonucleotides.

6. The method according to claim 1, wherein the barcode sequences are 5 to 300 bp in length.

7. The method according to claim 1, wherein the tagging with the barcode sequences is performed by a method selected from the group consisting of PCR, emulsion PCR, and ligation.

8. The method according to claim 1, wherein sequencing adaptor sequences are added to the barcode sequences.

9. The method according to claim 1, wherein step (d) is carried out by selectively amplifying the desired nucleic acid fragments with primers complementary to the barcode sequences and recovering the amplified nucleic acid fragments.

10. The method according to claim 1, wherein step (d) is carried out by selectively hybridizing the desired nucleic acid fragments with oligonucleotides complementary to the barcode sequences and recovering the hybridized nucleic acid fragments.

* * * * *